(12) United States Patent
Yadav et al.

(10) Patent No.: US 7,749,703 B2
(45) Date of Patent: *Jul. 6, 2010

(54) Δ12 DESATURASE GENE SUITABLE FOR ALTERING LEVELS OF POLYUNSATURATED FATTY ACIDS IN OLEAGINOUS YEASTS

(75) Inventors: Narendra S. Yadav, Chadds Ford, PA (US); Hongxiang Zhang, Chadds Ford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 61 days.

This patent is subject to a terminal disclaimer.

(21) Appl. No.: 11/494,318

(22) Filed: Jul. 27, 2006

(65) Prior Publication Data

US 2006/0263867 A1    Nov. 23, 2006

Related U.S. Application Data

(62) Division of application No. 10/840,325, filed on May 6, 2004, now Pat. No. 7,214,491.

(60) Provisional application No. 60/468,677, filed on May 7, 2003, provisional application No. 60/484,209, filed on Jun. 30, 2003.

(51) Int. Cl.
*C12Q 1/68* (2006.01)
*C12N 1/00* (2006.01)
*C12N 15/00* (2006.01)

(52) U.S. Cl. .............. 435/6; 435/254.1; 435/254.11

(58) Field of Classification Search ............. None
See application file for complete search history.

(56) References Cited

U.S. PATENT DOCUMENTS

| | | | |
|---|---|---|---|
| 4,666,701 | A | 5/1987 | Horrobin et al. |
| 4,758,592 | A | 7/1988 | Horrobin et al. |
| 4,826,877 | A | 5/1989 | Stewart et al. |
| 5,116,871 | A | 5/1992 | Horrobin et al. |
| 5,443,974 | A | 8/1995 | Hitz et al. |
| 6,136,574 | A | 10/2000 | Knutzon et al. |
| 6,372,965 | B1 | 4/2002 | Lightner et al. |
| 6,872,872 | B1 | 3/2005 | Lightner et al. |
| 6,919,466 | B2 | 7/2005 | Lightner et al. |
| 2005/0266537 | A1 | 12/2005 | Chen |
| 2007/0124837 | A1* | 5/2007 | Mukerji et al. ............. 800/281 |

FOREIGN PATENT DOCUMENTS

| | | |
|---|---|---|
| EP | 0005277 B1 | 1/1982 |
| WO | WO 94/11516 A1 | 5/1994 |
| WO | WO 03/099216 A2 | 12/2003 |

OTHER PUBLICATIONS

Sakuradani et al. Identifiaction of delta-12-fatty acid desaturase from arachidonic acid-producing Mortierella fungus by heterologous expression in the yeast Saccharomyces cerevisiae and the fungus Aspergillus oryzae. Eur. J. Biochem. 261: 812-820, 1999.*

Brock et al. Biology of Microorganisms, 7th ed., Prentice Hall, 1994, specifically pp. 288-289.*

Dyerberg, J. et al., Fatty Acid Composition of the plasma lipids in Greenland Eskimos, Amer. J. Clin Nutr. 28: pp. 958-966, 1975.

Dyerberg, J. et al., Eicosapentaenoic Acid and Prevention of Thrombosis and Atherosclerosis?, Lancet 2(8081): pp. 117-119, Jul. 15, 1978.

Shimokawa, H., Beneficial Effects of Eicosapentaenoic Acid on Endothelial Vasodilator Functions in Animals and Humans, World Rev. Nutr. Diet, 88: pp. 100-108, 2001.

Von Schacky et al.,Fatty Acids from Eskimos to Clical Cardiology—What Took Us So Long?, World Rev. Nutr. Diet, 88: pp. 90-99, 2001.

Domergue et al., Cloning and functional characterization of Phaeodactylum tricomutuim front-end desaturases involved in eicosapentaenoic acid biosynthesis, Eur. J. Biochem. 269: 4105-4113, 2002.

Beaudoin et al., Heterologous reconstitution in yeast of the polyunsaturated fatty acid biosynthetic pathway, Proc. Natl. Acad. Sci. U.S.A. 97(12): 6421-6, 2000.

Dyer et al.,Metabolic engineering of Saccharomyces cerevisiae for production of novel lipid compounds, Appl. Eniv. Microbiol., 59: pp. 224-230, 2002.

Ratledge, Microbial Oils and Fats: An Assessment of their Commercial Potential, C., Prog. Ind. Microbiol. 16: 119-206, 1982.

Brenner et al., Regulatory function of Delta6 Desaturase—Key Enzyme of Polyunsaturated Fatty Acid Synthesis, Adv. Exp. Med. Biol. 83: pp. 85-101, 1976.

Horrobin et al., Fatty acid metabolism in health and sisease: the role of delta-6-desaturase Am. J. Clin. Nutr. 57, (Suppl.) 732S-737S, 1993.

Accession No. AAG36933, Emericella nidulans. Jul. 10, 2001.
Accession No. AF110509, Mortierella alpina, Nov. 18, 1999.
Accession No. AAL13300, Mortierella alpina, Oct. 11, 2001.
Accession No. AF417244, Mortierella alpina, Oct. 11, 2001.
Accession No. AF161219, Amylomyces rouxii, Oct. 12, 1999.
Accession No. AB020033, Mortierella alpine, Jun. 26, 1999.
Accession No. AABX01000374, Neurospora crassa, Mar. 12, 2003.
Accession No. AABX01000577, Neurospora crassa, Mar. 12, 2003.
Supapon Passorn et al., Heterologous Expression of Mucor rouxii .12-Desaturase Gene in Saccharomyces cerevisiae, Biochemical and Biophysical Research Communications, vol. 263:47-51, 1999.

* cited by examiner

*Primary Examiner*—Michele K Joike
(74) *Attorney, Agent, or Firm*—Lynne M. Christenbury

(57) ABSTRACT

The present invention relates to a Δ12 fatty acid desaturase able to catalyze the conversion of oleic acid to linoleic acid (LA; 18:2). Nucleic acid sequences encoding the desaturase, nucleic acid sequences that hybridize thereto, DNA constructs comprising the desaturase gene, and recombinant host microorganisms expressing increased levels of the desaturase are described. Methods of increasing production of specific ω-3 and/or ω-6 fatty acids are described by overexpression of the Δ12 fatty acid desaturase or by disruption of the native gene.

4 Claims, 27 Drawing Sheets

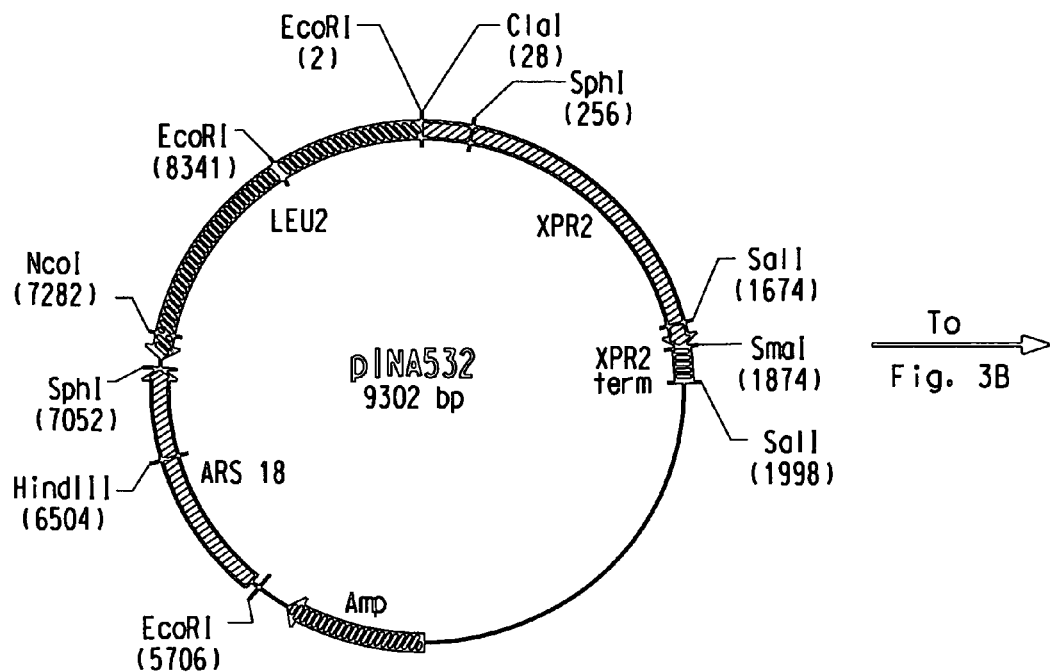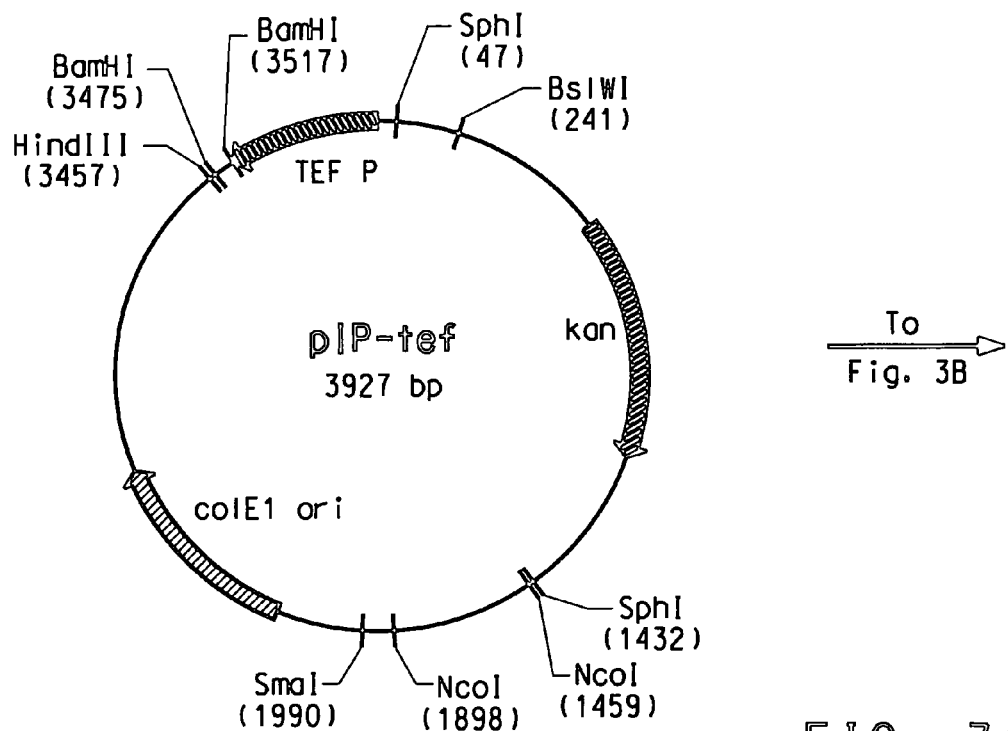
FIG. 3A

|  | En | Ma | Mr | Pa | Yl | An2 | An1 | Fm1 | Fm2 | Kl | Mab | Mac | Mg2 | Mg1 | Nc1 | Nc2 |
|---|---|---|---|---|---|---|---|---|---|---|---|---|---|---|---|---|
| Em | *** | 42 | 39 | 49 | 52 | 100 | 40 | 39 | 39 | 19 | 42 | 42 | 69 | 43 | 70 | 38 Em |
| Ma | 96 | *** | 51 | 40 | 39 | 43 | 37 | 35 | 23 | 10 | 98 | 98 | 43 | 38 | 44 | 35 Ma |
| Mr | 104 | 76 | *** | 36 | 36 | 39 | 34 | 36 | 30 | 12 | 48 | 49 | 42 | 34 | 39 | 32 Mr |
| Pa | 76 | 108 | 122 | *** | 49 | 49 | 34 | 27 | 16 | 12 | 40 | 40 | 51 | 38 | 49 | 37 Pa |
| Yl | 66 | 107 | 121 | 75 | *** | 53 | 38 | 41 | 34 | 20 | 39 | 39 | 51 | 40 | 51 | 35 Yl |
| An2 | 0 | 94 | 103 | 73 | 64 | *** | 42 | 39 | 32 | 13 | 43 | 43 | 71 | 45 | 72 | 43 An2 |
| An1 | 102 | 110 | 126 | 121 | 106 | 99 | *** | 40 | 24 | 14 | 37 | 37 | 41 | 47 | 42 | 49 An1 |
| Fm1 | 97 | 111 | 111 | 106 | 99 | 87 | 78 | *** | 28 | 3 | 37 | 38 | 38 | 53 | 39 | 49 Fm1 |
| Fm2 | 69 | 136 | 115 | 104 | 100 | 67 | 99 | 135 | *** | 10 | 26 | 26 | 62 | 32 | 56 | 32 Fm2 |
| Kl | 113 | 154 | 150 | 113 | 103 | 116 | 150 | 229 | 237 | *** | 10 | 10 | 12 | 14 | 13 | 12 Kl |
| Mab | 95 | 2 | 76 | 108 | 107 | 93 | 109 | 116 | 140 | 159 | *** | *** | 98 | 38 | 43 | 35 Mab |
| Mac | 94 | 2 | 78 | 108 | 106 | 92 | 109 | 116 | 143 | 159 | *** | 2 | 45 | 39 | 43 | 35 Mac |
| Mg2 | 39 | 95 | 99 | 74 | 75 | 37 | 100 | 114 | 47 | 115 | 95 | 95 | *** | 41 | 69 | 40 Mg2 |
| Mg1 | 98 | 113 | 135 | 112 | 104 | 92 | 77 | 60 | 106 | 139 | 112 | 112 | 106 | *** | *** | 60 Mg1 |
| Nc1 | 38 | 95 | 106 | 77 | 75 | 36 | 96 | 112 | 54 | 121 | 97 | 96 | 39 | 94 | *** | 40 Nc1 |
| Nc2 | 106 | 126 | 145 | 113 | 119 | 98 | 70 | 68 | 133 | 157 | 125 | 125 | 107 | 54 | 116 | *** Nc2 |
|  | En | Ma | Mr | Pa | Yl | An2 | An1 | Fm1 | Fm2 | Kl | Mab | Mac | Mg2 | Mg1 | Nc1 | Nc2 |

FIG. 5

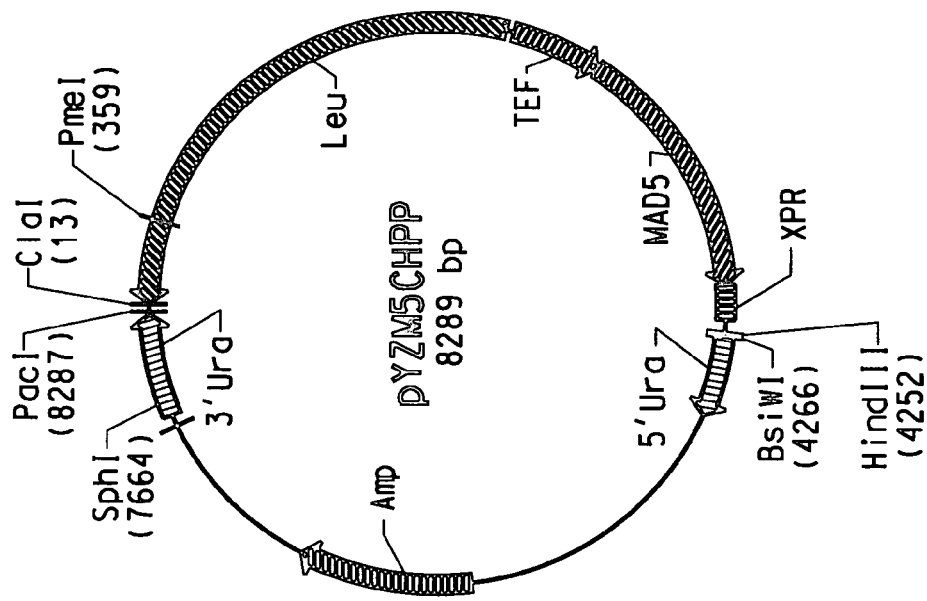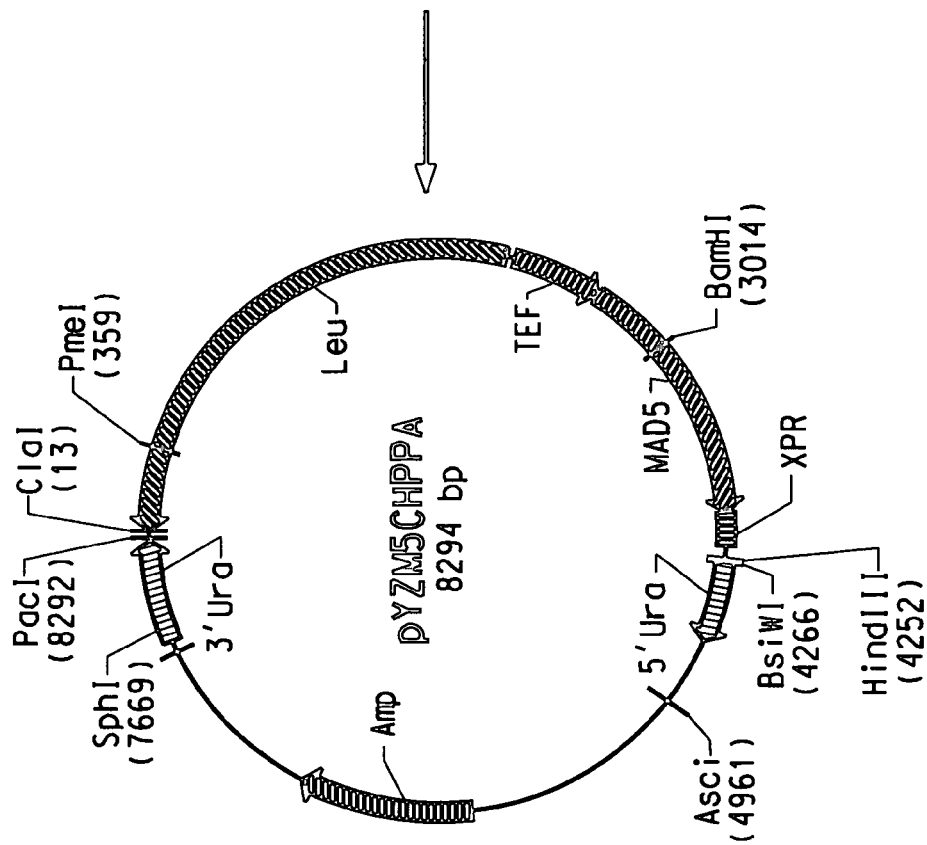
FIG. 6C

```
                                                                                               C                           T C G T         C       T T   T
(SEQ ID NO:35) ATGACTGAGGATAAGACGAAGGTCGAGTTCCCGACGCTCACGGAGCTCAAGCACTCGATCCCGAACGCGT         70
(SEQ ID NO:47)  M  T  E  D  K  T  K  V  E  F  P  T  L  T  E  L  K  H  S  I  P  N  A
                                      C              A    C              T          A T   I
               GCTTTGAGTCGAACCTCGGCCTCTCGCTCTACTACACGGCCCGCGATCTTCAACGCGTCGGCCTCGGC        140
                C  F  E  S  N  L  G  L  S  L  Y  Y  T  A  R  A  I  F  N  A  S  A  S  A
               T T         T C A T T C                                        T G
               GGGCGTGCTCTACGGCGCGCGTCGACGCCGTCATTGCCGATAACGTTCTGCTCCACGCGCTCGTTTGC        210
                A  L  L  Y  A  A  R  S  T  P  F  F  I  A  D  N  V  L  L  H  A  L  V  C
                                               T           T C       T T
               GCCACCTACATCTACGTGCAGGGCGTCATCTTCTGGGGCTTCTTCACGGTCGGCCACGACTGCGGCCACT       280
                A  T  Y  I  Y  V  Q  G  V  I  F  W  G  F  F  T  V  G  H  D  C  G  H
                       T      C A            T C                         C       C     T
               CGGCCTTCTCGCGCTACCACAGCGTCAACTTTATCATCGGCTGCATCATGCACTCTGCGATTTTGACGCC       350
                S  A  F  S  R  Y  H  S  V  N  F  I  I  G  C  I  M  H  S  A  I  L  T  P
                C     TC     A              C       A        T
               GTTCGAGAGCTGGCGCGTGACGCACCGCCACCACAAGAACACGGGCAACATTGATAAGGACGAGATC        420
                F  E  S  W  R  V  T  H  R  H  H  H  K  N  T  G  N  I  D  K  D  E  I
                 C T   T C                                A       C  A           T
               TTTTACCCGCACCGGTCGGTCAAGGACCTCCAGGACGTGCGCCAATGGTGTCTACACGCTCGGCGGTGCGT       490
                F  Y  P  H  R  S  V  K  D  L  Q  D  V  R  Q  W  V  Y  T  L  G  G  A
                        C         A       T T A C        TC            C             T
               GGTTTGTCTACTTGAAGGTCGGGTATGCCCCGCGCACGATGAGCCACTTTGACCCGTGGGACCCGCTCCT       560
                W  F  V  Y  L  K  V  G  Y  A  P  R  T  M  S  H  F  D  P  W  D  P  L  L
                G       A  A C C    T                   C          A          T  T C   C
               CCTTCGCCGCGCGTCGGCCGTCATCGTGTCGCTCGGGGTCGCCGCCTTCTTCGCCGCGTACGCGTAC       630
                L  R  R  A  S  A  V  I  V  S  L  G  V  A  A  F  F  A  A  Y  A  Y

FIG. 7A
```

```
                                                           T  T
CTCACATACTCGCTCGGCTTTGCCGTCATGGGCCTCTACTACTATGCGCCGCTCTTTGTCTTTGCTTCGT    700
 L  T  Y  S  L  G  F  A  V  M  G  L  Y  Y  Y  A  P  L  F  V  F  A  S
      T            T         T  T  C          T
TCCTCGTCATTACGACCTTCTTGCACCACAACGACGAAGCGACGCCGTGGTACGGCGACTCGGAGTGGAC    770
 F  L  V  I  T  T  F  L  H  H  N  D  E  A  T  P  W  Y  G  D  S  E  W  T
 C          GAGCTC      A      T                              TCT
GTACGTCAAGGGCAACCTCTCGAGCGTCGACCGCTCGTACGGCGGTTCGTGGACAACCTGAGCCACCAC    840
 Y  V  K  G  N  L  S  S  V  D  R  S  Y  G  G  F  V  D  N  L  S  H  H
      C                 T         T     C
ATTGGCACGCACCAGGTCCACCACTTGTTCCCGATCATTCCGCACTACAAGCTCAACGAAGCCACCAAGC    910
 I  G  T  H  Q  V  H  H  L  F  P  I  I  P  H  Y  K  L  N  E  A  T  K
        T         T      T       A  AC T                      T
ACTTTGCGGCCGCGTACCCGCACCTCGTGCGCAGGAACGACGAGCCCATCATCACGGCCTTCTTCAAGAC    980
 H  F  A  A  A  Y  P  H  L  V  R  R  N  D  E  P  I  I  T  A  F  F  K  T
         T                    A                T      T  T    C     T  T
CGGCGCACCTCTTTGTCAACTACGGCGCGGTGCCCGAGACGGCCCAGATCTTCACGCTCAAAGAGTCGGCC  1050
 A  H  L  F  V  N  Y  G  A  V  P  E  T  A  Q  I  F  T  L  K  E  S  A
 T  A         AGC
GCGGCCGCCAAGGCCAAGTCGGACTAA  1077
 A  A  A  K  A  K  S  D  .
```

FIG. 7B

CAAAATGNCG [SEQ ID NO:130]
A CC    TC
         A

Δ12 DESATURASE GENE SUITABLE FOR ALTERING LEVELS OF POLYUNSATURATED FATTY ACIDS IN OLEAGINOUS YEASTS

This application claims the benefit of U.S. Provisional Application No. 60/468,677, filed May 7, 2003, and U.S. Provisional Application No. 60/484,209, filed Jun. 30, 2003.

FIELD OF THE INVENTION

This invention is in the field of biotechnology. More specifically, this invention pertains to the identification of a nucleic acid fragment encoding a Δ12 fatty acid desaturase enzyme useful for disrupting or enhancing the production of polyunsaturated fatty acids (PUFAs) in oleaginous microorganisms, such as oleaginous yeasts.

BACKGROUND OF THE INVENTION

It has long been recognized that certain polyunsaturated fatty acids, or PUFAs, are important biological components of healthy cells. For example, such PUFAs are recognized as:
"Essential" fatty acids that can not be synthesized de novo in mammals and instead must be obtained either in the diet or derived by further desaturation and elongation of linoleic acid (LA) or α-linolenic acid (ALA);
Constituents of plasma membranes of cells, where they may be found in such forms as phospholipids or triglycerides;
Necessary for proper development, particularly in the developing infant brain, and for tissue formation and repair; and,
Precursors to several biologically active eicosanoids of importance in mammals, including prostacyclins, eicosanoids, leukotrienes and prostaglandins.

In the 1970's, observations of Greenland Eskimos linked a low incidence of heart disease and a high intake of long-chain ω-3 PUFAs (Dyerberg, J. et al., *Amer. J. Clin Nutr.* 28:958-966 (1975); Dyerberg, J. et al., *Lancet* 2(8081):117-119 (Jul. 15, 1978)). More recent studies have confirmed the cardiovascular protective effects of ω-3 PUFAs (Shimokawa, H., *World Rev Nutr Diet*, 88:100-108 (2001); von Schacky, C., and Dyerberg, J., *World Rev Nutr Diet*, 88:90-99 (2001)). Further, it has been discovered that several disorders respond to treatment with ω-3 fatty acids, such as the rate of restenosis after angioplasty, symptoms of inflammation and rheumatoid arthritis, asthma, psoriasis and eczema. γ-linolenic acid (GLA, an ω-6 PUFA) has been shown to reduce increases in blood pressure associated with stress and to improve performance on arithmetic tests. GLA and dihomo-γ-linolenic acid (DGLA, another ω-6 PUFA) have been shown to inhibit platelet aggregation, cause vasodilation, lower cholesterol levels and inhibit proliferation of vessel wall smooth muscle and fibrous tissue (Brenner et al., *Adv. Exp. Med. Biol.* 83: 85-101 (1976)). Administration of GLA or DGLA, alone or in combination with eicosapentaenoic acid (EPA, an ω-3 PUFA), has been shown to reduce or prevent gastrointestinal bleeding and other side effects caused by non-steroidal anti-inflammatory drugs (U.S. Pat. No. 4,666,701). Further, GLA and DGLA have been shown to prevent or treat endometriosis and premenstrual syndrome (U.S. Pat. No. 4,758,592) and to treat myalgic encephalomyelitis and chronic fatigue after viral infections (U.S. Pat. No. 5,116,871). Other evidence indicates that PUFAs may be involved in the regulation of calcium metabolism, suggesting that they may be useful in the treatment or prevention of osteoporosis and kidney or urinary tract stones. Finally, PUFAs can be used in the treatment of cancer and diabetes (U.S. Pat. No. 4,826,877; Horrobin et al., *Am. J. Clin. Nutr.* 57 (Suppl.): 732S-737S (1993)).

PUFAs are generally divided into two major classes (consisting of the ω-6 and the ω-3 fatty acids) that are derived by desaturation and elongation of the essential fatty acids, LA and ALA, respectively. Despite a variety of commercial sources of PUFAs from natural sources [e.g., seeds of evening primrose, borage and black currants; filamentous fungi (*Mortierella*), *Porphyridium* (red alga), fish oils and marine plankton (*Cyclotella, Nitzschia, Crypthecodinium*)], there are several disadvantages associated with these methods of production. First, natural sources such as fish and plants tend to have highly heterogeneous oil compositions. The oils obtained from these sources therefore can require extensive purification to separate or enrich one or more of the desired PUFAs. Natural sources are also subject to uncontrollable fluctuations in availability (e.g., due to weather, disease, or over-fishing in the case of fish stocks); and, crops that produce PUFAs often are not competitive economically with hybrid crops developed for food production. Large-scale fermentation of some organisms that naturally produce PUFAs (e.g., *Porphyridium, Mortierella*) can also be expensive and/or difficult to cultivate on a commercial scale.

As a result of the limitations described above, extensive work has been conducted toward: 1.) the development of recombinant sources of PUFAs that are easy to produce commercially; and 2.) modification of fatty acid biosynthetic pathways, to enable production of desired PUFAs. For example, advances in the isolation, cloning and manipulation of fatty acid desaturase and elongase genes from various organisms have been made over the last several years. Knowledge of these gene sequences offers the prospect of producing a desired fatty acid and/or fatty acid composition in novel host organisms that do not naturally produce PUFAs. The literature reports a number of examples in *Saccharomyces cerevisiae*, such as:
Domergue, F., et al. (*Eur. J. Biochem.* 269:4105-4113 (2002)), wherein two desaturases from the marine diatom *Phaeodactylum tricornutum* were cloned into *S. cerevisiae*, leading to the production of EPA;
Beaudoin F., et al. (*Proc. Natl. Acad. Sci. U.S.A.* 97(12): 6421-6426 (2000)), wherein the ω-3 and ω-6 PUF-A biosynthetic pathways were reconstituted in *S. cerevisiae*, using genes from *Caenorhabditis elegans*;
Dyer, J. M. et al. (*Appl. Eniv. Microbiol.*, 59:224-230 (2002)), wherein plant fatty acid desaturases (FAD2 and FAD3) were expressed in *S. cerevisiae*, leading to the production of ALA; and,
U.S. Pat. No. 6,136,574 (Knutzon et al., Abbott Laboratories), wherein one desaturase from *Brassica napus* and two desaturases from the fungus *Mortierella alpina* were cloned into *S. cerevisiae*, leading to the production of LA, GLA, ALA and STA.

There remains a need, however, for an appropriate microbial system in which these types of genes can be expressed to provide for economical production of commercial quantities of one or more PUFAs. Additionally, a need exists for oils enriched in specific PUFAs, notably EPA and DHA.

One class or microorganisms that has not been previously examined as a production platform for PUFAs are the oleaginous yeasts. These organisms can accumulate oil up to 80% of their dry cell weight. The technology for growing oleaginous yeast with high oil content is well developed (for example, see EP 0 005 277B1; Ratledge, C., *Prog. Ind. Microbiol.* 16:119-206 (1982)) and may offer a cost advantage compared to commercial micro-algae fermentation for production of ω-3 or ω-6 PUFAs. Whole yeast cells may also represent a convenient way of encapsulating ω-3 or ω-6 PUFA-enriched oils for use in functional foods and animal feed supplements.

Despite the advantages noted above, most oleaginous yeast are naturally deficient in ω-6 and ω-3 PUFAs, since naturally produced PUFAs in these organisms are usually limited to 18:2 fatty acids (and less commonly, 18:3 fatty acids). Thus, the problem to be solved is to develop an oleaginous yeast that accumulates oils enriched in ω-3 and/or ω-6 fatty acids. Toward this end, it is not only necessary to introduce the required desaturases and elongases that allow for the synthesis and accumulation of ω-3 and/or ω-6 fatty acids in oleaginous yeasts, but also to increase the availability of the 18:2 substrate (i.e., LA). Generally, the availability of this substrate is controlled by the activity of Δ12 desaturases that catalyze the conversion of oleic acid to LA.

There are a variety of known Δ12 desaturases disclosed in the public literature, some of which originate from fungal sources (e.g., *Mortierella alpina, Emericella nidulans, Mucor rouxii*). These desaturases are not known to be effective for altering fatty acid composition in oleaginous yeasts and are not preferred for use in oleaginous yeasts. Thus, there is need for the identification and isolation of genes encoding Δ12 desaturases that will be suitable for expression in these particular host organisms for use in the production of PUFAs.

Applicants have solved the stated problem by isolating the gene encoding a Δ12 desaturase from the oleaginous yeast, —*Yarrowia lipolytica*.

SUMMARY OF THE INVENTION

The invention relates to a gene encoding a Δ12 desaturase enzyme isolated from *Yarrowia* useful for the manipulation of the biochemical pathway for the production of ω-3 and/or ω-6 fatty acids. Accordingly, the invention provides an isolated nucleic acid molecule encoding a *Yarrowia* Δ12 desaturase enzyme, selected from the group consisting of:
  (a) an isolated nucleic acid molecule encoding the amino acid sequence as set forth in SEQ ID NO:24;
  (b) an isolated nucleic acid molecule that hybridizes with (a) under the following hybridization conditions: 0.1× SSC, 0.1% SDS, 65° C. and washed with 2×SSC, 0.1% SDS followed by 0.1×SSC, 0.1% SDS; or an isolated nucleic acid molecule that is complementary to (a) or (b).

Additionally the invention provides transformed host cells comprising the nucleic-acid molecules of the invention, genetic chimera and polypeptides encoded by the same.

In an alternate embodiment the invention provides a method for the production of linoleic acid comprising:
  a) providing a yeast comprising:
    (i) a chimeric gene of the invention encoding a Δ12 desaturase polypeptide; and
    (ii) a source of desaturase substrate consisting of oleic acid;
  b) growing the yeast of step (a) under conditions wherein the gene encoding a Δ12 desaturase polypeptide is expressed and the oleic acid is converted to linoleic acid; and
  c) optionally recovering the linoleic acid of step (b).

In another embodiment the invention provides a method for producing ω-3 fatty acids comprising:
  a) engineering a microbial host cell comprising the following elements:
    (i) a disrupted endogenous gene encoding a Δ12 desaturase polypeptide; and
    (ii) genes encoding enzymes of the ω-3 fatty acid biosynthetic pathway; and
  b) providing a source of desaturase substrate consisting of α-linolenic acid;
  c) growing the yeast of step (a) under conditions wherein the genes of the ω-3 fatty acid biosynthetic pathway are expressed, producing ω-3 fatty acids; and
  d) optionally recovering the ω-3 fatty acids of step (c).

Similarly the invention provides a method for modulating the biosynthesis of ω-3 or ω-6 fatty acids in a host cell comprising:
  a) providing a host cell comprising a functional ω-3/ω-6 fatty acid biosynthetic pathway;
  b) over-expressing a Δ12 desaturase gene in the host cell of (a); whereby the biosynthesis of ω-3 or ω-6 fatty acids is modulated.

In another embodiment the invention provides a method of obtaining a nucleic acid molecule encoding a Δ12 desaturase enzyme comprising:
  (a) probing a genomic library with the nucleic acid molecule of the invention;
  (b) identifying a DNA clone that hybridizes with the nucleic acid molecule of the invention; and
  (c) sequencing the genomic fragment that comprises the clone identified in step (b),
wherein the sequenced genomic fragment encodes a Δ12 desaturase enzyme.

Similarly the invention provides a method of obtaining a nucleic acid molecule encoding a Δ12 desaturase enzyme comprising:
  (a) synthesizing at least one oligonucleotide primer corresponding to a portion of the sequence as set forth in SEQ ID NOs:23; and
  (b) amplifying an insert present in a cloning vector using the oligonucleotide primer of step (a);

wherein the amplified insert encodes a portion of an amino acid sequence encoding a Δ12 desaturase enzyme.

BRIEF DESCRIPTION OF THE DRAWINGS AND SEQUENCE DESCRIPTIONS

FIG. 5 shows a pairwise comparison (% Identity) between and among different yeast and fungal Δ12 desaturase homologs using a ClustalW analysis (Megalign program of DNASTAR sofware).

FIG. 7 shows a comparison between the DNA sequence of the *Saprolegnia diclina* Δ17 desaturase gene and the synthetic gene codon-optimized for expression in *Y. lipolytica*.

FIG. 8 illustrates the favored consensus sequences around the translation initiation codon 'ATG' in *Y. lipolytica*.

Figure 1:
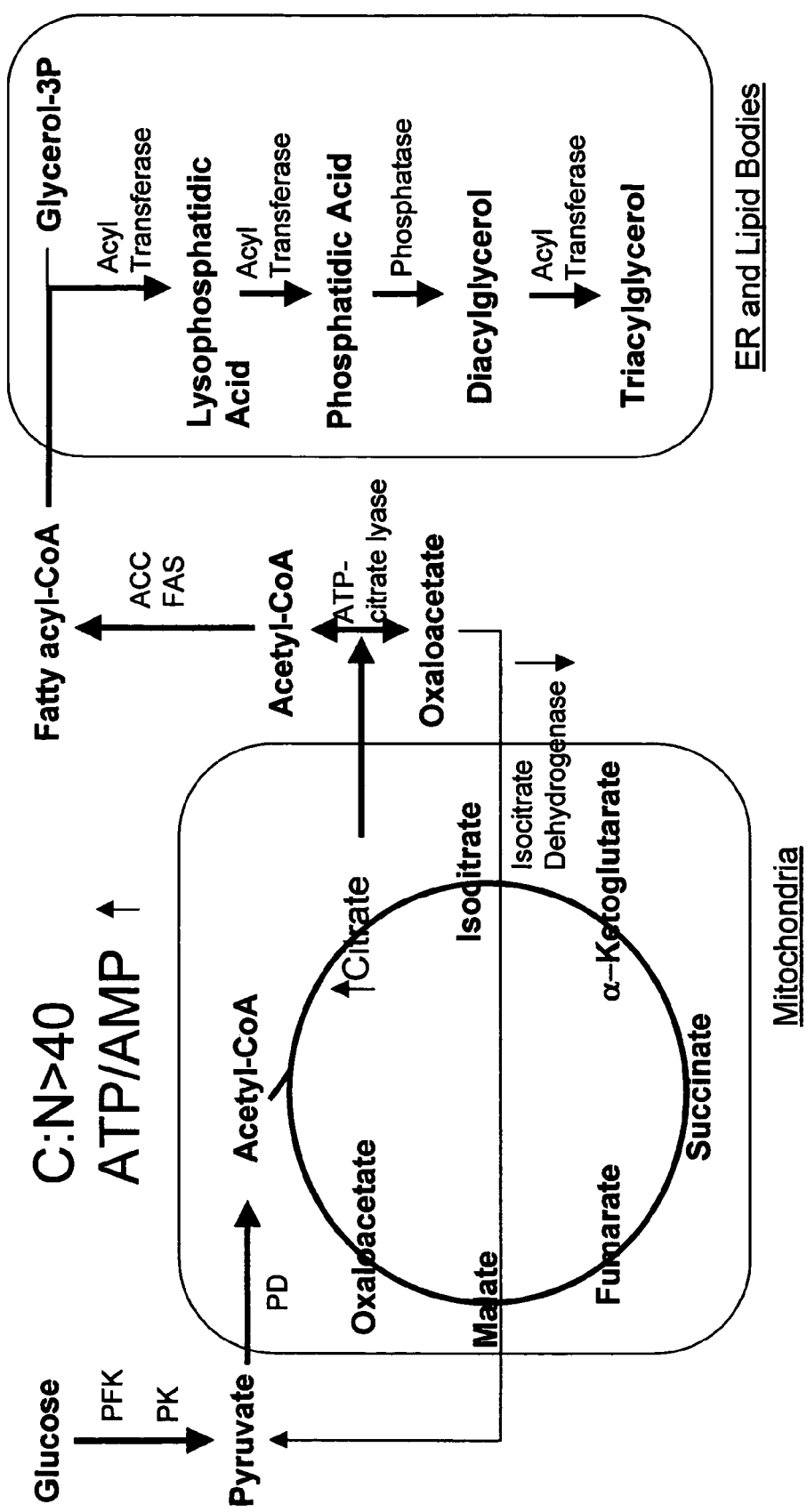
FIG. 1 shows a schematic illustration of the biochemical mechanism for lipid accumulation in oleaginous yeast.

The invention can be more fully understood from the following detailed description and the accompanying sequence descriptions, which form a part of this application.

The following sequences comply with 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NOs:1 and 2 correspond to primers TEF5' and TEF3', respectively, used to isolate the TEF promoter.

SEQ ID NOs:3 and 4 correspond to primers XPR5' and XPR3', respectively, used to isolate the XPR2 transcriptional terminator.

SEQ ID NOs:5-18 correspond to primers YL1, YL2, YL3, YL4, YL23, YL24, YL5, YL6, YL9, YL10, YL7, YL8, YL61 and YL62, respectively, used for plasmid construction.

SEQ ID NOs:19 and 21 are the degenerate primers identified as P73 and P76, respectively, used for the isolation of a *Yarrowia lioplytica* Δ12 desaturase gene.

SEQ ID NOs:20 and 22 are the amino acid consensus sequences that correspond to the degenerate primers P73 and P76, respectively.

SEQ ID NO:23 shows the DNA sequence of the *Y. lipolytica* Δ12 desaturase gene, while SEQ ID NO:24 shows the amino acid sequence of the *Y. lipolytica* Δ2 desaturase.

SEQ ID NOs:25-28 correspond to primers P99, P100, P101 and P102, respectively, used for targeted disruption of the *Y. lipolytica* Δ12 desaturase gene.

SEQ ID NOs:29-32 correspond to primers P119, P120, P121 and P122, respectively, used to screen for targeted integration of the disrupted *Y. lipolytica* Δ12 desaturase gene.

SEQ ID NOs:33 and 34 correspond to primers P147 and P148, respectively, used to amplify the full-length *Y. lipolytica* Δ12 desaturase gene.

SEQ ID NO:35 shows the DNA sequence of the *Saprolegnia diclina* Δ17 desaturase gene.

SEQ ID NO:36 shows the DNA sequence of the *Mortierella alpina* Δ6 desaturase gene, while SEQ ID NO:37 shows the amino acid sequence of the *M. alpina* Δ6 desaturase.

SEQ ID NO:38 shows the DNA sequence of the *Mortierella alpina* Δ5 desaturase gene, while SEQ ID NO:39 shows the amino acid sequence of the *M. alpina* Δ5 desaturase.

SEQ ID NOs:40 and 41 correspond to primers YL11 and YL12, respectively, used for amplifying the *M. alpina* Δ5 desaturase.

SEQ ID NOs:42 and 43 correspond to primers YL21A and YL22, respectively, used for amplifying the wild type *S. diclina* Δ17 desaturase.

SEQ ID NO:44 shows the DNA sequence of the *Mortierella alpina* high affinity elongase gene, while SEQ ID NO:45 shows the amino acid sequence of the *M. alpina* high affinity elongase.

SEQ ID NO:46 shows the DNA sequence of the synthetic Δ17 desaturase gene codon-optimized for expression in *Yarrowia lipolytica*, while SEQ ID NO:47 shows the corresponding amino acid sequence of the *S. diclina* Δ17 desaturase.

SEQ ID NOs:48-69 correspond to the 11 pairs of oligonucleotides that together comprise the entire codon-optimized coding region of the *S. diclina* Δ17 desaturase gene (e.g., D17-1A, D17-1B, D17-2A, D17-2B, D17-3A, D17-3B, D17-4A, D17-4B, D17-5A, D17-5B, D17-6A, D17-6B, D17-7A, D17-7B, D17-8A, D17-8B, D17-9A, D17-9B, D17-10A, D17-10B, D17-11A and D17-11B, respectively).

SEQ ID NOs:70-75 correspond to primers D17-1, D17-4R, D17-5, D17-8D, D17-8U and D17-11, respectively, used for PCR amplification during synthesis of the codon-optimized Δ17 desaturase gene.

SEQ ID NOs:76 and 77 correspond to primers YL53 and YL54, respectively, used for site-directed mutagenesis to generate pYSD17M.

SEQ ID NOs:78 and 79 correspond to primers KU5 and KU3, respectively, used for amplifying a 1.7 kB DNA fragment (SEQ ID NO:80; amino acid sequence provided as SEQ ID NO:81) containing the *Yarrowia* URA3 gene.

SEQ ID NOs:82 and 83 correspond to primers KI5 and KI3, respectively, used for amplifying a 1.1 kB DNA fragment (SEQ ID NO:84; amino acid sequence provided as SEQ ID NO:85) containing the conjugase gene of *Impatients balsama*.

SEQ ID NOs:86 and 87 correspond to primers KTI5 and KTI3, respectively, used for amplifying a 1.7 kB DNA fragment (SEQ ID NO:88; amino acid sequence provided as SEQ ID NO:89) containing a TEF::conjugase::XPR chimeric gene.

SEQ ID NOs:90 and 91 correspond to primers KH5 and KH3, respectively, used for amplifying a 1 kB DNA fragment (SEQ ID NO:92; amino acid sequence provided as SEQ ID NO:93) containing the *E. coli* hygromycin resistance gene.

SEQ ID NOs:94 and 95 correspond to primers KTH5 and KTH3, respectively, used for amplifying a 1.6 kB DNA fragment (SEQ ID NO:96; amino acid sequence provided as SEQ ID NO:97) containing the TEF::HPT::XPR fusion gene.

SEQ ID NOs:98 and 99 correspond to the 401 bp of 5'-sequence and 568 bp of 3'-sequence of the *Yarrowia lipolytica* URA3 gene, respectively, used to direct integration of expression cassettes into the Ura loci of the *Yarrowia* genome.

SEQ ID NOs:100-103 correspond to primers YL63, YL64, YL65 and YL66, respectively, used for site-directed mutagenesis to generate pY24-4.

SEQ ID NOs:104-107 correspond to primers YL81, YL82, YL83 and YL84, respectively, used for site-directed mutagenesis to generate pYZM5CH.

SEQ ID NOs:108 and 109 correspond to primers YL105 and YL106, respectively, used for site-directed mutagenesis to generate pYZM5CHPP.

SEQ ID NOs:110 and 111 correspond to primers YL119 and YL120, respectively, used for site-directed mutagenesis to generate pYZM5CHPPA.

SEQ ID NOs:112 and 113 correspond to primers YL121 and YL122, respectively, used for amplifying 440 bp of 5'-non-coding DNA sequence (SEQ ID NO:114) upstream from the *Y. lipolylica* URA3 gene.

SEQ ID NOs:115 and 116 correspond to primers YL114 and YL115, respectively, used for site-directed mutagenesis to generate pYZV5 and pYZV5P.

SEQ ID NO:117 corresponds to a 5.2 kB DNA fragment suitable for integration and expression of the Δ5 desaturase gene in the *Y. lipolytica* genome.

SEQ ID NOs:118 and 119 correspond to primers YL69 and YL70, respectively, used for site-directed mutagenesis to generate pY58BH.

SEQ ID NOs:120-123-correspond to primers YL77, YL78, YL79A and YL80A, respectively, used for site-directed mutagenesis to generate pY54PC.

SEQ ID NO:124 corresponds to a 8.9 kB DNA fragment suitable for integration and coordinate expression of the Δ6 desaturase, PUFA elongase and Δ5 desaturase genes in the *Y. lipolytica* genome.

SEQ ID NOs:125-128 correspond to primers YL101, YL102, YL103 and YL104, respectively, used for site-directed mutagenesis to generate pYSD17SPC.

SEQ ID NO:129 corresponds to a 10.3 kB DNA fragment suitable for integration and coordinate expression of the Δ6 desaturase, PUFA elongase, Δ5 desaturase and Δ17 desaturase genes in the *Y. lipolytica* genome.

SEQ ID NO:130 corresponds to the codon-optimized translation initiation site for genes optimally expressed in *Yarrowia* sp.

DETAILED DESCRIPTION OF THE INVENTION

In accordance with the subject invention, Applicants have isolated and confirmed the identity of a *Yarrowia lipolytica* gene encoding a Δ12 desaturase. Additionally, methods and compositions are provided which permit modification of the long chain polyunsaturated fatty acid (PUFA) content of oleaginous yeasts, such as *Yarrowia lipolytica*.

The invention relates to a new Δ12 desaturase enzyme and gene encoding the same that may be used for the manipulation of biochemical pathways for the production of healthful PUFAs. The subject invention finds many applications. PUFAs, or derivatives thereof, made by the methodology disclosed herein can be used as dietary substitutes, or supplements, particularly infant formulas, for patients undergoing intravenous feeding or for preventing or treating malnutrition. Alternatively, the purified PUFAs (or derivatives thereof) may be incorporated into cooking oils, fats or margarines formulated so that in normal use the recipient would receive the desired amount for dietary supplementation. The PUFAs may also be incorporated into infant formulas, nutritional supplements or other food products and may find use as anti-inflammatory or cholesterol lowering agents. Optionally, the compositions may be used for pharmaceutical use (human or veterinary). In this case, the PUFAs are generally administered orally but can be administered by any route by which they may be successfully absorbed, e.g., parenterally (e.g., subcutaneously, intramuscularly or intravenously), rectally, vaginally or topically (e.g., as a skin ointment or lotion).

Supplementation of humans or animals with PUFAs produced by recombinant means can result in increased levels of the added PUFAs, as well as their metabolic progeny. For example, treatment with arachidonic acid (ARA) can result not only in increased levels of ARA, but also downstream products of ARA such as prostaglandins. Complex regulatory mechanisms can make it desirable to combine various PUFAs, or add different conjugates of PUFAs, in order to prevent, control or overcome such mechanisms to achieve the desired levels of specific PUFAs in an individual.

Definitions

In this disclosure, a number of terms and abbreviations are used. The following definitions are provided.

"Open reading frame" is abbreviated ORF.
"Polymerase chain reaction" is abbreviated PCR.
"American Type Culture Collection" is abbreviated ATCC.
"Polyunsaturated fatty acid(s)" is abbreviated PUFA(s).

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

"PUFAs" can be classified into two major families (depending on the position (n) of the first double bond nearest the methyl end of the fatty acid carbon chain). Thus, the "omega-6 fatty acids" (ω-6 or n-6) have the first unsaturated double bond six carbon atoms from the omega (methyl) end of the molecule and additionally have a total of two or more double bonds, with each subsequent unsaturation occuring 3 additional carbon atoms toward the carboxyl end of the molecule. In contrast, the "omega-3 fatty acids" ω-3 or n-3) have the first unsaturated double bond three carbon atoms away from the omega end of the molecule and additionally have a total of three or more double bonds, with each subsequent unsaturation occuring 3 additional carbon atoms toward the carboxyl end of the molecule.

For the purposes of the present disclosure, the omega-reference system will be used to indicate the number of carbons, the number of double bonds and the position of the double bond closest to the omega carbon, counting from the omega carbon (which is numbered 1 for this purpose). This nomenclature is shown below in Table 1, in the column titled "Shorthand Notation". The remainder of the Table summarizes the common names of ω-3 and ω-6 fatty acids, the abbreviations that will be used throughout the specification and each compounds' chemical name.

TABLE 1

Nomenclature Of Polyunsaturated Fatty Acids

| Common Name | Abbreviation | Chemical Name | Shorthand Notation |
|---|---|---|---|
| Linoleic | LA | cis-9,12-octadecadienoic | 18:2 ω-6 |
| γ-Linoleic | GLA | cis-6,9,12-octadecatrienoic | 18:3 ω-6 |
| Dihomo-γ-Linoleic | DGLA | cis-8,11,14-eicosatrienoic | 20:3 ω-6 |
| Arachidonic | ARA | cis-5,8,11,14-eicosatetraenoic | 20:4 ω-6 |
| α-Linolenic | ALA | cis-9,12,15-octadecatrienoic | 18:3 ω-3 |
| Stearidonic | STA | cis-6,9,12,15-octadecatetraenoic | 18:4 ω-3 |

TABLE 1-continued

Nomenclature Of Polyunsaturated Fatty Acids

| Common Name | Abbreviation | Chemical Name | Shorthand Notation |
|---|---|---|---|
| Eicosa-tetraenoic | ETA | cis-8,11,14,17-eicosatetraenoic | 20:4 ω-3 |
| Eicosa-pentaenoic | EPA | cis-5,8,11,14,17-eicosapentaenoic | 20:5 ω-3 |
| Docosa-pentaenoic | DPA | cis-7,10,13,16,19-docosapentaenoic | 22:5 ω-3 |
| Docosa-hexaenoic | DHA | cis-4,7,10,13,16,19-docosahexaenoic | 22:6 ω-3 |

The term "essential fatty acid" refers to a particular PUFA that an individual must ingest in order to survive, being unable to synthesize the particular essential fatty acid de novo. Linoleic (18:2, ω-6) and linolenic (18:3, ω-3) fatty acids are "essential fatty acids", since humans cannot synthesize them and have to obtain them in their diet.

The term "fat" refers to a lipid substance that is solid at 25° C. and usually saturated.

The term "oil" refers to a lipid substance that is liquid at 25° C. and usually polyunsaturated. PUFAs are found in the oils of some algae, oleaginous yeasts and filamentous fungi. "Microbial oils" or "single cell oils" are those oils naturally produced by microorganisms during their lifespan. Such oils can contain long chain PUFAs.

The term "PUFA biosynthetic pathway enzyme" refers to any of the following enzymes (and genes which encode said enzymes) associated with the biosynthesis of a PUFA, including: a Δ4 desaturase, a Δ5 desaturase, a Δ6 desaturase, a Δ12 desaturase, a Δ15 desaturase, a Δ17 desaturase, a Δ9 desaturase and/or an elongase.

Figure 2:
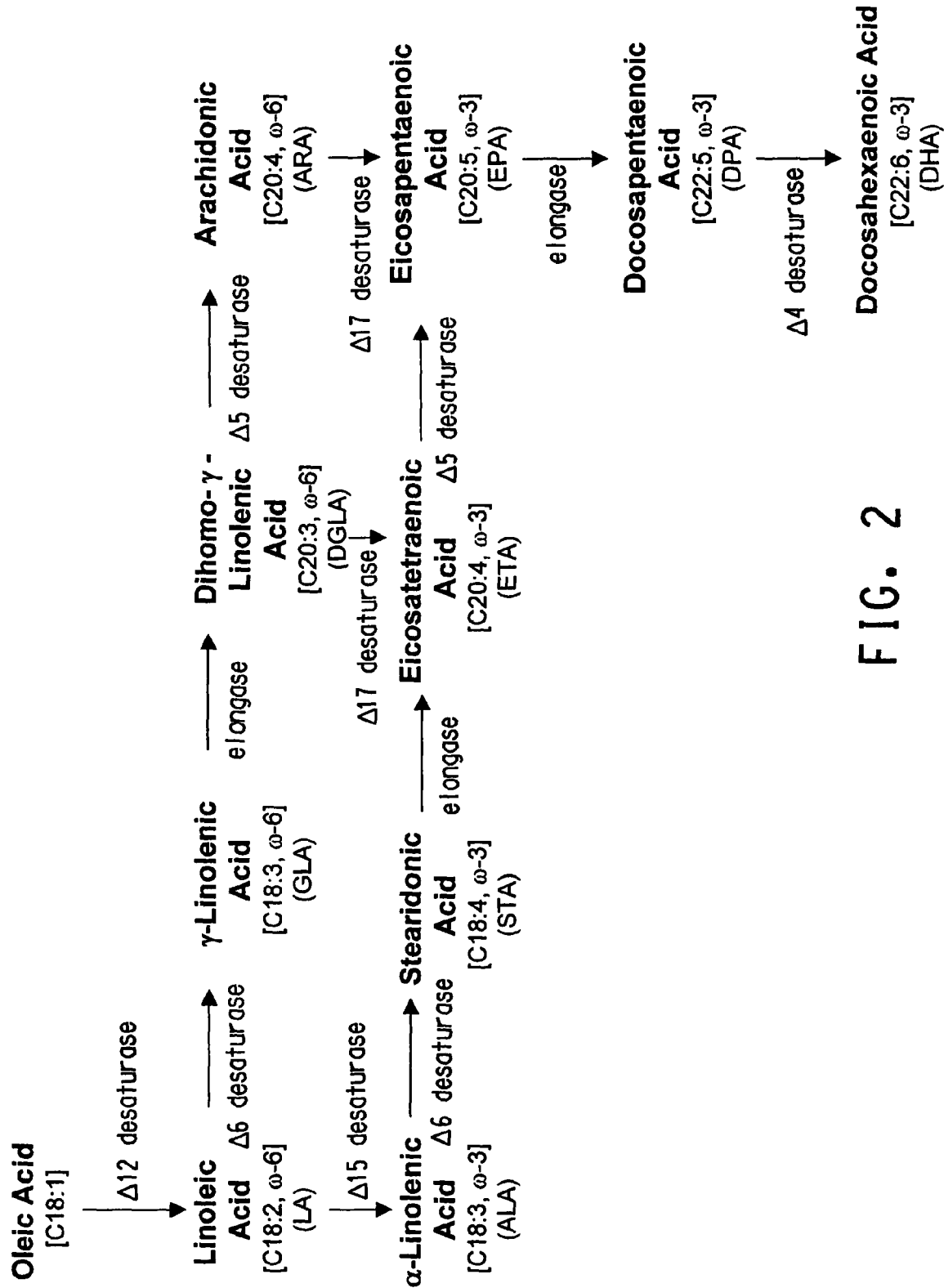
FIG. 2 illustrates the ω-3 and ω-6 fatty acid biosynthetic pathways.

The term "ω-3/ω-6 fatty acid biosynthetic pathway" refers to a set of genes which, when expressed under the appropriate conditions encode enzymes that catalyze the production of either or both ω-3 and ω-6 fatty acids. Typically the genes involved in the ω-3/ω-6 fatty acid biosynthetic pathway encode some or all of the following enzymes: Δ12 desaturase, Δ6 desaturase, elongase, Δ5 desaturase, Δ17 desaturase, Δ15 desaturase, Δ9 desaturase and Δ4 desaturase. A representative pathway is illustrated in FIG. 2, providing for the conversion of oleic acid through various intermediates to DHA, which demonstrates how both ω-3 and ω-6 fatty acids may be produced from a common source. The pathway is naturally divided into two portions where one portion will generate ω-3 fatty acids and the other portion, only ω-6 fatty acids. That portion that only generates ω-3 fatty acids will be referred to herein as the ω-3 fatty acid biosynthetic pathway whereas that portion that generates only ω-6 fatty acids will be referred to herein as the ω-6 fatty acid biosynthetic pathway.

The term "functional" as used herein in context with the ω-3/ω-6 fatty acid biosynthetic pathway means that some or all of the genes in the pathway express active enzymes. It should be understood that "ω-3/ω-6 fatty acid biosynthetic pathway" or "functional ω-3/ω-6 fatty acid biosynthetic pathway" does not imply that all the genes listed in this paragraph are required as a number of fatty acid products will only require the expression of a subset of the genes of this pathway.

The term "desaturase" refers to a polypeptide that can desaturate, i.e., introduce a double bond, in one or more fatty acids to produce a mono- or polyunsaturated fatty acid. Despite use of the omega-reference system throughout the specification in reference to specific fatty acids, it is more convenient to indicate the activity of a desaturase by counting from the carboxyl end of the substrate using the delta-system. Of particular interest herein are Δ12 desaturases that desaturate a fatty acid between the $12^{th}$ and $13^{th}$ carbon atoms numbered from the carboxyl-terminal end of the molecule and that catalyze the conversion of oleic acid to LA. Other desaturases relevant to the present disclosure include: Δ15 desaturases that catalyze the conversion of LA to ALA; Δ17 desaturases that desaturate a fatty acid between the $17^{th}$ and $18^{th}$ carbon atom numbered from the carboxyl-terminal end of the molecule and which, for example, catalyze the conversion of ARA to EPA and/or DGLA to ETA; Δ6 desaturases that catalyze the conversion of LA to GLA and/or ALA to STA; Δ5 desaturases that catalyze the conversion of DGLA to ARA and/or ETA to EPA; Δ4 desaturases that catalyze the conversion of DPA to DHA; and Δ9 desaturases that catalyze the conversion of palmitate to palmitoleic acid (16:1) and/or stearate to oleic acid (18:1).

The term "elongase" refers to a polypeptide that can elongate a fatty acid carbon chain to produce an acid that is 2 carbons longer than the fatty acid substrate that the elongase acts upon. This process of elongation occurs in a multi-step mechanism in association with fatty acid synthase, whereby CoA is the acyl carrier (Lassner et al., *The Plant Cell* 8:281-292 (1996)). Briefly, malonyl-CoA is condensed with a long-chain acyl-CoA to yield $CO_2$ and a β-ketoacyl-CoA (where the acyl moiety has been elongated by two carbon atoms). Subsequent reactions include reduction to β-hydroxyacyl-CoA, dehydration to an enoyl-CoA and a second reduction to yield the elongated acyl-CoA. Examples of reactions catalyzed by elongases are the conversion of GLA to DGLA, STA to ETA and EPA to DPA. Accordingly, elongases can have different specificities (e.g., a $C_{16/18}$ elongase will prefer a $C_{16}$ substrate, a $C_{18/20}$ elongase will prefer a $C_{18}$ substrate and a $C_{20/22}$ elongase will prefer a $C_{20}$ substrate).

The terms "conversion efficiency" and "percent substrate conversion" refer to the efficiency by which a particular enzyme (e.g., a desaturase or elongase) can convert substrate to product. The conversion efficiency is measured according to the following formula: ([product]/[substrate+product]) *100, where 'product' includes the immediate product and all products in the pathway derived from it.

The term "oleaginous" refers to those organisms that tend to store their energy source in the form of lipid (Weete, In: Fungal Lipid Biochemistry, $2^{nd}$ ed., Plenum, 1980). Generally, the cellular oil or triacylglycerol content of oleaginous microorganisms follows a sigmoid curve, wherein the concentration of lipid increases until it reaches a maximum at the late logarithmic or early stationary growth phase and then gradually decreases during the late stationary and death phases (Yongmanitchai and Ward, *Appl. Environ. Microbiol.* 57:419-25 (1991)).

The term "oleaginous yeast" refers to those microorganisms classified as yeasts that can accumulate at least 25% of their dry cell weight as oil. Examples of oleaginous yeast include, but are no means limited to, the following genera: *Yarrowia, Candida, Rhodotorula, Rhodosporidium, Cryptococcus, Trichosporon* and *Lipomyces*.

The term "fermentable carbon substrate" means a carbon source that a microorganism will metabolize to derive energy. Typical carbon substrates of the invention include, but are not limited to: monosaccharides, oligosaccharides, polysaccharides, alkanes, fatty acids, esters of fatty acids, monoglycerides, carbon dioxide, methanol, formaldehyde, formate and carbon-containing amines.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA molecule, when a single-stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washed with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., *J. Mol. Biol.* 215:403-410 (1993). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding a particular yeast protein. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing, as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) *Computational Molecular Biology* (Lesk, A. M., Ed.) Oxford University: NY (1988); 2.) *Biocomputing: Informatics and Genome Projects* (Smith, D. W., Ed.) Academic: NY (1993); 3.) *Computer Analysis of Sequence Data, Part I* (Griffin, A. M., and Griffin, H. G., Eds.) Humana: NJ (1994); 4.) *Sequence Analysis in Molecular Biology* (von Heinje, G., Ed.) Academic (1987); and 5.) *Sequence Analysis Primer* (Gribskov, M. and Devereux, J., Eds.) Stockton: NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences is performed using the Clustal method of alignment (Higgins and Sharp, *CABIOS*. 5:151-153 (1989)) with default parameters (GAP PENALTY=10, GAP LENGTH PENALTY=10). Default parameters for pairwise alignments using the Clustal method are: KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 75% identical, and more preferably at least about 80% identical to the amino acid sequence reported herein. Preferred nucleic acid fragments encode amino acid sequences that are about 85% identical to the amino acid sequence reported herein. More preferred nucleic acid fragments encode amino acid sequences that are at least about 90% identical to the amino acid sequence reported herein. Most preferred are nucleic acid fragments that encode amino acid sequences that are at least about 95% identical to the amino acid sequence reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Chemically synthesized", as related to a sequence of DNA, means that the component nucleotides were assembled in vitro. Manual chemical synthesis of DNA may be accomplished using well-established procedures; or automated chemical synthesis can be performed using one of a number of commercially available machines. "Synthetic genes" can be assembled from oligonucleotide building blocks that are chemically synthesized using procedures known to those skilled in the art. These building blocks are ligated and annealed to form gene segments that are then enzymatically assembled to construct the entire gene. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell, where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. A "codon-optimized gene" is a gene having its frequency of codon usage designed to mimic the frequency of preferred codon usage of the host cell.

"Coding sequence" refers to a DNA sequence that codes for a specific amino acid sequence. "Suitable regulatory sequences" refer to nucleotide sequences located upstream (5' non-coding sequences), within or downstream (3' non-coding sequences) of a coding sequence, and which influence the transcription, RNA processing or stability, or translation of the associated coding sequence. Regulatory sequences may include promoters., translation leader sequences, introns, polyadenylation recognition sequences, RNA processing sites, effector binding sites and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters that cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "3' non-coding sequences" or "transcription terminator" refers to DNA sequences located downstream of a coding sequence. This includes polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The 3' region can influence the transcription, RNA processing or stability, or translation of the associated coding sequence.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" or "mRNA" refers to the RNA that is without introns and that can be translated into protein by the cell. "cDNA" refers to a double-stranded DNA that is complementary to, and derived from, mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated and yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment(s) of the invention. Expression may also refer to translation of mRNA into a polypeptide.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be (but are not limited to) intracellular localization signals.

"Transformation" refers to the transfer of a nucleic acid molecule into a host organism, resulting in genetically stable inheritance. The nucleic acid molecule may be a plasmid that replicates autonomously, for example; or, it may integrate into the genome of the host organism. Host organisms containing the transformed nucleic acid fragments are referred to as "transgenic" or "recombinant" or "transformed" organisms.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a nucleotide sequence which can be measured by an assay method, where that activity is either greater than or less than the activity associated with the native sequence. "Enhanced biological activity" refers to an altered activity that is greater than that associated with the native sequence. "Diminished biological activity" is an altered activity that is less than that associated with the native sequence.

The term "homologous recombination" refers to the exchange of DNA fragments between two DNA molecules (during cross over). The fragments that are exchanged are flanked by sites of identical nucleotide sequences between the two DNA molecules (i.e., "regions of homology"). The term "regions of homology" refer to stretches of nucleotide sequence on nucleic acid fragments that participate in homologous recombination that have homology to each other. Effective homologous recombination will take place where these regions of homology are at least about 10 bp in length where at least about 50 bp in length is preferred. Typically fragments that are intended for recombination contain at least two regions of homology where targeted gene disruption or replacement is desired.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., *J. Mol. Biol.* 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used herein are well known in the art and are described by Sambrook, J., Fritsch, E. F. and Maniatis, T., *Molecular Cloning: A Laboratory Manual*, 2nd ed., Cold Spring Harbor Laboratory: Cold Spring Harbor, N.Y. (1989) (hereinafter "Maniatis"); by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience (1987).

Microbial Biosynthesis of Fatty Acids

In general, lipid accumulation in oleaginous microorganisms is triggered in response to the overall carbon to nitrogen ratio present in the growth medium (FIG. 1). When cells have exhausted available nitrogen supplies (e.g., when the carbon to nitrogen ratio is greater than about 40), the depletion of cellular adenosine monophosphate (AMP) leads to the cessation of AMP-dependent isocitrate dehydrogenase activity in the mitochondria and the accumulation of citrate, transport of citrate into the cytosol and subsequent cleavage of the citrate by ATP-citrate lyase to yield acetyl-CoA. Acetyl-CoA is the principle building block for de novo biosynthesis of fatty acids. Although any compound that can effectively be metabolized to produce acetyl-CoA can serve as a precursor of fatty acids, glucose is the primary source of carbon in this type of reaction (FIG. 1). Glucose is converted to pyruvate via glycolysis and pyruvate is then transported into the mitochondria where it can be converted to acetyl-CoA by pyruvate dehydrogenase ("PD"). Since acetyl-CoA can not be transported directly across the mitochondrial membrane into the cytoplasm, the two carbons from acetyl-CoA condense with oxaloacetate to yield citrate (catalyzed by citrate synthase). Citrate is transported directly into the cytoplasm, where it is cleaved by ATP-citrate lyase to regenerate acetyl-CoA and oxaloacetate. The oxaloacetate reenters the tricarboxylic acid cycle, via conversion to malate.

The synthesis of malonyl-CoA is the first committed step of fatty acid biosynthesis, which takes place in the cytoplasm. Malonyl-CoA is produced via carboxylation of acetyl-CoA by acetyl-CoA carboxylase ("ACC"). Fatty acid synthesis is catalyzed by a multi-enzyme fatty acid synthase complex ("FAS") and occurs by the condensation of eight two-carbon fragments (acetyl groups from acetyl-CoA) to form a 16-carbon saturated fatty acid, palmitate. More specifically, FAS catalyzes a series of 7 reactions, which involve the following (Smith, S. *FASEB J,* 8(15):1248-59 (1994)):

1. Acetyl-CoA and malonyl-CoA are transferred to the acyl carrier peptide (ACP) of FAS. The acetyl group is then transferred to the malonyl group, forming β-ketobutyryl-ACP and releasing $CO_2$.
2. The β-ketobutyryl-ACP undergoes reduction (via β-ketoacyl reductase) and dehydration (via β-hydroxyacyl dehydratase) to form a trans-monounsaturated fatty acyl group.
3. The double bond is reduced by NADPH, yielding a saturated fatty-acyl group two carbons longer than the initial one. The butyryl-group's ability to condense with a new malonyl group and repeat the elongation process is then regenerated.
4. When the fatty acyl group becomes 16 carbons long, a thioesterase activity hydrolyses it, releasing free palmitate.

Palmitate (16:0) is the precursor of longer chain saturated and unsaturated fatty acids (e.g., stearic (18:0), palmitoleic (16:1) and oleic (18:1) acids) through the action of elongases and desaturases present in the endoplasmic reticulum membrane. Palmitate and stearate are converted to their unsaturated derivatives, palmitoleic (16:1) and oleic (18:1) acids, respectively, by the action of a Δ9 desaturase.

Triacylglycerols (the primary storage unit for fatty acids) are formed by the esterification of two molecules of acyl-CoA to glycerol-3-phosphate to yield 1,2-diacylglycerol phosphate (commonly identified as phosphatidic acid) (FIG. 1). The phosphate is then removed, by phosphatidic acid phosphatase, to yield 1,2-diacylglycerol. Triacylglycerol is formed upon the addition of a third fatty acid, for example, by the action of a diacylglycerol-acyl transferase.

Biosynthesis of Omega Fatty Acids

Simplistically, the metabolic process that converts LA to GLA, DGLA and ARA (the ω-6 pathway) and ALA to STA, ETA, EPA, DPA and DHA (the ω-3 pathway) involves elongation of the carbon chain through the addition of two-carbon units and desaturation of the molecule through the addition of double bonds (FIG. 2). This requires a series of special desaturation and elongation enzymes present in the endoplasmic reticulum membrane.

ω-6 Fatty Acids

Oleic acid is converted to LA (18:2), the first of the ω-6 fatty acids, by the action of a Δ12 desaturase. Subsequent ω-6 fatty acids are produced as follows: 1.) LA is converted to GLA by the activity of a Δ6 desaturase; 2.) GLA is converted to DGLA by the action of an elongase; and 3.) DGLA is converted to ARA by the action of a Δ5 desaturase.

ω-3 Fatty Acids

Linoleic acid (LA) is converted to ALA, the first of the ω-3 fatty acids, by the action of a Δ15 desaturase. Subsequent ω-3 fatty acids are produced in a series of steps similar to that for the ω-6 fatty acids. Specifically: 1.) ALA is converted to STA by the activity of a Δ6 desaturase; 2.) STA is converted to ETA by the activity of an elongase; and 3.) ETA is converted to EPA by the activity of a Δ5 desaturase. Alternatively, ETA and EPA can be produced from DGLA and ARA, respectively, by the activity of a Δ17 desaturase. EPA can be further converted to DHA by the activity of an elongase and a Δ4 desaturase.

Genes Involved in Omega Fatty Acid Production

Many microorganisms, including algae, bacteria, molds and yeasts, can synthesize PUFAs and omega fatty acids in the ordinary course of cellular metabolism. Particularly well-studied are fungi including *Schizochytrium aggregatm*, species of the genus *Thraustochytrium* and *Morteriella alpina*. Additionally, many dinoflagellates (Dinophyceaae) naturally produce high concentrations of PUFAs. As such, a variety of genes involved in oil production have been identified through genetic means and the DNA sequences of some of these genes are publicly available (non-limiting examples are shown below in Table 2):

TABLE 2

Some Publicly Available Genes Involved in PUFA Production

| Genbank Accession No. | Description |
|---|---|
| AY131238 | *Argania spinosa* Δ6 desaturase |
| Y055118 | *Echium pitardii* var. *pitardii* Δ6 desaturase |
| AY055117 | *Echium gentianoides* Δ6 desaturase |
| AF296076 | *Mucor rouxii* Δ6 desaturase |
| AF007561 | *Borago officinalis* Δ6 desaturase |
| L11421 | *Synechocystis* sp. Δ6 desaturase |
| NM_031344 | *Rattus norvegicus* Δ6 fatty acid desaturase |
| AF465283, AF465281, AF110510 | *Mortierella alpina* Δ6 fatty acid desaturase |
| AF465282 | *Mortierella isabellina* Δ6 fatty acid desaturase |
| AF419296 | *Pythium irregulare* Δ6 fatty acid desaturase |
| AB052086 | *Mucor circinelloides* D6d mRNA for Δ6 fatty acid desaturase |
| AJ250735 | *Ceratodon purpureus* mRNA for Δ6 fatty acid desaturase |
| AF126799 | *Homo sapiens* Δ6 fatty acid desaturase |
| AF126798 | *Mus musculus* Δ6 fatty acid desaturase |
| AF199596, AF226273 | *Homo sapiens* Δ5 desaturase |
| AF320509 | *Rattus norvegicus* liver Δ5 desaturase |
| AB072976 | *Mus musculus* D5D mRNA for Δ5 desaturase |
| AF489588 | *Thraustochytrium* sp. ATCC21685 Δ5 fatty acid desaturase |
| AJ510244 | *Phytophthora megasperma* mRNA for Δ5 fatty acid desaturase |
| AF419297 | *Pythium irregulare* Δ5 fatty acid desaturase |
| AF07879 | *Caenorhabditis elegans* Δ5 fatty acid desaturase |
| AF067654 | *Mortierella alpina* Δ5 fatty acid desaturase |
| AB022097 | *Dictyostelium discoideum* mRNA for Δ5 fatty acid desaturase |
| AF489589.1 | *Thraustochytrium* sp. ATCC21685 Δ4 fatty acid desaturase |
| AX464731 | *Mortierella alpina* elongase gene (also WO 00/12720) |
| AAG36933 | *Emericella nidulans* oleate Δ12 desaturase |
| AF110509 | *Mortierella alpina* Δ12 fatty acid desaturase mRNA |
| AB020033 | *Mortierella alpina* mRNA for Δ12 fatty acid desaturase |
| AAL13300 | *Mortierella alpina* Δ12 fatty acid desaturase |
| AF417244 | *Mortierella alpina* ATCC 16266 Δ12 fatty acid desaturase gene |
| AF161219 | *Mucor rouxii* Δ12 desaturase mRNA |
| X86736 | *Spiruline platensis* Δ12 desaturase |
| AF240777 | *Caenorhabditis elegans* Δ12 desaturase |
| AB007640 | *Chlamydomonas reinhardtii* Δ12 desaturase |
| AB075526 | *Chlorella vulgaris* Δ12 desaturase |
| AP002063 | *Arabidopsis thaliana* microsomal Δ12 desaturase |
| AY332747 | *Pavlova lutheri* Δ4 fatty acid desaturase (des1) mRNA |
| NP_441622, BAA18302, BAA02924 | *Synechocystis* sp. PCC 6803 Δ15 desaturase |
| AAL36934 | *Perilla frutescens* Δ15 desaturase |
| AF338466 | *Acheta domesticus* Δ9 desaturase 3 mRNA |
| AF438199 | *Picea glauca* desaturase Δ9 (Des9) mRNA |
| E11368 | *Anabaena* Δ9 desaturase |
| E11367 | *Synechocystis* Δ9 desaturase |
| D83185 | *Pichia angusta* DNA for Δ9 fatty acid desaturase |
| U90417 | *Synechococcus vulcanus* Δ9 acyl-lipid fatty acid desaturase (desC) gene |
| AF085500 | *Mortierella alpina* Δ9 desaturase mRNA |
| AY504633 | *Emericella nidulans* Δ9 stearic acid desaturase (sdeB) gene |
| NM_069854 | *Caenorhabditis elegans* essential fatty acid desaturase, stearoyl-CoA desaturase (39.1 kD) (fat-6) complete mRNA |
| AF230693 | *Brassica oleracea* cultivar Rapid Cycling stearoyl-ACP desaturase (Δ9-BO-1) gene, exon sequence |

TABLE 2-continued

Some Publicly Available Genes Involved in PUFA Production

| Genbank Accession No. | Description |
|---|---|
| AX464731 | *Mortierella alpina* elongase gene (also WO 02/08401) |
| NM_119617 | *Arabidopsis thaliana* fatty acid elongase 1 (FAE1) (At4g34520) mRNA |
| NM_134255 | *Mus musculus* ELOVL family member 5, elongation of long chain fatty acids (yeast) (Elovl5), mRNA |
| NM_134383 | *Rattus norvegicus* fatty acid elongase 2 (rELO2), mRNA |
| NM_134382 | *Rattus norvegicus* fatty acid elongase 1 (rELO1), mRNA |
| NM_068396, NM_068392, NM_070713, NM_068746, NM_064685 | *Caenorhabditis elegans* fatty acid ELOngation (elo-6), (elo-5), (elo-2), (elo-3), and (elo-9) mRNA |

Additionally, the patent literature provides many additional DNA sequences of genes (and/or details concerning several of the genes above and their methods of isolation) involved in PUFA production. See, for example: U.S. Pat. No. 5,968,809 (Δ6 desaturases); U.S. Pat. No. 5,972,664 and U.S. Pat. No. 6,075,183 (Δ5 desaturases); WO 91/13972 and U.S. Pat. No. 5,057,419 (Δ9 desaturases); WO 93/11245 (Δ15 desaturases); U.S. 2003/0196217 A1 (Δ17 desaturases), WO 02/090493 (Δ4 desaturases); and WO 00/12720 and U.S. 2002/0139974A1 (elongases). Each of these patents and applications are herein incorporated by reference in their entirety.

Of particular interest herein are Δ12 desaturases, and more specifically, Δ12 desaturases that are suitable for expression in oleaginous yeast (e.g., *Yarrowia lipolytica*). A variety of sequences encoding fungal Δ12 fatty acid desaturases have been previously disclosed that could be used for heterologous expression in oleaginous *Yarrowia lipolytica* (e.g., GenBank Accession No's MG36933, AF110509, AAL13300, AF417244, AF161219 (supra)). Additionally, for example, the Δ12 fatty acid desaturases of *Glycine max, Brassica napus, Arabidopsis thaliana, Ricinus communis, Zea mays; Neurospora crassa* and *Botrytis cinerea* are disclosed in WO 94/11516, U.S. Pat. No. 5,443,974 and WO 03/099216.

Many factors affect the choice of a specific polypeptide having Δ12 desaturase activity that is to be expressed in a host cell for production of PUFAs (optionally in combination with other desaturases and elongases). Depending upon the host cell, the availability of substrate and the desired end product(s), several polypeptides are of interest; however, considerations for choosing a specific polypeptide having desaturase activity include the substrate specificity of the polypeptide, whether the polypeptide or a component thereof is a rate-limiting enzyme, whether the desaturase is essential for synthesis of a desired polyunsaturated fatty acid and/or cofactors required by the polypeptide. The expressed polypeptide preferably has parameters compatible with the biochemical environment of its location in the host cell. For example, the polypeptide may have to compete for substrate with other enzymes in the host cell. Analyses of the $K_M$ and specific activity of the polypeptide are therefore considered in determining the suitability of a given polypeptide for modifying PUFA production in a given host cell. The polypeptide used in a particular host cell is one that can function under the biochemical conditions present in the intended host cell, but otherwise can be any polypeptide having Δ12 desaturase activity capable of modifying the desired fatty acid (i.e., oleic acid). Thus, the sequences may be derived from any source, e.g., isolated from a natural source (from bacteria, algae, fungi, plants, animals, etc.), produced via a semi-synthetic route or synthesized de novo.

Sequence Identification of the *Yarrowia lipolytica* Δ12 Desaturase

Despite public disclosure of a variety of sequences encoding fungal Δ12 fatty acid desaturases (supra), expression of a native enzyme is preferred over a heterologous (or "foreign") enzyme since: 1.) the native enzyme is optimized for interaction with other enzymes and proteins within the cell; and 2.) heterologous genes are unlikely to share the same codon preference in the host organism. Additionally, advantages are incurred when the sequence of the native gene is known, as it permits facile disruption of the endogenous gene by targeted disruption.

Concerning disruption of a native Δ12 fatty acid desaturase gene, it may be useful for to engineer an oleaginous yeast that is not capable of producing PUFAs in some embodiments. Commercial applications where this lack of functionality would be desirable include the production of high value cocoa butter substitutes, oxidatively stable oils and specialty fatty acids derived from 18:1 (e.g., hydroxy- and epoxy-fatty acids). Alternatively, oleaginous yeast lacking Δ12 fatty acid desaturase activity could be utilized to produce "pure" ω-3 derivatives of ALA (e.g., STA, ETA, EPA, DPA, DHA) by transforming the organism with the appropriate genes (e.g., Δ6 desaturase, elongase, Δ5 desaturase, Δ4 desaturase) and feeding the organism ALA as a substrate; ω-6 fatty acids would not be synthesized under these conditions (see FIG. 2).

Thus, the Applicants sought to isolate a Δ12 fatty acid desaturase from *Yarrowia lipolytica*. Comparison of the Δ12 desaturase nucleotide base and deduced amino acid sequences to public databases reveals that the most similar known sequences are about 53% identical to the amino acid sequence of Δ12 desaturase reported herein (SEQ ID NO:24) over a length of 419 amino acids using a Clustal method of alignment (Thompson et. al., *Nucleic Acids Res.* 22:4673-4680 (1994)). More preferred amino acid fragments are at least about 70%-80% identical to the sequence herein, where those sequences that are 85%-90% identical are particularly suitable and those sequences that are about 95% identical are most preferred. Similarly, preferred Δ12 desaturase encoding nucleic acid sequences corresponding to the instant ORF are those encoding active proteins and which are at least about 70%-80% identical to the nucleic acid sequence of Δ12 desaturase reported herein, where those sequences that are 85%-90% identical are particularly suitable and those sequences that are about 95% identical are most preferred.

Isolation Of Homologs

The Δ12 desaturase nucleic acid fragment of the instant invention may be used to isolate genes encoding homologous proteins from the same or other bacterial, algal, fungal or plant species. Isolation of homologous genes using sequence-dependent protocols is well known in the art. Examples of sequence-dependent protocols include, but are not limited to: 1.) methods of nucleic acid hybridization; 2.) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci. USA* 82:1074 (1985); or strand displacement amplification (SDA), Walker, et al., *Proc. Natl. Acad. Sci. U.S.A.,* 89:392 (1992)]; and 3.) methods of library construction and screening by complementation.

For example, genes encoding similar proteins or polypeptides to the desaturase described herein could be isolated directly by using all or a portion of the instant nucleic acid fragments as DNA hybridization probes to screen libraries from any desired yeast or fungus using methodology well known to those skilled in the art (wherein those yeast or fungus producing LA and/or LA-derivatives would be preferred). Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan (e.g., random primers DNA labeling, nick translation or end-labeling techniques) or RNA probes using available in vitro transcription systems. In addition, specific primers can be designed and used to amplify a part of (or full-length of) the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art (Thein and Wallace, "The use of oligonucleotide as specific hybridization probes in the Diagnosis of Genetic Disorders", in *Human Genetic Diseases: A Practical Approach*, K. E. Davis Ed., (1986) pp 33-50, IRL: Herndon, Va.; and Rychlik, W., In *Methods in Molecular Biology*, White, B. A. Ed., (1993) Vol. 15, pp 31-39, PCR Protocols: Current Methods and Applications. Humania: Totowa, N.J.).

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL, Gaithersburg, Md.), specific 3' or 5' cDNA fragments can be isolated (Ohara et al., *PNAS USA* 86:5673 (1989); Loh et al., *Science* 243:217 (1989)).

In other embodiments, the instant desaturase sequences may be employed as hybridization reagents for the identification of homologs. The basic components of a nucleic acid hybridization test include a probe, a sample suspected of containing the gene or gene fragment of interest and a specific hybridization method. Probes of the present invention are typically single-stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions that will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration, the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143-5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide and cesium trifluoroacetate, among others. Typically, the chaotropic agent will be present at a final concentration of about 3 M. If desired, one can add formamide to the hybridization mixture, typically 30-50% (v/v).

Various hybridization solutions can be employed. Typically, these comprise from about 20 to 60% volume, preferably 30%, of a polar organic solvent. A common hybridization solution employs about 30-50% v/v formamide, about 0.15 to 1 M sodium chloride, about 0.05 to 0.1 M buffers (e.g., sodium citrate, Tris-HCl, PIPES or HEPES (pH range about 6-9)), about 0.05 to 0.2% detergent (e.g., sodium dodecylsulfate), or between 0.5-20 mM EDTA, FICOLL (Pharmacia Inc.) (about 300-500 kdal), polyvinylpyrrolidone (about 250-500 kdal) and serum albumin. Also included in the typical hybridization solution will be unlabeled carrier nucleic acids from about 0.1 to 5 mg/mL, fragmented nucleic DNA (e.g., calf thymus or salmon sperm DNA, or yeast RNA), and optionally from about 0.5 to 2% wt/vol glycine. Other additives may also be included, such as volume exclusion agents that include a variety of polar water-soluble or swellable agents (e.g., polyethylene glycol), anionic polymers (e.g., polyacrylate or polymethylacrylate) and anionic saccharidic polymers (e.g., dextran sulfate).

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Availability of the instant nucleotide and deduced amino acid sequences facilitates immunological screening of DNA expression libraries. Synthetic peptides representing portions of the instant amino acid sequence may be synthesized. These peptides can be used to immunize animals to produce polyclonal or monoclonal antibodies with specificity for peptides or proteins comprising the amino acid sequences. These antibodies can be then be used to screen DNA expression libraries to isolate full-length DNA clones of interest (Lerner, R. A. *Adv. Immunol.* 36:1 (1984); Maniatis, supra).

Gene Optimization for Improved Heterologous Expression

A variety of techniques can be utilized to improve the expression of the Δ12 desaturase in an alternate host. Two such techniques include codon-optimization and mutagenesis of the gene.

Codon Optimization

In some embodiments, it may be desirable to modify a portion of the codons encoding the Δ12 desaturase polypeptide, for example, to enhance the expression of the gene encoding that polypeptide in an alternate host (e.g., an oleaginous yeast other than *Yarrowia lipolytica*).

In general, host preferred codons can be determined within a particular host species of interest by examining codon usage in proteins (preferably those proteins expressed in the largest amount) and determining which codons are used with highest frequency. Then, the coding sequence for the polypeptide of interest having desaturase activity can be synthesized in whole or in part using the codons preferred in the host species. All (or portions) of the DNA also can be synthesized to remove any destabilizing sequences or regions of secondary structure that would be present in the transcribed mRNA. All (or portions) of the DNA also can be synthesized to alter the base composition to one more preferable in the desired host cell.

Mutagenesis

Methods for synthesizing sequences and bringing sequences together are well established in the literature. For example, in vitro mutagenesis and selection, site-directed mutagenesis, error prone PCR (Melnikov et al., *Nucleic Acids Research*, 27(4):1056-1062 (Feb. 15, 1999)), "gene shuffling" (U.S. Pat. Nos. 5,605,793; 5,811,238; 5,830,721; and 5,837,458) or other means can be employed to obtain mutations of naturally occurring desaturase genes, such as the Δ12 desaturase described herein. This would permit production of a polypeptide having desaturase activity in vivo with more desirable physical and kinetic parameters for function in the host cell (e.g., a longer half-life or a higher rate of production of a desired PUFA).

If desired, the regions of a desaturase polypeptide important for enzymatic activity can be determined through routine mutagenesis, expression of the resulting mutant polypeptides and determination of their activities. Mutants may include deletions, insertions and point mutations, or combinations thereof. A typical functional analysis begins with deletion mutagenesis to determine the N- and C-terminal limits of the protein necessary for function, and then internal deletions, insertions or point mutants are made to further determine regions necessary for function. Other techniques such as cassette mutagenesis or total synthesis also can be used. Deletion mutagenesis is accomplished, for example, by using exonucleases to sequentially remove the 5' or 3' coding regions. Kits are available for such techniques. After deletion, the coding region is completed by ligating oligonucleotides containing start or stop codons to the deleted coding region after the 5' or 3' deletion, respectively. Alternatively, oligonucleotides encoding start or stop codons are inserted into the coding region by a variety of methods including site-directed mutagenesis, mutagenic PCR or by ligation onto DNA digested at existing restriction sites. Internal deletions can similarly be made through a variety of methods including the use of existing restriction sites in the DNA, by use of mutagenic primers via site-directed mutagenesis or mutagenic PCR. Insertions are made through methods such as linker-scanning mutagenesis, site-directed mutagenesis or mutagenic PCR. Point mutations are made through techniques such as site-directed mutagenesis or mutagenic PCR.

Chemical mutagenesis also can be used for identifying regions of a desaturase polypeptide important for activity. A mutated construct is expressed, and the ability of the resulting altered protein to function as a desaturase is assayed. Such structure-function analysis can determine which regions may be deleted, which regions tolerate insertions, and which point mutations allow the mutant protein to function in substantially the same way as the native desaturase. All such mutant proteins and nucleotide sequences encoding them that are derived from the desaturase described herein are within the scope of the present invention.

Thus, the present invention comprises the complete sequence of the Δ12 desaturase as reported in the accompanying Sequence Listing, the complement of that complete sequence, substantial portions of that sequence, codon-optimized desaturases derived therefrom and those sequences that are substantially homologous thereto.

Microbial Production of ω-3 and/or ω-6 Fatty Acids

Microbial production of ω-3 and/or ω-6 fatty acids has several advantages over purification from natural sources such as fish or plants. For example:

1.) Many microbes are known with greatly simplified oil compositions compared with those of higher organisms, making purification of desired components easier;
2.) Microbial production is not subject to fluctuations caused by external variables, such as weather and food supply;
3.) Microbially produced oil is substantially free of contamination by environmental pollutants;
4.) Microbes can provide PUFAs in particular forms which may have specific uses; and
5.) Microbial oil production can be manipulated by controlling culture conditions, notably by providing particular substrates for microbially expressed enzymes, or by addition of compounds or genetic engineering approaches to suppress undesired biochemical pathways.

In addition to these advantages, production of ω-3 and/or ω-6 fatty acids from recombinant microbes provides the ability to alter the naturally occurring microbial fatty acid profile by providing new biosynthetic pathways in the host or by suppressing undesired pathways, thereby increasing levels of desired PUFAs (or conjugated forms thereof) and decreasing levels of undesired PUFAs (see co-pending U.S. Provisional Application 60/468,677, herein incorporated entirely by reference).

Methods for Production of Various ω-3 and/or ω-6 Fatty Acids

It is expected that introduction of chimeric genes encoding the Δ12 desaturase described herein, under the control of appropriate promoters will result in increased production of LA. As such, the present invention encompasses a method for the direct production of PUFAs comprising exposing a fatty acid substrate (i.e., oleic acid) to the PUFA enzyme described herein (i.e., the Δ12 desaturase), such that the substrate is converted to the desired fatty acid product (i.e., LA).

Alternatively, the PUFA gene and its corresponding enzyme product described herein can be used indirectly for the production of PUFAs. Indirect production of PUFAs occurs wherein the fatty acid substrate is converted indirectly into the desired fatty acid product, via means of an intermediate step(s) or pathway intermediate(s). Thus, it is contemplated that the Δ12 desaturase described herein may be expressed in conjunction with one or more genes that encode other enzymes, such that a series of reactions occur to produce a desired product. In a preferred embodiment, for example, a host organism may be co-transformed with a vector comprising additional genes encoding enzymes of the PUFA biosynthetic pathway to result in higher levels of production of ω-3 and/or ω-6 fatty acids (e.g., GLA, DGLA, ARA, ALA, STA, ETA, EPA, DPA and DNA). Specifically, for example, it may be desirable to overexpress the Δ12 desaturase described herein in host cells that are also expressing: 1.) a gene encoding a Δ6 desaturase for the overproduction of GLA; 2.) an expression cassette comprising genes encoding a Δ6 desaturase and a high-affinity elongase for the overproduction of DGLA; 3.) genes encoding a Δ6 desaturase, high-affinity elongase and Δ5 desaturase for the overproduction of ARA; or 4.) genes encoding a Δ6 desaturase, high-affinity elongase, Δ5 desaturase and Δ17 desaturase for the overproduction of EPA. In alternate embodiments, it may be desirable to overexpress the Δ12 desaturase as described herein in cells that are also expressing: 1.) a gene encoding a Δ15 desaturase for the overproduction of ALA; 2.) genes encoding a Δ15 desaturase and Δ6 desaturase for the overproduction of STA; 3.) genes encoding a Δ15 desaturase, Δ16 desaturase and a high-affinity elongase for the overproduction of ETA; or 4.) genes encoding a Δ15 desaturase, Δ6 desaturase, high-affinity elongase and Δ5 desaturase for the overproduction of EPA. As is well known to one skilled in the art, various other combinations of the following enzymatic activities may be useful to express in a host in conjunction with the desaturase herein: a Δ15 desaturase, a Δ4 desaturase, a Δ5 desaturase, a Δ6 desaturase, a Δ17 desaturase, a Δ9 desaturase and/or an elongase (see FIG. 2). The particular genes included within a particular expression cassette will depend on the host cell (and its PUFA profile and/or desaturase profile), the availability of substrate and the desired end product(s).

In alternate embodiments, it may be useful to disrupt a host organism's native Δ12 desaturase, based on the complete sequences described herein, the complement of those complete sequences, substantial portions of those sequences, codon-optimized desaturases derived therefrom and those sequences that are substantially homologous thereto. For example, the targeted disruption of the Δ12 desaturase described herein in *Yarrowia lipolytica* produces a mutant strain that is unable to synthesize LA. This mutant strain could be useful for: 1.) production of other specialty oils (e.g., high value cocoa butter substitutes, oxidatively stable oils and fatty acids derived from 18:1 such as hydroxy- and epoxy-fatty acids); or 2.) production of "pure" ω-3 fatty acid derivatives of ALA, when the host cells are grown on e.g., ALA (without co-synthesis of ω-6 fatty acids).

Expression Systems, Cassettes and Vectors

The gene and gene product of the instant sequences described herein may be produced in various microbial host cells, particularly in the cells of oleaginous yeasts (e.g., *Yarrowia lipolytica*). Expression in recombinant microbial hosts may be useful for the production of various PUFA pathway intermediates, or for the modulation of PUFA pathways already existing in the host for the synthesis of new products heretofore not possible using the host.

Microbial expression systems and expression vectors containing regulatory sequences that direct high level expression of foreign proteins are well known to those skilled in the art. Any of these could be used to construct chimeric genes for production of any of the gene products of the instant sequences. These chimeric genes could then be introduced into appropriate microorganisms via transformation to provide high-level expression of the encoded enzymes.

Vectors or DNA cassettes useful for the transformation of suitable host cells are well known in the art. The specific choice of sequences present in the construct is dependent upon the desired expression products (supra), the nature of the host cell and the proposed means of separating transformed cells versus non-transformed cells. Typically, however, the vector or cassette contains sequences directing transcription and translation of the relevant gene(s), a selectable marker and sequences allowing autonomous replication or chromosomal integration. Suitable vectors comprise a region 5' of the gene that controls transcriptional initiation and a region 3' of the DNA fragment that controls transcriptional termination. It is most preferred when both control regions are derived from genes from the transformed host cell, although it is to be understood that such control regions need not be derived from the genes native to the specific species chosen as a production host.

Initiation control regions or promoters which are useful to drive expression of the instant ORF in the desired host cell are numerous and familiar to those skilled in the art. Virtually any promoter capable of directing expression of this gene in the selected host cell is suitable for the present invention. Expression in a host cell can be accomplished in a transient or stable fashion. Transient expression can be accomplished by inducing the activity of a regulatable promoter operably linked to the gene of interest. Stable expression can be achieved by the use of a constitutive promoter operably linked to the gene of interest. As an example, when the host cell is yeast, transcriptional and translational regions functional in yeast cells are provided, particularly from the host species. The transcriptional initiation regulatory regions can be obtained, for example, from: 1.) genes in the glycolytic pathway, such as alcohol dehydrogenase, glyceraldehyde-3-phosphate-dehydrogenase (see U.S. Patent Application No. 60/482,263), phosphoglycerate mutase (see U.S. Patent Application No. 60/482,263), fructose-bisphosphate aldolase (see U.S. Patent Application No. 60/519,971), phosphoglucose-isomerase, phosphoglycerate kinase, etc.; or, 2.) regulatable genes such as acid phosphatase, lactase, metallothionein, glucoamylase, the translation elongation factor EF1-α (TEF) protein (U.S. Pat. No. 6,265,185), ribosomal protein S7 (U.S. Pat. No. 6,265,185), etc. Any one of a number of regulatory sequences can be used, depending upon whether constitutive or induced transcription is desired, the efficiency of the promoter in expressing the ORF of interest, the ease of construction and the like.

Nucleotide sequences surrounding the translational initiation codon 'ATG' have been found to affect expression in yeast cells. If the instant desaturase is poorly expressed in non-*Yarrowia lipolytica* yeast, the nucleotide sequences of exogenous genes can be modified to include an efficient yeast translation initiation sequence to obtain optimal gene expression. For expression in yeast, this can be done by site-directed mutagenesis of an inefficiently expressed gene by fusing it in-frame to an endogenous yeast gene, preferably a highly expressed gene. Alternatively, one can determine the consensus translation initiation sequence in the host and engineer this sequence into heterologous genes for their optimal expression in the host of interest.

The termination region can be derived from the 3' region of the gene from which the initiation region was obtained or from a different gene. A large number of termination regions are known and function satisfactorily in a variety of hosts (when utilized both in the same and different genera and species from where they were derived). The termination region usually is selected more as a matter of convenience rather than because of any particular property. Preferably, the termination region is derived from a yeast gene, particularly *Saccharomyces, Schizosaccharomyces, Candida, Yarrowia* or

*Kluyveromyces*. The 3'-regions of mammalian genes encoding γ-interferon and α-2 interferon are also known to function in yeast. Termination control regions may also be derived from various genes native to the preferred hosts. Optionally, a termination site may be unnecessary; however, it is most preferred if included.

As one of skill in the art is aware, merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, some of the molecular features that have been manipulated to control gene expression include: 1.) the nature of the relevant transcriptional promoter and terminator sequences; 2.) the number of copies of the cloned gene and whether the gene is plasmid-borne or integrated into the genome of the host cell; 3.) the final cellular location of the synthesized foreign protein; 4.) the efficiency of translation in the host organism; 5.) the intrinsic stability of the cloned gene protein within the host cell; and 6.) the codon usage within the cloned gene, such that its frequency approaches the frequency of preferred codon usage of the host cell. Each of these types of modifications are encompassed in the present invention, as means to further optimize expression of the Δ12 desaturase described herein.

Transformation of Microbial Hosts

Once the DNA encoding a polypeptide suitable for expression in an oleaginous yeast has been obtained, it is placed in a plasmid vector capable of autonomous replication in a host cell, or it is directly integrated into the genome of the host cell. Integration of expression cassettes can occur randomly within the host genome or can be targeted through the use of constructs containing regions of homology with the host genome sufficient to target recombination within the host locus. Where constructs are targeted to an endogenous locus, all or some of the transcriptional and translational regulatory regions can be provided by the endogenous locus.

Where two or more genes are expressed from separate replicating vectors, it is desirable that each vector has a different means of selection and should lack homology to the other construct(s) to maintain stable expression and prevent reassortment of elements among constructs. Judicious choice of regulatory regions, selection means and method of propagation of the introduced construct(s) can be experimentally determined so that all introduced genes are expressed at the necessary levels to provide for synthesis of the desired products.

Constructs comprising the gene of interest may be introduced into a host cell by any standard technique. These techniques include transformation (e.g., lithium acetate transformation [*Methods in Enzymology*, 194:186-187 (1991)]), protoplast fusion, biolistic impact, electroporation, microinjection, or any other method that introduces the gene of interest into the host cell. More specific teachings applicable for oleaginous yeasts (i.e., *Yarrowia lipolytica*) include U.S. Pat. Nos. 4,880,741 and 5,071,764 and Chen, D. C. et al. (*Appl Microbiol Biotechnol.* 48(2):232-235 (1997)).

For convenience, a host cell that has been manipulated by any method to take up a DNA sequence (e.g., an expression cassette) will be referred to as "transformed" or "recombinant" herein. The transformed host will have at least one copy of the expression construct and may have two or more, depending upon whether the gene is integrated into the genome, amplified, or is present on an extrachromosomal element having multiple copy numbers. The transformed host cell can be identified by selection for a marker contained on the introduced construct. Alternatively, a separate marker construct may be co-transformed with the desired construct, as many transformation techniques introduce many DNA molecules into host cells. Typically, transformed hosts are selected for their ability to grow on selective media. Selective media may incorporate an antibiotic or lack a factor necessary for growth of the untransformed host, such as a nutrient or growth factor. An introduced marker gene may confer antibiotic resistance, or encode an essential growth factor or enzyme, thereby permitting growth on selective media when expressed in the transformed host. Selection of a transformed host can also occur when the expressed marker protein can be detected, either directly or indirectly. The marker protein may be expressed alone or as a fusion to another protein. The marker protein can be detected by: 1.) its enzymatic activity (e.g., β-galactosidase can convert the substrate X-gal [5-bromo-4-chloro-3-indolyl-β-D-galactopyranoside] to a colored product; luciferase can convert luciferin to a light-emitting product); or 2.) its light-producing or modifying characteristics (e.g., the green fluorescent protein of *Aequorea victoria* fluoresces when illuminated with blue light). Alternatively, antibodies can be used to detect the marker protein or a molecular tag on, for example, a protein of interest. Cells expressing the marker protein or tag can be selected, for example, visually, or by techniques such as FACS or panning using antibodies. For selection of yeast transformants, any marker that functions in yeast may be used. Desirably, resistance to kanamycin, hygromycin and the amino glycoside G418 are of interest, as well as ability to grow on media lacking uracil or leucine.

Following transformation, substrates suitable for the instant Δ12 desaturase (and optionally other PUFA enzymes that are co-expressed within the host cell) may be produced by the host either naturally or transgenically, or they may be provided exogenously.

Metabolic Engineering of ω-3 and/or ω-6 Fatty Acid Biosynthesis in Microbes

Knowledge of the sequence of the present Δ12 desaturase will be useful for manipulating ω-3 and/or ω-6 fatty acid biosynthesis in oleaginous yeasts, and particularly, in *Yarrowia lipolytica*. This may require metabolic engineering directly within the PUFA biosynthetic pathway or additional manipulation of pathways that contribute carbon to the PUFA biosynthetic pathway. Methods useful for manipulating biochemical pathways are well known to those skilled in the art.

Techniques to Up-Regulate Desirable Biosynthetic Pathways

Additional copies of desaturase and elongase genes may be introduced into the host to increase the output of the ω-3 and/or ω-6 fatty acid biosynthetic pathways, typically through the use of multicopy plasmids. Expression of the desaturase or elongase genes also can be increased at the transcriptional level through the use of a stronger promoter (either regulated or constitutive) to cause increased expression, by removing/deleting destabilizing sequences from either the mRNA or the encoded protein, or by adding stabilizing sequences to the mRNA (U.S. Pat. No. 4,910,141). Yet another approach to increase expression of heterologous desaturase or elongase genes is to increase the translational efficiency of the encoded mRNAs by replacement of codons in the native gene with those for optimal gene expression in the selected host microorganism.

Techniques to Down-Regulate Undesirable Biosynthetic Pathways

Conversely, biochemical pathways competing with the ω-3 and/or ω-6 fatty acid-biosynthetic pathways for energy or carbon, or native PUFA biosynthetic pathway enzymes that interfere with production of a particular PUFA end-product, may be eliminated by gene disruption or down-regulated by other means (e.g., antisense mRNA). For gene disruption, a foreign DNA fragment (typically a selectable marker gene) is inserted into the structural gene to be disrupted in order to interrupt its coding sequence and thereby functionally inactivate the gene. Transformation of the disruption cassette into the host cell results in replacement of the functional native gene by homologous recombination with the non-functional disrupted gene (see, for example: Hamilton et al. *J. Bacteriol.* 171:4617-4622 (1989); Balbas et al. *Gene* 136:211-213 (1993); Gueldener et al. *Nucleic Acids Res.* 24:2519-2524 (1996); and Smith et al. *Methods Mol. Cell. Biol.* 5:270-277 (1996)).

Antisense technology is another method of down-regulating genes when the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of anti-sense genes may require the use of different chimeric genes utilizing different regulatory elements known to the skilled artisan.

Although targeted gene disruption and antisense technology offer effective means of down-regulating genes where the sequence is known, other less specific methodologies have been developed that are not sequence-based. For example, cells may be exposed to UV radiation and then screened for the desired phenotype. Mutagenesis with chemical agents is also effective for generating mutants and commonly used substances include chemicals that affect nonreplicating DNA (e.g., $HNO_2$ and $NH_2OH$), as well as agents that affect replicating DNA (e.g., acridine dyes, notable for causing frameshift mutations). Specific methods for creating mutants using radiation or chemical agents are well documented in the art. See, for example: Thomas D. Brock in *Biotechnology: A Textbook of Industrial Microbiology*, 2$^{nd}$ ed. (1989) Sinauer Associates: Sunderland, Mass.; or Deshpande, Mukund V., *Appl. Biochem. Biotechnol.*, 36:227 (1992).

Another non-specific method of gene disruption is the use of transposable elements or transposons. Transposons are genetic elements that insert randomly into DNA but can be later retrieved on the basis of sequence to determine where the insertion has occurred. Both in vivo and in vitro transposition methods are known. Both methods involve the use of a transposable element in combination with a transposase enzyme. When the transposable element or transposon is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available [see, for example: 1.) The Primer Island Transposition Kit, available from Perkin Elmer Applied Biosystems, Branchburg, N.J., based upon the yeast Ty1 element; 2.) The Genome Priming System, available from New-England Biolabs, Beverly, Mass., based upon the bacterial transposon Tn7; and 3.) The EZ::TN Transposon Insertion Systems, available from Epicentre Technologies, Madison, Wis., based upon the Tn5 bacterial transposable element].

Within the context of the present invention, it may be useful to modulate the expression of the fatty acid biosynthetic pathway by any one of the methods described above. For example, the present invention provides a gene (i.e., a Δ12 desaturase) encoding a key enzyme in the biosynthetic pathway leading to the production of ω-3 and/or ω-6 fatty acids. It will be particularly useful to express this gene in oleaginous yeasts that produce insufficient amounts of 18:2 fatty acids and to modulate the expression of this and other PUFA biosynthetic genes to maximize production of preferred PUFA products using various means for metabolic engineering of the host organism. Likewise, to maximize PUFA production with this gene, it may be necessary to disrupt pathways that compete for the carbon flux directed toward PUFA biosynthesis. In alternate embodiments, it may be desirable to disrupt the Δ12 desaturase herein, to promote synthesis of ω-3 fatty acids while simultaneously preventing co-synthesis of ω-6 fatty acids. In another alternate embodiment it will be possible to regulate the production of ω-3/ω-6 fatty acids by placing the present Δ12 desaturase gene under the control of inducible or regulated promoters.

Preferred Microbial Hosts for Recombinant Expression of Δ12 Desaturase

Host cells for expression of the instant gene and nucleic acid fragments may include microbial hosts that grow on a variety of feedstocks, including simple or complex carbohydrates, organic acids and alcohols, and/or hydrocarbons over a wide range of temperature and pH values. Although the genes described in the instant invention have been isolated for expression in oleaginous yeast, it is contemplated that because transcription, translation and the protein biosynthetic apparatus is highly conserved, any bacteria, yeast, algae and/or filamentous fungus will be a suitable host for expression of the present nucleic acid fragments.

Preferred microbial hosts are oleaginous organisms, such as oleaginous yeasts. These oleaginous organisms are naturally capable of oil synthesis and accumulation, wherein the oil can comprise greater than about 25% of the cellular dry weight, more preferably greater than about 30% of the cellular dry weight, and most preferably greater than about 40% of the cellular dry weight. Genera typically identified as oleaginous yeast include, but are not limited to: *Yarrowia, Mortierella, Candida, Rhodotorula, Rhodosporidium, Cryptococcus, Trichosporon* and *Lipomyces*. More specifically, illustrative oil-synthesizing yeasts include: *Rhodosporidium toruloides, Lipomyces starkeyii, L. lipoferus, Candida revkaufi, C. pulcherrima, C. tropicalis, C. utilis, Trichosporon pullans, T. cutaneum, Rhodotorula glutinus, R. graminis, Mortierella alpina* and *Yarrowia lipolytica* (formerly classified as *Candida lipolytica*).

Most preferred is the oleaginous yeast *Yarrowia lipolytica*; and, in a further embodiment, most preferred are the *Y. lipolytica* strains designated as ATCC #20362, ATCC #8862, ATCC #18944, ATCC #76982 and/or LGAM S(7)1 (Papanikolaou S., and Aggelis G., *Bioresour. Technol.* 82(1):43-9 (2002)).

Fermentation Processes for PUFA Production

The transformed microbial host cell is grown under conditions that optimize activity of fatty acid biosynthetic genes and produce the greatest and the most economical yield of fatty acids (e.g., LA, which can in turn increase the production of various ω-3 and/or ω-6 fatty acids). In general, media conditions that may be optimized include the type and amount of carbon source, the type and amount of nitrogen source, the carbon-to-nitrogen ratio, the oxygen level, growth temperature, pH, length of the biomass production phase, length of the oil accumulation phase and the time of cell harvest. Microorganisms of interest, such as oleaginous yeast, are grown in complex media (e.g., yeast extract-peptone-dextrose broth (YPD)) or a defined minimal media that lacks a component necessary for growth and thereby forces selection of the desired expression cassettes (e.g., Yeast Nitrogen Base (DIFCO Laboratories, Detroit, Mich.)).

Fermentation media in the present invention must contain a suitable carbon source. Suitable carbon sources may include, but are not limited to: monosaccharides (e.g., glucose, fructose), disaccharides (e.g., lactose, sucrose), oligosaccharides, polysaccharides (e.g., starch, cellulose or mixtures thereof), sugar alcohols (e.g., glycerol) or mixtures from renewable feedstocks (e.g., cheese whey permeate, cornsteep liquor, sugar beet molasses, barley malt). Additionally, carbon sources may include alkanes, fatty acids, esters of fatty acids, monoglycerides, diglycerides, triglycerides, phospholipids and various commercial sources of fatty acids including vegetable oils (e.g., soybean oil) and animal fats. Additionally, the carbon substrate may include one-carbon substrates (e.g., carbon dioxide or methanol) for which metabolic conversion into key biochemical intermediates has been demonstrated. Hence it is contemplated that the source of carbon utilized in the present invention may encompass a wide variety of carbon-containing substrates and will only be limited by the choice of the host organism. Although all of the above mentioned carbon substrates and mixtures thereof are expected to be suitable in the present invention, preferred carbon substrates are sugars and/or fatty acids. Most preferred is glucose and/or fatty acids containing between 10-22 carbons.

Nitrogen may be supplied from an inorganic (e.g., $(NH_4)_2SO_4$) or organic source (e.g., urea or glutamate). In addition to appropriate carbon and nitrogen sources, the fermentation media must also contain suitable minerals, salts, cofactors, buffers, vitamins, and other components known to those skilled in the art suitable for the growth of the microorganism and promotion of the enzymatic pathways necessary for PUFA production. Particular attention is given to several metal ions (e.g., $Mn^{+2}$, $Co^{+2}$, $Zn^{+2}$, $Mg^{+2}$) that promote synthesis of lipids and PUFAs (Nakahara, T. et al., *Ind. Appl. Single Cell Oils*, D. J. Kyle and R. Colin, eds. pp 61-97 (1992)).

Preferred growth media in the present invention are common commercially prepared media, such as Yeast Nitrogen Base (DIFCO Laboratories, Detroit, Mich.). Other defined or synthetic growth media may also be used and the appropriate medium for growth of the particular microorganism will be known by one skilled in the art of microbiology or fermentation science. A suitable pH range for the fermentation is typically between about pH 4.0 to pH 8.0, wherein pH 5.5 to pH 7.0 is preferred as the range for the initial growth conditions. The fermentation may be conducted under aerobic or anaerobic conditions, wherein microaerobic conditions are preferred.

Typically, accumulation of high levels of PUFAs in oleaginous yeast cells requires a two-stage process, since the metabolic state must be "balanced" between growth and synthesis/storage of fats. Thus, most preferably, a two-stage fermentation process is necessary for the production of PUFAs in oleaginous yeast. In this approach, the first stage of the fermentation is dedicated to the generation and accumulation of cell mass and is characterized by rapid cell growth and cell division. In the second stage of the fermentation, it is preferable to establish conditions of nitrogen deprivation in the culture to promote high levels of lipid accumulation. The effect of this nitrogen deprivation is to reduce the effective concentration of AMP in the cells, thereby reducing the activity of the NAD-dependent isocitrate dehydrogenase of mitochondria. When this occurs, citric acid will accumulate, thus forming abundant pools of acetyl-CoA in the cytoplasm and priming fatty acid synthesis. Thus, this phase is characterized by the cessation of cell division followed by the synthesis of fatty acids and accumulation of oil.

Although cells are typically grown at about 30° C., some studies have shown increased synthesis of unsaturated fatty acids at lower temperatures (Yongmanitchai and Ward, *Appl. Environ. Microbiol.* 57:419-25 (1991)). Based on process economics, this temperature shift should likely occur after the first phase of the two-stage fermentation, when the bulk of the organisms' growth has occurred.

It is contemplated that a variety of fermentation process designs may be applied, where commercial production of omega fatty acids using the instant Δ12 desaturase is desired. For example, commercial production of PUFAs from a recombinant microbial host may be produced by a batch, fed-batch or continuous fermentation process.

A batch fermentation process is a closed system wherein the media-composition is set at the beginning of the process and not subject to further additions beyond those required for maintenance of pH and oxygen level during the process. Thus, at the beginning of the culturing process the media is inoculated with the desired organism and growth or metabolic activity is permitted to occur without adding additional substrates (i.e., carbon and nitrogen sources) to the medium. In batch processes the metabolite and biomass compositions of the system change constantly up to the time the culture is terminated. In a typical batch process, cells proceed through a static lag phase to a high-growth log phase and finally to a stationary phase, wherein the growth rate is diminished or halted. Left untreated, cells in the stationary phase will eventually die. A variation of the standard batch process is the fed-batch process, wherein the substrate is continually added to the fermentor over the course of the fermentation process. A fed-batch process is also suitable in the present invention. Fed-batch processes are useful when catabolite repression is apt to inhibit the metabolism of the cells or where it is desirable to have limited amounts of substrate in the media at any one time. Measurement of the substrate concentration in fed-batch systems is difficult and therefore may be estimated on the basis of the changes of measurable factors such as pH, dissolved oxygen and the partial pressure of waste gases (e.g., $CO_2$). Batch and fed-batch culturing methods are common and well known in the art and examples may be found in Thomas D. Brock in *Biotechnology: A Textbook of Industrial Microbiology*, $2^{nd}$ ed., (1989) Sinauer Associates: Sunderland, Mass.; or Deshpande, Mukund V., *Appl. Biochem. Biotechnol.*, 36:227 (1992), herein incorporated by reference.

Commercial production of omega fatty acids using the instant Δ12 desaturase may also be accomplished by a continuous fermentation process wherein a defined media is continuously added to a bioreactor while an equal amount of culture volume is removed simultaneously for product recovery. Continuous cultures generally maintain the cells in the log phase of growth at a constant cell density. Continuous or semi-continuous culture methods permit the modulation of one factor or any number of factors that affect cell growth or end product concentration. For example, one approach may limit the carbon source and allow all other parameters to moderate metabolism. In other systems, a number of factors affecting growth may be altered continuously while the cell concentration, measured by media turbidity, is kept constant. Continuous systems strive to maintain steady state growth and thus the cell growth rate must be balanced against cell loss due to media being drawn off the culture. Methods of modulating nutrients and growth factors for continuous culture processes, as well as techniques for maximizing the rate of product formation, are well known in the art of industrial microbiology and a variety of methods are detailed by Brock, supra.

Purification of PUFAs

The PUFAs may be found in the host microorganism as free fatty acids or in esterified forms such as acylglycerols, phospholipids, sulfolipids or glycolipids, and may be extracted from the host cell through a variety of means well-known in the art. One review of extraction techniques, quality analysis and acceptability standards for yeast lipids is that of Z. Jacobs (*Critical Reviews in Biotechnology* 12(5/6):463-491 (1992)). A brief review of downstream processing is also available by A. Singh and O. Ward (*Adv. Appl. Microbiol.* 45:271-312 (1997)).

In general, means for the purification of PUFAs may include extraction with organic solvents, sonication, supercritical fluid extraction (e.g., using carbon dioxide), saponification and physical means such as presses, or combinations thereof. Of particular interest is extraction with methanol and chloroform in the presence of water (E. G. Bligh & W. J. Dyer, *Can. J. Biochem. Physiol.* 37:911-917 (1959)). Where desirable, the aqueous layer can be acidified to protonate negatively-charged moieties and thereby increase partitioning of desired products into the organic layer. After extraction, the organic solvents can be removed by evaporation under a stream of nitrogen. When isolated in conjugated forms, the products may be enzymatically or chemically cleaved to release the free fatty acid or a less complex conjugate of interest, and can then be subject to further manipulations to produce a desired end product. Desirably, conjugated forms of fatty acids are cleaved with potassium hydroxide.

If further purification is necessary, standard methods can be employed. Such methods may include extraction, treatment with urea, fractional crystallization, HPLC, fractional distillation, silica gel chromatography, high-speed centrifugation or distillation, or combinations of these techniques. Protection of reactive groups, such as the acid or alkenyl groups, may be done at any step through known techniques (e.g., alkylation, iodination). Methods used include methylation of the fatty acids to produce methyl esters. Similarly, protecting groups may be removed at any step. Desirably, purification of fractions containing GLA, STA, ARA, DHA and EPA may be accomplished by treatment with urea and/or fractional distillation.

DESCRIPTION OF PREFERRED EMBODIMENTS

The ultimate goal of the work described herein is the development of an oleaginous yeast that accumulates oils enriched in ω-3 and/or ω-6 PUFAs. Toward this end, Δ12 desaturases must be identified that function efficiently in oleaginous yeasts, to enable synthesis and high accumulation of preferred PUFAs in these hosts. Identification of efficient Δ12 desaturases is also necessary to manipulate the ratio of ω-3 to ω-6 PUFAs produced in host cells.

In the present invention, Applicants have isolated and cloned the only gene in *Yarrowia lipolytica* that encodes a Δ12 desaturase enzyme. Confirmation of this gene's activity was provided based upon: 1.) the lack of detectable LA in a strain wherein disruption of the native Δ12 desaturase by targeted gene replacement through homologous recombination had occurred (Example 2); 2.) restoration of LA biosynthesis (complementation) in the disrupted strain upon transformation with the chimeric gene (Example 4); and 3.) the overproduction of LA in wild type cells upon transformation with the chimeric gene (Example 4). Thus, this Δ12 desaturase gene is useful for expression in various microbial hosts, and particularly for overexpression in oleaginous yeasts (e.g., the native host *Yarrowia lipolytica*). Additional benefits may result since expression of the Δ12 desaturase can also be put under the control of strong constitutive or regulated promoters that do not have the regulatory constraints of the native gene.

Following the initial demonstration of functionality of the Δ12 desaturase in *Yarrowia lipolytica*, the Applicants then explored methods of optimizing PUFA production within this model host organism. Specifically, a Δ12 desaturase-disrupted host strain of *Y. lipolytica* was created and transformed with an expression cassette comprising a heterologous Δ6 desaturase, elongase, Δ5 desaturase and Δ17 desaturase. When fed ALA as a substrate, the transformed host was able to produce STA without co-synthesis of any ω-6 fatty acid (Example 8). Thus, this work demonstrated that upon transformation with appropriate genes of the ω-3 biosynthetic pathway and feeding of ALA as a substrate, only ω-3 fatty acids (e.g., ETA, EPA, DPA, DHA) could be synthesized (i.e., without co-synthesis of ω-6 fatty acids) in *Yarrowia* strains lacking Δ12 desaturase activity.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by: 1.) Sambrook, J., Fritsch, E. F. and Maniatis, T. *Molecular Cloning: A Laboratory Manual*; Cold Spring Harbor Laboratory: Cold Spring Harbor, N.Y. (1989) (Maniatis); 2.) T. J. Silhavy, M. L. Bennan, and L. W. Enquist, Experiments with Gene Fusions; Cold Spring Harbor Laboratory: Cold Spring Harbor, N.Y. (1984); and 3.) Ausubel, F. M. et al., Current Protocols in Molecular Biology, published by Greene Publishing Assoc. and Wiley-Interscience (1987).

Materials and methods suitable for the maintenance and growth of microbial cultures are well known in the art. Techniques suitable for use in the following Examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds), American Society for Microbiology: Washington, D.C. (1994)); or by Thomas D. Brock in *Biotechnology: A Textbook of Industrial Microbiology*, 2$^{nd}$ ed., Sinauer Associates: Sunderland, Mass. (1989). All reagents, restriction enzymes and materials used for the growth and maintenance of microbial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.), unless otherwise specified.

E. coli TOP10 cells and E. coli Electromax DH10B cells were obtained from Invitrogen (Carlsbad, Calif.). Max Efficiency competent cells of E. coli DH5α were obtained from GIBCO/BRL (Gaithersburg, Md.). E. coli (XL1-Blue) competent cells were purchased from the Stratagene Company (San Diego, Calif.). E. coli strains were typically grown at 37° C. on Luria Bertani (LB) plates.

General molecular cloning was performed according to standard methods (Sambrook et al., supra). Oligonucleotides were synthesized by Sigma-Genosys (Spring, Tex.). PCR products were cloned into Promega's pGEM-T-easy vector (Madison, Wis.).

DNA sequence was generated on an ABI Automatic sequencer using dye terminator technology (U.S. Pat. No. 5,366,860; EP 272,007) using a combination of vector and insert-specific primers. Sequence editing was performed in Sequencher (Gene Codes Corporation, Ann Arbor, Mich.). All sequences represent coverage at least two times in both directions. Comparisons of genetic sequences were accomplished using DNASTAR software (DNA Star, Inc.).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "µmole" mean micromole(s), "g" means gram(s), "µg" means microgram(s), "ng" means nanogram(s), "U" means unit(s), "bp" means base pair(s) and "kB" means kilobase(s).

Cultivation of Yarrowia lipolytica

Yarrowia lipolytica strains ATCC #76982 and ATCC #90812 were purchased from the American Type Culture Collection (Rockville, Md.). Y. lipolytica strains were usually grown at 28° C. on YPD agar (1% yeast extract, 2% bactopeptone, 2% glucose, 2% agar). For selection of transformants, minimal medium (0.17% yeast nitrogen base (DIFCO Laboratories, Detroit, Mich.) without ammonium sulfate or amino acids, 2% glucose, 0.1% proline, pH 6.1) was used. Supplements of adenine, leucine, lysine and/or uracil were added as appropriate to a final concentration of 0.01%.

Fatty Acid Analysis of Yarrowia lipolytica

For fatty acid analysis, cells were collected by centrifugation and lipids were extracted as described in Bligh, E. G. & Dyer, W. J. (Can. J. Biochem. Physiol. 37:911-917 (1959)). Fatty acid methyl esters were prepared by transesterification of the lipid extract with sodium methoxide (Roughan, G., and Nishida I. Arch Biochem Biophys. 276(1):38-46 (1990)) and subsequently analyzed with a Hewlett-Packard 6890 GC fitted with a 30-m×0.25 mm (i.d.) HP-INNOWAX (Hewlett-Packard) column. The oven temperature was from 170° C. (25 min hold) to 185° C. at 3.5° C./min.

For direct base transesterification, Yarrowia culture (3 mL) was harvested, washed once in distilled water, and dried under vacuum in a Speed-Vac for 5-10 min. Sodium methoxide (100 µl of 1%) was added to the sample, and then the sample was vortexed and rocked for 20 min. After adding 3 drops of 1 M NaCl and 400 µl hexane, the sample was vortexed and spun. The upper layer was removed and analyzed by GC as described above.

Example 1

Construction of Plasmids Suitable for Gene Expression in Yarrowia lipolytica

The present Example describes the construction of plasmids pY5, pY5-4, pY5-13 and pY5-20.

Construction of Plasmid pY5

The plasmid pY5, a derivative of pINA532 (a gift from Dr. Claude Gaillardin, Insitut National Agronomics, Centre de biotechnologie Agro-Industrielle, laboratoire de Genetique Moleculaire et Cellularie INRA-CNRS, F-78850 Thiverval-Grignon, France), was constructed for expression of heterologous genes in Yarrowia lipolytica, as diagrammed in FIG. 3.

First, the partially-digested 3598 bp EcoRI fragment containing the ARS18 sequence and LEU2 gene of pINA532 was subcloned into the EcoRI site of pBluescript (Strategene, San Diego, Calif.) to generate pY2. The TEF promoter (Muller S., et al. Yeast, 14: 1267-1283 (1998)) was amplified from Yarrowia lipolytica genomic DNA by PCR using TEF5' (SEQ ID NO:1) and TEF3' (SEQ ID NO:2) as primers. PCR amplification was carried out in a 50 µl total volume containing: 100 ng Yarrowia genomic DNA, PCR buffer containing 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene). Amplification was carried out as follows: initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C. The 418 bp PCR product was ligated into pCR-Blunt to generate pIP-tef. The BamHI/EcoRV fragment of pIP-tef was subcloned into the BamHI/SmaI sites of pY2 to generate pY4.

The XPR2 transcriptional terminator was amplified by PCR using pINA532 as template and XPR5' (SEQ ID NO:3) and XPR3' (SEQ ID NO:4) as primers. The PCR amplification was carried out in a 50 µl total volume, using the components and conditions described above. The 179 bp PCR product was digested with SacII and then ligated into the SacII site of pY4 to generate pY5. Thus, pY5 (shown in FIGS. 3 and 4) is useful as a Yarrowia-E. coli shuttle plasmid containing:

1.) a Yarrowia autonomous replication sequence (ARS18);
2.) a ColE1 plasmid origin of replication;
3.) an ampicillin-resistance gene ($Amp^R$), for selection in E. coli;
4.) a Yarrowia LEU2 gene (E.C. 1.1.1.85, encoding isopropylmalate isomerase), for selection in Yarrowia;
5.) the translation elongation promoter (TEF P), for expression of heterologous genes in Yarrowia; and
6.) the extracellular protease gene terminator (XPR2) for transcriptional termination of heterologous gene expression in Yarrowia.

Construction of Plasmids pY-4, pY5-13 And pY5-20 pY5-4 and pY5-13 (FIG. 4) were constructed as derivatives of pY5 to faciliate subcloning and heterologous gene expression in Yarrowia lipolytica.

Specifically, pY5-4 was constructed by three rounds of site-directed mutagenesis using pY5 as template. A NcoI site located inside the Leu2 reporter gene was eliminated from pY5 using oligonucleotides YL1 and YL2 (SEQ ID NOs:5 and 6) to generate pY5-1. A NcoI site was introduced into pY5-1 between the TEF promoter and XPR2 transcriptional terminator by site-directed mutagenesis using oligonucleotides YL3 and YL4 (SEQ ID NOs:7 and 8) to generate pY5-2. A PacI site was then introduced into pY5-2 between the TEF promoter and XPR2 transcriptional terminator using oligonucleotides YL23 and YL24 (SEQ ID NOs:9 and 10) to generate pY5-4.

pY5-13 was constructed by 6 rounds of site-directed mutagenesis using pY5 as template. Both SalI and ClaI sites were eliminated from pY5 by site-directed mutagenesis using oligonucleotides YL5 and YL6 (SEQ ID NOs:11 and 12) to generate pY5-5. A SalI site was introduced into pY5-5 between the Leu2 gene and the TEF promoter by site-directed mutagenesis using oligonucleotides YL9 and YL10 (SEQ ID NOs:13 and 14) to generate pY5-6. A PacI site was introduced into pY5-6 between the LEU2 gene and ARS18 using oligonucleotides YL7 and YL8 (SEQ ID NOs:15 and 16) to generate pY5-8. A NcoI site was introduced into pY5-8 around the translation start codon of the TEF promoter using oligonucleotides YL3 and YL4 (SEQ ID NOs:7 and 8) to generate pY5-9. The NcoI site inside the Leu2 gene of pY5-9 was eliminated using YL1 and YL2 oligonucleotides (SEQ ID NOs:5 and 6) to generate pY5-12. Finally, a BsiWI site was introduced into pY5-12 between the ColEI and XPR2 region using oligonucleotides YL61 and YL62 (SEQ ID NOs:17 and 18) to generate pY5-13.

Plasmid pY20 is a derivative of pY5. It was constructed by inserting a Not I fragment containing a chimeric hygromycin resistance gene (hygromycin-B phosphotransferase; GenBank Accession No. P00557) into the Not/site of pY5. The chimeric gene had the hygromycin resistance ORF under the control of a *Yarrowia lipolytica* TEF promoter.

Example 2

Cloning of the Partial *Yarrowia lipolytica* Δ12 Desaturase and Disruption of the Endogenous Δ12 Desaturase Gene Based on the fatty acid composition of wildtype *Yarrowia lipolytica* (ATCC #76982) which demonstrated that the organism could make LA (18:2) but not ALA (18:3), it was assumed that *Y. lipolytica* would likely contain gene(s) having Δ12 desaturase activity but not Δ15 desaturase activity. Thus, the present Example describes the use of degenerate PCR primers to isolate a partial coding sequence of the *Y. lipolytica* Δ12 desaturase and the use of the partial sequence to disrupt the native gene.

Cloning of the Partial Putative Δ12 Desaturase Sequence from *Y. lipolytica* by PCR Using Degenerate PCR Primers Genomic DNA was isolated from *Y. lipolytica* (ATCC #76982) using DNeasy Tissue Kit (Qiagen, Catalog #69504) and resuspended in kit buffer AE at a DNA concentration of 0.5 µg/µl. PCR amplifications were performed using the genomic DNA as template and several sets of degenerate primers made to amino acid sequences conserved between different fungal Δ12 desaturases (i.e., *Mortierella alpina, Mucor rouxii, Emericella nidulans* and *Pichia augusta*). The best results were obtained with a set of upper and lower degenerate primers, P73 and P76, respectively, as shown in the Table below.

TABLE 3

Degenerate Primers Used For Amplification Of The Partial Putative Δ12 Desaturase

| Primer Set | Description | Degenerate Nucleotide Sequence | Corresponding Amino Acid Sequence |
|---|---|---|---|
| P73 | (32) 26-mers | 5'-TGGGTCCTGGGCCAYG ARTGYGGNCA-3' (SEQ ID NO:19) | WVLGHECGH (SEQ ID NO:20) |
| P76 | (64) 30-mers | 5'-GGTGGCCTCCTCGGCG TGRTARAANGGNAT-3' (SEQ ID NO:21) | (M/I)PFYHAEEAT (SEQ ID NO:22) |

[Note: Abbreviations are standard for nucleotides and proteins. The nucleic acid degeneracy code used is as follows: R = A/G; Y = C/T; and N = A/C/G/T.]

The PCR was carried out in an Eppendorf Mastercycler Gradient thermocycler according to the manufacturer's recommendations. Amplification was carried out as follows: initial denaturation at 95° C. for 1 min, followed by 30 cycles of denaturation at 95° C. for 30 sec, annealing at 58° C. for 1 min, and elongation at 72° C. for 1 min. A final elongation cycle at 72° C. for 10 min was carried out, followed by reaction termination at 4° C.

The expected (ca. 740 bp) size PCR product was detected by agarose gel electrophoresis, isolated, purified, cloned into a pTA vector (Invitrogen) and sequenced. The resultant sequence (contained within SEQ ID NO:23) had homology to known Δ12 desaturases, based on BLAST program analysis (Basic Local Alignment Search Tool; Altschul, S. F., et al., *J. Mol. Biol.* 215:403-410 (1993).

Targeted Disruption of the *Yarrowia lipolytica* Δ12 Desaturase Gene

Targeted disruption of the native Δ12 desaturase gene in *Y. lipolytica* #76982 was carried out by homologous recombination-mediated replacement of the Δ12 desaturase gene with a targeting cassette designated as pY23D12. pY23D12 was derived from plasmid pY20 (Example 1). Specifically, pY23D12 was created by inserting a 642 bp Hind III/Eco RI fragment into similarly linearized pY20. This 642 bp fragment consisted of (in 5' to 3' orientation): 3' homologous sequence from position +718 to +1031 (of the coding sequence (ORF) in SEQ ID NO:23), a Bgl II restriction site and 5' homologous sequence from position +403 to +717 (of the coding sequence (ORF) in SEQ ID NO:23). The fragment was prepared by PCR amplification of 3' and 5' sequences from the 642 bp PCR product using sets of PCR primers P99 and P100 (SEQ ID NOs:25 and 26) and P101 and P102 (SEQ ID NOs:27 and 28), respectively.

pY23D12 was linearized by Bgl II restriction digestion and transformed into mid-log phase *Y. lipolytica* cells by the lithium acetate method according to the method of Chen, D. C. et al. (*Appl Microbiol Biotechnol.* 48(2):232-235 (1997)). Briefly, *Y. lipolytica* ATCC #76982 was streaked onto a YPD plate and grown at 30° C. for approximately 18 hr. Several large loopfuls of cells were scraped from the plate and resuspended in 1 mL of transformation buffer containing:

2.25 mL of 50% PEG, average MW 3350;
0.125 mL of 2 M Li acetate, pH 6.0;
0.125 mL of 2 M DTT; and,
50 µg sheared salmon sperm DNA.

About 500 ng of plasmid DNA were incubated in 100 μl of resuspended cells, and maintained at 39° C. for 1 hr with vortex mixing at 15 min intervals. The cells were plated onto YPD hygromycin selection plates and maintained at 30° C. for 2 to 3 days.

Four hygromycin-resistant colonies were isolated and screened for targeted disruption by PCR. One set of PCR primers (P119 [SEQ ID NO:29] and P120 [SEQ ID NO:30]) was designed to amplify a specific junction fragment following homologous recombination. Another set of PCR primers (P121 [SEQ ID NO:31] and P122 [SEQ ID NO:32]) was designed to detect the native gene. Three of the four hygromycin-resistant colonies were positive for the junction fragment and negative for the native fragment, thus confirming targeted integration.

Determination of Fatty Acid Profile in the Δ12 Desaturase-Disrupted Strain

Disruption of the Δ12 desaturase gene was further confirmed by GC analysis of the total lipids in one of the disrupted strains, designated as "Q-d12D". Single colonies of wild type (ATCC #76982) and Q-d12D *Y. lipolytica* were each grown in 3 mL minimal media (formulation/L: 20 g glucose, 1.7 g yeast nitrogen base, 1 g L-proline, 0.1 g L-adenine, 0.1 g L-lysine, pH 6.1) at 30° C. to an $OD_{600}$~1.0. The cells were harvested, washed in distilled water, speed vacuum dried and subjected to direct trans-esterification and GC analysis (as described in the General Methods).

The fatty acid profile of wildtype *Yarrowia* and the transformant Q-d12D comprising the disrupted Δ12 desaturase are shown below in Table 4. Fatty acids are identified as 16:0 (palmitate), 16:1 (palmitoleic acid), 18:0, 18:1 (oleic acid) and 18:2 (LA); and the composition of each is presented as a % of the total fatty acids.

TABLE 4

Fatty Acid Composition (% Of Total Fatty Acids)
In Wildtype And Transformant *Yarrowia lipolytica*

| Strain | 16:0 | 16:1 | 18:0 | 18:1 | 18:2 |
|---|---|---|---|---|---|
| Wild type | 11 | 14 | 2 | 33 | 34 |
| Q-d12D disrupted | 6 | 15 | 1 | 74 | nd |

*nd = not detectable

Results indicated that the native Δ12 desaturase gene in the Q-d12D strain was inactivated. Thus, it was possible to conclude that there was only one gene encoding a functional Δ12 desaturase in *Yarrowia lipolytica* ATCC #76982.

Example 3

Cloning of the Full-Length *Yarrowia lipolytica* Δ12 Desaturase Gene

The present Example describes the recovery of the genomic sequences flanking the disrupted gene by plasmid rescue, using the sequence in the rescued plasmid to PCR the intact open reading frame of the native gene. The full-length gene and its deduced amino acid sequence is compared to other fungal desaturases.

Plasmid Rescue of the *Yarrowia lipolytica* Δ12 Desaturase Gene

Since the Δ12 desaturase gene was disrupted by the insertion of the entire pY23D12 vector that also contained an *E. coli* ampicillin-resistant gene and *E. coli* ori, it was possible to rescue the flanking sequences in *E. coli*. For this, genomic DNA of *Y. lipolytica* strain Q-d12D (carrying the disrupted Δ12 desaturase gene; Example 2) was isolated using the DNeasy Tissue Kit. Then, 10 μg of the genomic DNA was digested with 50 μl of restriction enzymes Age I, Avr II, Nhe I and Sph I in a reaction volume of 200 μl. Digested DNA was extracted with phenol:chloroform and resuspended in 40 μl deionized water. The digested DNA (10 μl) was self-ligated in a 200 μl ligation mixture containing 3 U T4 DNA ligase. Ligation was carried out at 16° C. for 12 hrs. The ligated DNA was extracted with phenol:chloroform and resuspended in 40 μl deionized water. Finally, 1 μl of the resuspended ligated DNA was used to transform *E. coli* by electroporation and plated onto LB plates containing ampicillin (Ap). Ap-resistant colonies were isolated and analyzed for the presence of plasmids by miniprep. The following insert sizes were found in the recovered or rescued plasmids (Table 5):

TABLE 5

Insert Sizes Of Recovered Plasmids,
According To Restriction Enzyme

| Enzyme | Plasmid Insert Size (kB) |
|---|---|
| AgeI | 1.6 |
| AvrII | 2.5 |
| NheI | 9.4 |
| SphI | 6.6 |

Sequencing of the plasmids was initiated with sequencing primers P99 (SEQ ID NO:25) and P102 (SEQ ID NO:28).

Based on the sequencing results, a full-length gene encoding the *Yarrowia lipolytica* Δ12 desaturase gene was assembled (1-936 bp; SEQ ID NO:23). Specifically, SEQ ID NO:23 encoded an open reading frame of 1257 bases (nucleotides +283 to +1539), while the deduced amino acid sequence was 419 residues in length (SEQ ID NO:24).

The *Yarrowia lipolytica* Δ12 desaturase protein (SEQ ID NO:24) was used as a query against available sequence databases of filamentous fungi, including: 1.) public databases of *Neurospora crassa*, *Magnaporthe grisea*, *Aspergillus nidulans* and *Kluyveromuces lactis*; and 2.) a DuPont EST library of *Fusarium moniliforme* strain M-8114 (E.I. du Pont de Nemours and Co., Inc., Wilmington, Del.) (*F. moniliforme* strain M-8114 available from the *Fusarium* Research Center, University Park, Pa.; see also *Plant Disease* 81(2): 211-216. (1997)). These BLAST searches identified the following homologs (Table 6).

TABLE 6

Description of Δ12 Desaturase Homologs

| Source | Symbol | Organism |
|---|---|---|
| Contig 1.122 (scaffold 9) in the *A. nidulans* genome project (sponsored by the Center for Genome Research (CGR), Cambridge, MA. | An1 | *Aspergillus nidulans* |
| Contig 1.15 (scaffold 1) in the *A. nidulans* genome project; AAG36933 | An2 | *Aspergillus nidulans* |
| DuPont EST sequence database, U.S. Provisional Application No. 60/519191 | Fm1 | *Fusarium moniliforme* |
| DuPont EST sequence database, U.S. Provisional Application No. 60/519191 | Fm2 | *Fusarium moniliforme* |
| Ctg4369-0000002-2.1 in the Genolevures project. | Kl | *Kluyveromyces lactis* |
| Locus MG08474.1 in contig 2.1597 in the *M. grisea* genome project (sponsored by the CGR and International Rice Blast Genome Consortium. | Mg1 | *Magnaporthe grisea* |

TABLE 6-continued

Description of Δ12 Desaturase Homologs

| Source | Symbol | Organism |
|---|---|---|
| Locus MG01985.1 in contig 2.375 in the *M. grisea* genome project | Mg2 | *Magnaporthe grisea* |
| GenBank Accession No. AABX01000374 | Nc1 | *Neurospora crassa* |
| GenBank Accession No. AABX01000577 | Nc2 | *Neurospora crassa* |

All of the homologs were either unannotated or annotated as a fatty acid desaturase. Furthermore, the nucleotide sequences from *A. nidulans* were incomplete and/or genomic with putative intron sequences; the Applicants made a tentative assembly of the deduced amino acids for comparison with amino acid sequences from the other homologs.

A comparison of the deduced amino acid sequence of the *Yarrowia lipolytica* Δ12 desaturase (SEQ ID NO:24) was made with the fungal homologs shown above in Table 6 and other known Δ12 desaturases, as described below in Table 7.

TABLE 7

Known Δ12 Desaturases

| Source | Symbol | Organism |
|---|---|---|
| GenBank Accession No. AAG36933 | En | *Emericella nidulans* |
| GenBank Accession No. AF110509 | Ma | *Mortierella alpina* |
| GenBank Accession No. AB020033 | MaB | *Mortierella alpina* |
| GenBank Accession No. AAL13300; AF417244 | MaC | *Mortierella alpina* |
| GenBank Accession No. AF161219 | Mr | *Mucor rouxii* |
| Ctg1334-0000001-1.1. (see Genolevures project.) | Pa | *Pichia augusta* |

Specifically, the analysis was performed using the ClustalW alignment algorithm (Slow/Accurate, Gonnet option; Thompson et. al., *Nucleic Acids Res.* 22:4673-4680 (1994)) of the DNASTAR software package (DNASTAR Inc., Madison, Wis.). This comparison revealed the Pair Distances shown in FIG. 5, wherein "Yl" corresponds to the *Yarrowia lipolytica* Δ12 desaturase. Percent similarity and divergence are shown in the upper and lower triangles, respectively. Thus, the *Y. lipolytica* Δ12 desaturase was at least 53% identical to the other Δ12 desaturase homologs (having maximal identity to the *A. nidulans* sequence (An2)).

Example 4

Expression of *Yarrowia lipolytica* Δ12 Desaturase ORF Under the Control of a Heterologous *Yarrowia* Promoter The present Example describes the expression of the Δ12 desaturase ORF in a chimeric gene under the control of a heterologous (non-Δ12 desaturase) *Yarrowia* promoter to complement the Δ12 desaturase-disrupted mutant and enable the overproduction of LA in the wildtype strain.

Expression of *Y. lipolytica* Δ12 Desaturase in *Yarrowia lipolytica*.

The ORF encoding the *Y. lipolytica* Δ12 desaturase was PCR amplified using upper primer P147 (SEQ ID NO:33) and lower primer P148 (SEQ ID NO:34) from the genomic DNA of *Y. lipolytica* ATCC #76982. The correct sized (1260 bp) fragment was isolated, purified, digested with Nco I and Not I and cloned into NcoI-Not I cut pY5-13 vector (Example 1), such that the gene was under the control of the TEF promoter. Correct transformants were confirmed by miniprep analysis and the resultant plasmid was designated pY25-d12d.

Plasmids pY5-13 (the "control") and pY25-d12d were each individually transformed into *Y. lipolytica* ATCC #76982 wild-type (WT) and d12d-disrupted strains (Q-d12D, also referred to as "d12KO" in the Table below) and selected on Bio101 DOB/CSM-Leu plates.

Single colonies of transformants were grown up and GC analyzed as described in the General Methods. Results are shown in the Table below. Fatty acids are identified as 16:0, 16:1, 18:0, 18:1 (oleic acid) and 18:2 (LA); and the composition of each is presented as a % of the total fatty acids. "D12d SC" was calculated according to the following formula: $([18:2]/[18:1+18:2])*100$ and represents percent substrate conversion.

TABLE 8

Fatty Acid Composition (% Of Total Fatty Acids)

| Strain | Plasmid | % 16:0 | % 16:1 | % 18:0 | % 18:1 | % 18:2 | D12d SC |
|---|---|---|---|---|---|---|---|
| D12KO | pY5-13 | 8 | 10 | 2 | 80 | nd | 0 |
| D12KO | pY25-d12d | 11 | 8 | 2 | 34 | 45 | 57 |
| WT | pY5-13 | 10 | 10 | 1 | 32 | 47 | 59 |
| WT | pY25-d12d | 12 | 7 | 2 | 21 | 59 | 74 |

*nd = not detectable

The results showed that the Δ12 desaturase promoter was equivalent in strength to the TEF promoter (57% substrate conversion in the d12KO strain expressing the Δ12 desaturase under the control of the TEF promoter, compared to 59% substrate conversion in the wild type strain expressing the Δ12 desaturase under the control of the native Δ12 desaturase promoter). On this basis, it is expected that the Δ12 desaturase promoter can be used for heterologous expression of other ORFs in *Yarrowia*.

Additionally, the results demonstrated that overexpression of the Δ12 desaturase in wild type cells resulted in even higher levels of LA production (18:2). Specifically, 74% substrate conversion was observed in the wildtype strain overexpressing the Δ12 desaturase under the control of the TEF promoter, as opposed to only 59% substrate conversion in the wild type strain. On the basis of these results, it would be expected that overexpression of the Δ12 desaturase, in combination of other genes for PUFA biosynthesis (e.g., a Δ6 desaturase, elongase, Δ5 desaturase, Δ17 desaturase), would result in higher production of ω-3 and/or ω-6 PUFAs. Additionally, it would be expected that disruption of the native Δ12 desaturase and expression of other genes for PUFA biosynthesis (e.g., a Δ6 desaturase, elongase, Δ5 desaturase, Δ17 desaturase) would result in production of "pure" ω-3 PUFAs, without co-synthesis of any ω-6 PUFAs.

Example 5

Selection of Δ6 Desaturase, Δ5 Desaturase, Δ17 Desaturase and High Affinity PUFA Elongase Genes For Expression in *Yarrowia lipolytica*

Prior to the introduction of specific genes encoding an ω-3 and/or ω-6 biosynthetic pathway into *Yarrowia lipolytica* containing a disrupted Δ12-desaturase (Example 8), it was necessary to confirm the functionality of heterologous Δ6 desaturase, elongase, Δ5 desaturase and Δ17 desaturase genes expressed in *Yarrowia*. This was accomplished by measuring the conversion efficiency of each wildtype protein in the alternate host. Specifically, a *Mortierella alpina* Δ5 desaturase, a *M. alpina* Δ6 desaturase, a *Saprolegnia diclina* Δ17 desaturase and a *M. alpina* high affinity PUFA elongase were separately expressed and screened for activity in substrate-feeding trials.

Construction of Expression Plasmids

In general, wildtype desaturase or elongase genes were either isolated by restriction digestion or amplified by PCR and inserted into appropriate vectors for expression. Each PCR amplification was carried out in a 50 µl total volume, comprising PCR buffer containing: 10 ng template, 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows (unless otherwise specified): initial denaturation at 95° C. for 3 min, followed by 35 cycles of the following: 95° C. for 1 min, 56° C. for 30 sec, 72° C. for 1 min. A final extension cycle of 72° C. for 10 min was carried out, followed by reaction termination at 4° C.

Wild Type *Mortierella alpina* (Accession #AF465281) Δ6 Desaturase

The 1384 bp NcoI/NotI fragment of pCGR5 (U.S. Pat. No. 5,968,809), which contains the *M. alpina* Δ6 desaturase gene (SEQ ID NO:36), was inserted into the NcoI/NotI sites of pY5-2 (Example 1) to generate pY54.

Wild Type *Mortierella alpina* (Accession #AF067654) Δ5 Desaturase

Figure 6A:
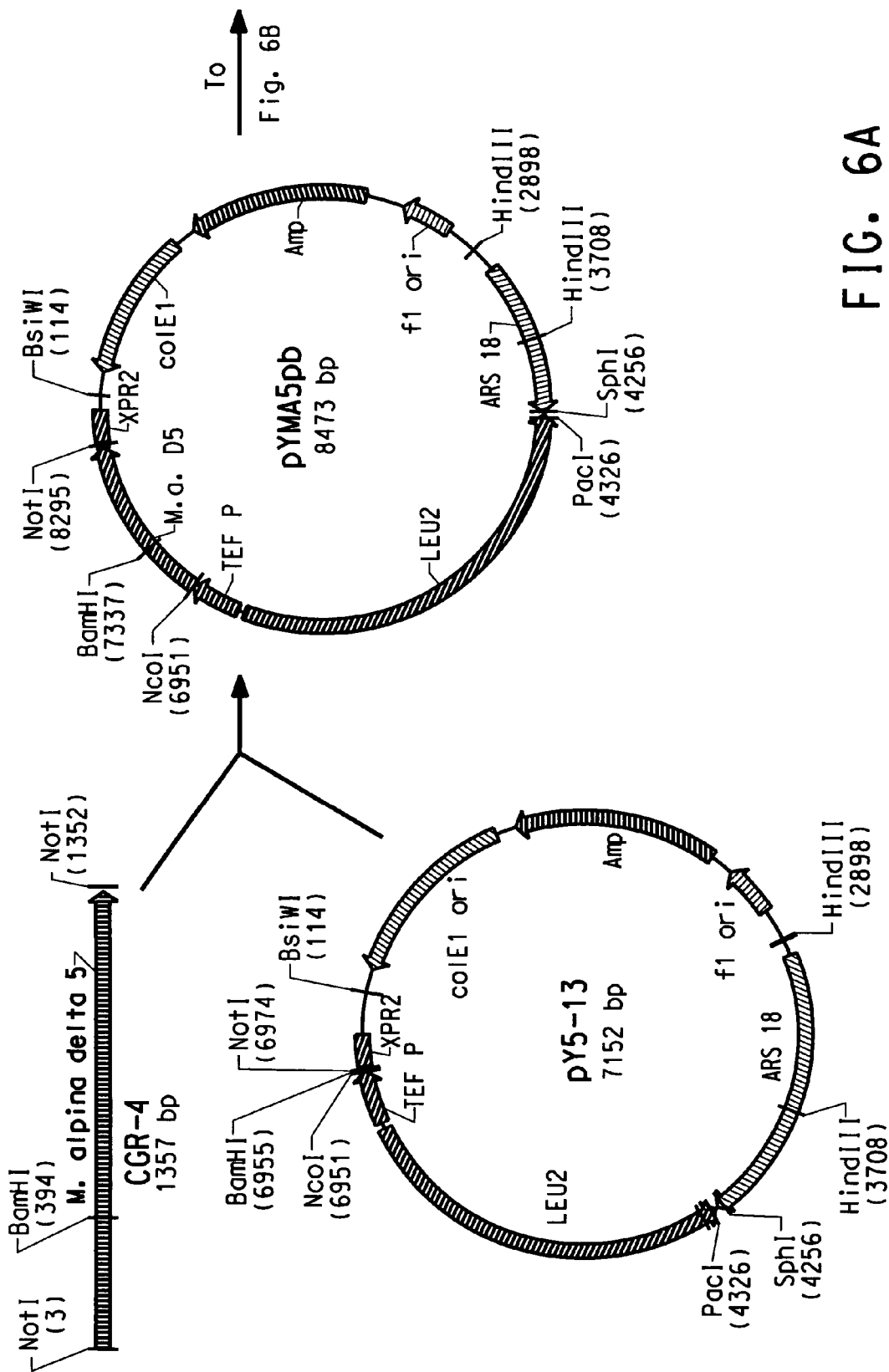
FIG. 6 is a schematic presentation of the construction of intermediate vector pYZM5CHPPA.
Figure 6B:
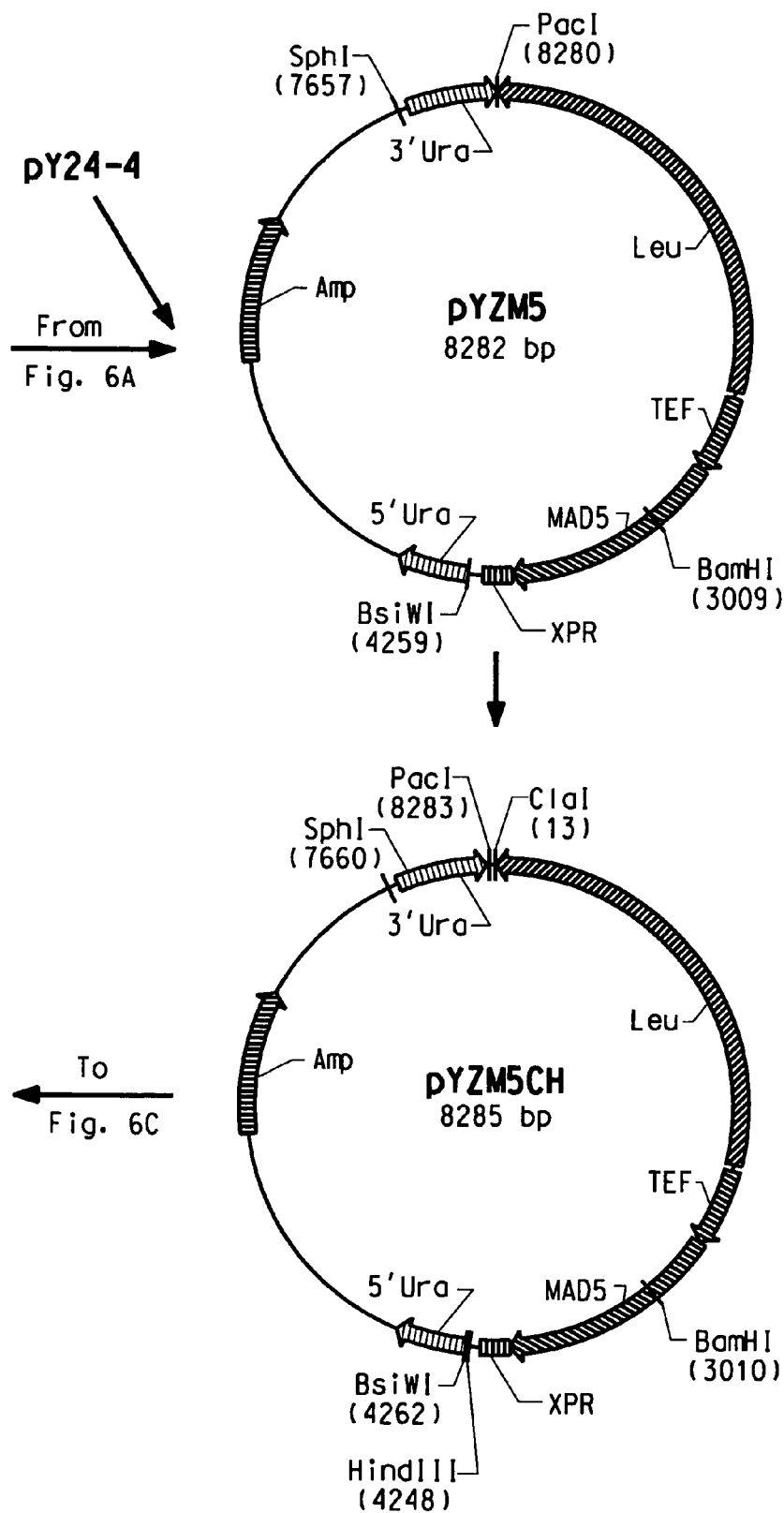

The *M. alpina* Δ5 desaturase gene (SEQ ID NO:38) was amplified by PCR using oligonucleotides YL11 and YL12 (SEQ ID NOs:40 and 41) as primers and plasmid pCGR-4 (U.S. Pat. No. 6,075,183) as template. PCR amplification was carried out as described above, with the exception that the elongation step was extended to 1.5 min (for cycles 1-35); The 1357 bp PCR product was digested with NcoI/NotI and ligated to NcoI/NotI-digested pY5-13 (described in Example 1) to generate pYMA5pb (FIG. 6).

Wild Type *Saprolegnia diclina* (ATCC #56851) Δ17 Desaturase

The Wild type Δ17 desaturase gene of *S. diclina* was amplified from plasmid pRSP19 (US 2003/0196217 A1) by PCR using oligonucleotides YL21A (SEQ ID NO:42) and YL22 (SEQ ID NO:43) as primers. The PCR products were digested with NcoI/PacI and then ligated to NcoI/PacI-digested pY54 (FIG. 4; described in Example 1) to generate pYSD17.

Wild Type *Mortierella alpina* (Accession #AX464731) High Affinity Elongase

Figure 3B:
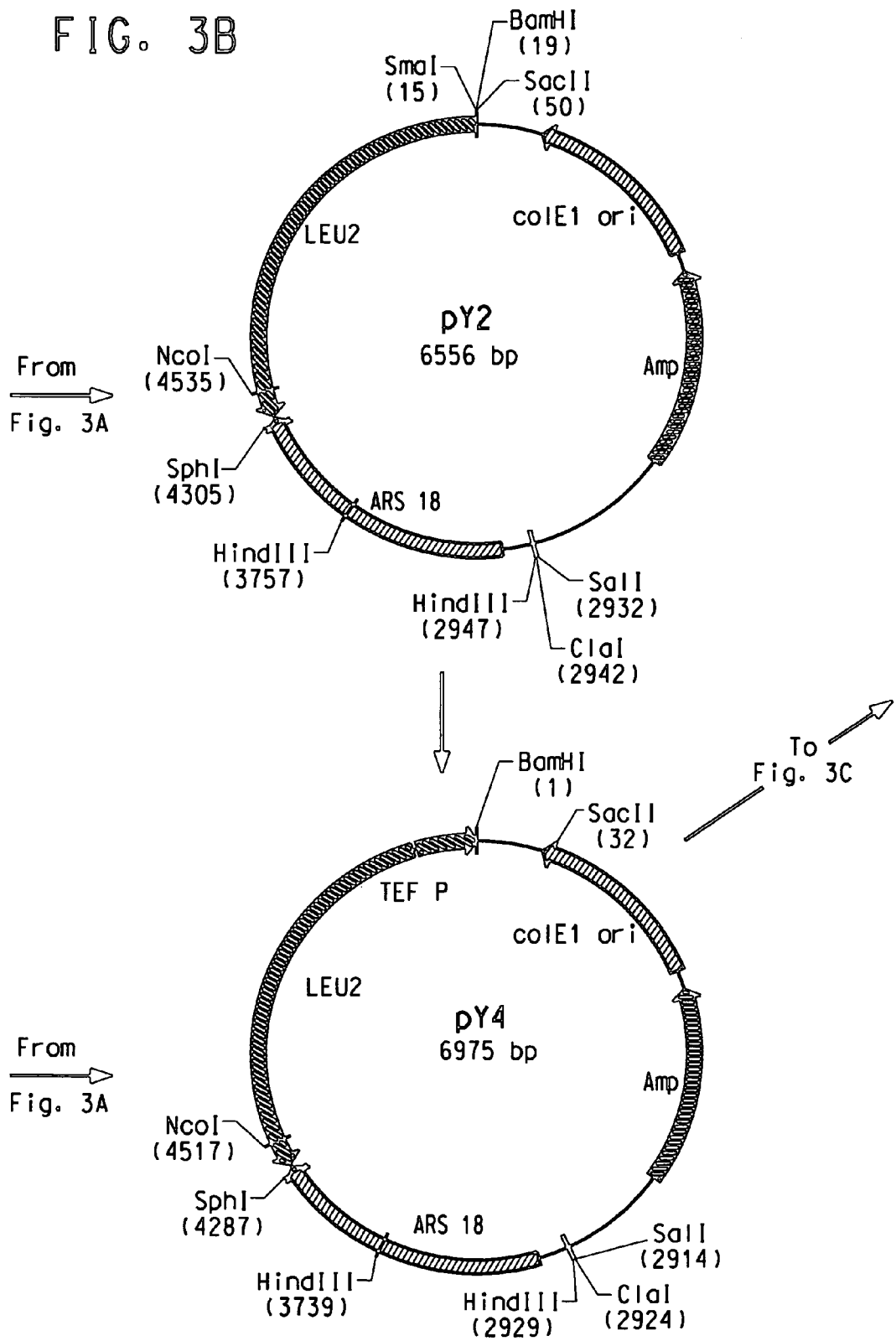
FIG. 3 illustrates the construction of the plasmid vector pY5 for gene expression in *Yarrowia lipolytica*.
Figure 3C:
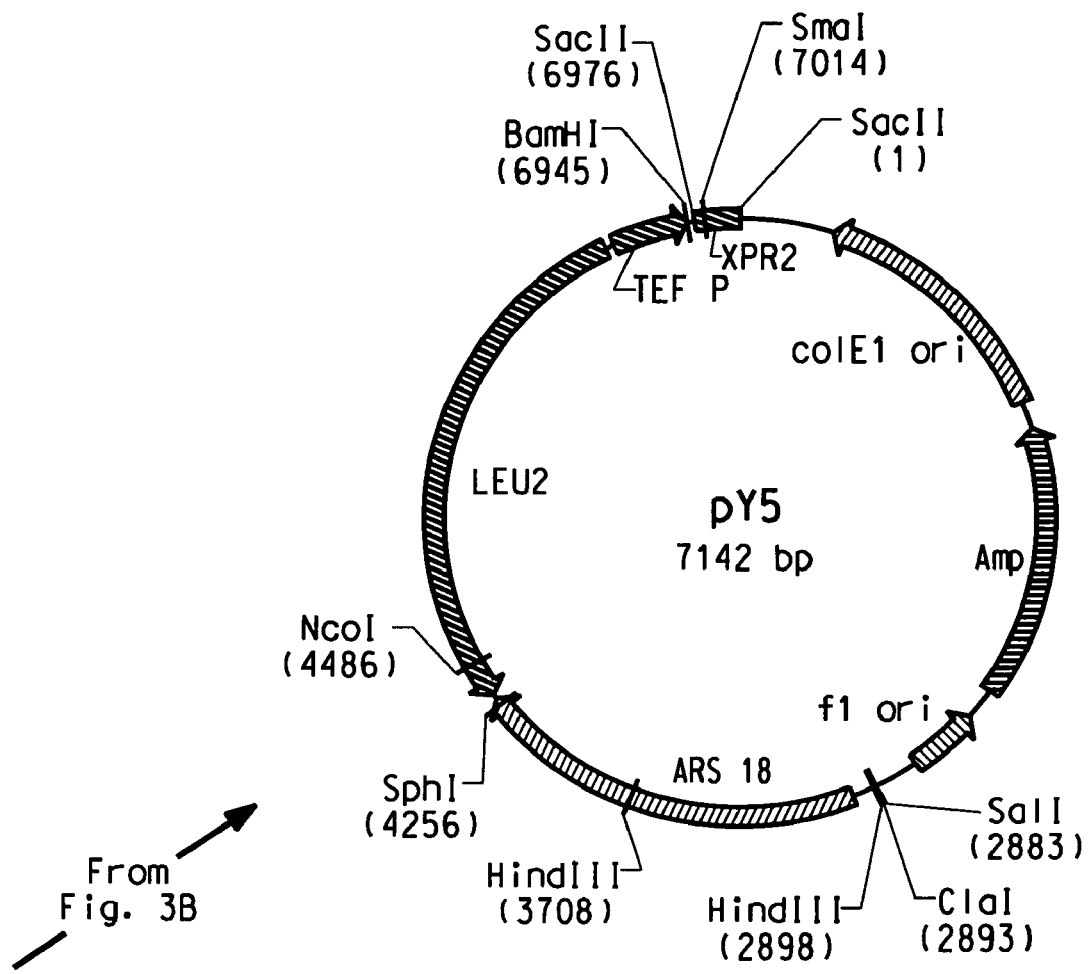
Figure 4:
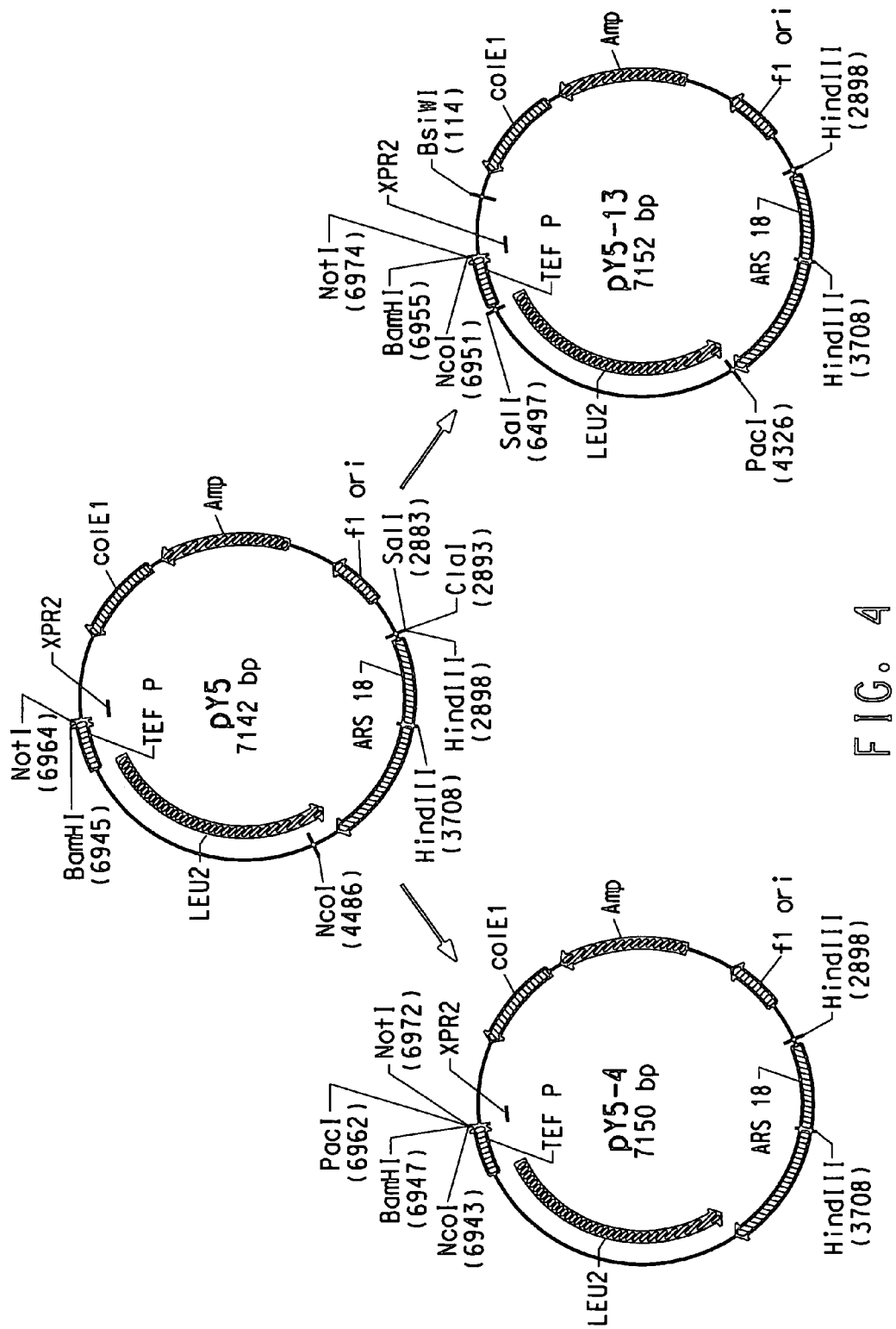
FIG. 4 illustrates the construction of plasmid vectors pY5-13 and pY5-4 for gene expression in *Y. lipolytica*.

The 973 bp NotI fragment of pRPB2 (WO 00/12720), containing the coding region of a *M. alpina* high affinity PUFA elongase gene (SEQ ID NO:44), was inserted into the NotI site of pY5 (described in Example 1; FIGS. 3 and 4) to generate pY58.

Transformation of *Yarrowia lipolytica*

The plasmids pY54, pYMA5pb, pYSD17 and pY58 were transformed separately into *Y. lipolytica* ATCC# 76982 according to the method of Chen, D. C. et al. (*Appl Microbiol Biotechnol.* 48(2):232-235 (1997)), and as described in Example 2 (with the exception that a leucine auxotroph of *Yarrowia* was used for transformation and transformants were selected on minimal media plates lacking leucine).

Determination of Percent Substrate Conversion

Single colonies of transformant *Y. lipolytica* containing pY54, pYMA5pb, pYSD17 or pY58 were each grown in 3 mL minimal media (20 g/L glucose, 1.7 g/L yeast nitrogen base without amino acids, 1 g/L L-proline, 0.1 g/L L-adenine, 0.1 g/L L-lysine, pH 6.1) at 30° C. to an $OD_{600}$~1.0. For substrate feeding, 100 µl of cells were then subcultured in 3 mL minimal media containing 10 µg of substrate for about 24 hr at 30° C. Cells were subsequently collected by centrifugation and the lipids were extracted as described in the General Methods. Fatty acid methyl esters were prepared by transesterification of the lipid extract. Percent substrate conversion was determined as: [product/(substrate+product)]*100.

Percent Substrate Conversion By *M. alpina* Δ6 Desaturase

The *M. alpina* Δ6 desaturase converts LA to GLA and/or ALA to STA. *Y. lipolytica* strains containing pY54 were grown as described above (no substrate feeding required) and lipids were analyzed. The results showed that *Yarrowia* strains with pY54 converted about 30% LA to GLA.

Percent Substrate Conversion By *M. alpina* Δ5 Desaturase

The Δ5 desaturase from *M. alpina* converts DGLA to ARA and/or ETA to EPA. *Y. lipolytica* containing pYMA5pb was grown from a single colony, subcultured in minimal media containing 10 µg of DGLA and then subjected to lipid analysis as described above. *Yarrowia* strains with pYMA5pb converted about 30% of intracellular DGLA to ARA.

Percent Substrate Conversion By *S. diclina* Δ17 Desaturase

The *S. diclina* Δ17 desaturase converts ARA to EPA and/or DGLA to ETA. *Y. lipolytica* strains containing pYSD17 were grown from single colonies, subcultured in minimal media containing 10 µg of ARA and subjected to lipid analysis as described above. The results of the ARA feeding experiments showed that *Yarrowia* strains with pYSD17 converted about 23% of intracellular ARA to EPA.

Percent Substrate Conversion of Wild Type *M. alpina* High Affinity Elongase

The *M. alpina* high affinity PUFA elongase converts GLA to DGLA, STA to ETA, and/or EPA to DPA. *Y. lipolytica* strains containing pY58 were grown from single colonies, subcultured in minimal media containing 10 µg of GLA and subjected to lipid analysis as described above. The results of the GLA feeding experiments showed that *Yarrowia* strains with pY58 converted about 30% of intracellular GLA to DGLA.

Example 6

Synthesis and Expression of a Codon-Optimized Δ17 Desaturase Gene in *Yarrowia lipolytica*

Based on the results of Example 5, genes encoding Δ6 desaturase, elongase and Δ5 desaturase activies were available that each enabled ~30% substrate conversion in *Yarrowia lipolytica*. The Δ17 desaturase from *S. diclina*, however, had a maximum conversion efficiency of only 23%. Thus, a codon-optimized Δ17 desaturase gene was designed, based on the *Saprolegnia diclina* DNA sequence (SEQ ID NO:35), according to the *Yarrowia* codon usage pattern, the consensus sequence around the 'ATG' translation initiation codon and the general rules of RNA stability (Guhaniyogi, G. and J. Brewer, *Gene* 265(1-2):11-23 (2001)).

In addition to modification to the translation initiation site, 127 bp of the 1077 bp coding region, comprising 117 codons, were codon-optimized. A comparison between this codon-optimized DNA sequence (SEQ ID NO:46) and the *S. diclina* Δ17 desaturase gene DNA sequence (SEQ ID NO:35) is shown in FIG. 7, wherein nucleotides in bold text correspond to nucleotides that were modified in the codon-optimized gene. None of the modifications in the codon-optimized gene changed the amino acid sequence of the encoded protein (SEQ ID NO:47).

The synthetic, codon-optimized Δ17 desaturase was suitable for expression with other genes for PUFA biosynthesis, to test the hypothesis of whether expression in a *Yarrowia lipolytica* host having its native Δ12 desaturase disrupted would result in production of "pure" ω-3 PUFAs, without co-synthesis of any ω-6 PUFAs (infra, Example 8).

Determining the Preferred Codon Usage in *Yarrowia lipolytica*

Approximately 100 genes of *Y. lipolytica* were found in the National Center for Biotechnology Information public database. The coding regions of these genes, comprising 121,167 bp, were translated by the Editseq program of DNAStar to the corresponding 40,389 amino acids and were tabulated to determine the *Y. lipolytica* codon usage profile shown in Table 9. The column titled "No." refers to the number of times a given codon encodes a particular amino acid in the sample of 40,389 amino acids. The column titled "%" refers to the frequency that a given codon encodes a particular amino acid. Entries shown in bold text represent the codons favored in *Yarrowia lipolytica*.

TABLE 9

Codon Usage In Yarrowia lipolytica

| Condon | Amino Acid | No. | % | Condon | Amino Acid | No. | % |
|---|---|---|---|---|---|---|---|
| GCA | Ala (A) | 359 | 11.4 | AAA | Lys (K) | 344 | 14.8 |
| GCC | Ala (A) | 1523 | 48.1 | AAG | Lys (K) | 1987 | 85.2 |
| GCG | Ala (A) | 256 | 8.1 | AUG | Met (M) | 1002 | 100 |
| GCU | Ala (A) | 1023 | 32.3 | UUC | Phe (F) | 996 | 61.1 |
| AGA | Arg (R) | 263 | 13.2 | UUU | Phe (F) | 621 | 38.9 |
| AGG | Arg (R) | 91 | 4.6 | CCA | Pro (P) | 207 | 9.6 |
| CGA | Arg (R) | 1133 | 56.8 | CCC | Pro (P) | 1125 | 52.0 |
| CGC | Arg (R) | 108 | 5.4 | CCG | Pro (P) | 176 | 8.2 |
| CGG | Arg (R) | 209 | 1.0 | CCU | Pro P | 655 | 30.2 |
| CGU | Arg (R) | 189 | 9.5 | AGC | Ser (S) | 335 | 11.3 |
| AAC | Ans (N) | 1336 | 84.0 | AGU | Ser (S) | 201 | 6.8 |
| AAU | Ans (N) | 255 | 16.0 | UCA | Ser (S) | 221 | 7.5 |
| GAC | Asp (D) | 1602 | 66.8 | UCC | Ser (S) | 930 | 31.5 |
| GAU | Asp (D) | 795 | 33.2 | UCG | Ser (S) | 488 | 16.5 |
| UGC | Cys (C) | 268 | 53.2 | UCU | Ser (S) | 779 | 26.4 |
| UGU | Cys (C) | 236 | 46.8 | UAA | Term | 38 | 46.9 |
| CAA | Gln (Q) | 307 | 17.0 | UAG | Term | 30 | 37.0 |
| CAG | Gln (Q) | 1490 | 83.0 | UGA | Term | 13 | 16.1 |
| GAA | Glu (E) | 566 | 23.0 | ACA | Thr (T) | 306 | 12.7 |
| GAG | Glu (E) | 1893 | 77.0 | ACC | Thr (T) | 1245 | 51.6 |
| GGA | Gly (G) | 856 | 29.7 | ACG | Thr (T) | 269 | 11.1 |

TABLE 9-continued

Codon Usage In Yarrowia lipolytica

| Condon | Amino Acid | No. | % | Condon | Amino Acid | No. | % |
|---|---|---|---|---|---|---|---|
| GGC | Gly (G) | 986 | 34.2 | ACU | Thr (T) | 595 | 24.6 |
| GGG | Gly (G) | 148 | 5.1 | UGG | Trp (W) | 488 | 100 |
| GGU | Gly (G) | 893 | 31.0 | UAC | Tyr (Y) | 988 | 83.2 |
| CAC | His (H) | 618 | 65.5 | UAU | Tyr (Y) | 200 | 16.8 |
| CAU | His H | 326 | 34.5 | GUA | Val (V) | 118 | 4.2 |
| AUA | Ile (I) | 42 | 2.1 | GUC | Val (V) | 1052 | 37.3 |
| AUC | Ile (I) | 1106 | 53.7 | GUG | Val (V) | 948 | 33.6 |
| AUU | Ile (I) | 910 | 44.2 | GUU | Val (V) | 703 | 24.9 |
| CUA | Leu (L) | 166 | 4.7 | | | | |
| CUC | Leu (L) | 1029 | 29.1 | | | | |
| CUG | Leu (L) | 1379 | 38.9 | | | | |
| CUU | Leu (L) | 591 | 16.7 | | | | |
| UUA | Leu (L) | 54 | 1.5 | | | | |
| UUG | Leu (L) | 323 | 9.1 | | | | |

Figure 8:
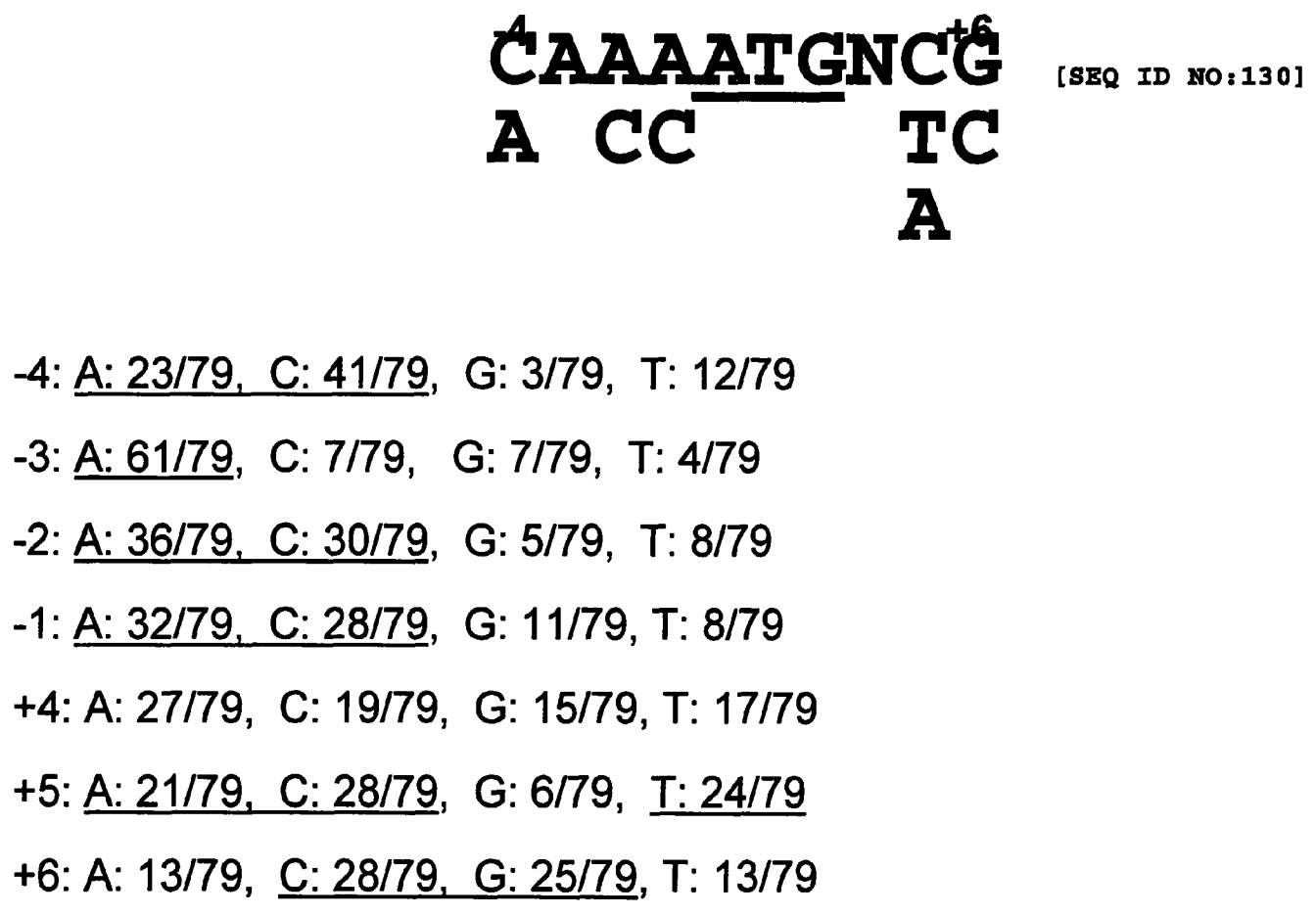

For further optimization of gene expression in *Y. lipolytica*, the consensus sequence around the 'ATG' initiation codon of 79 genes was examined. In FIG. 8, the first 'A' of the underlined ATG translation codon is considered to be +1. Seventy seven percent of the genes analyzed had an 'A' in the −3 position, indicating a strong preference for 'A' at this position. There was also preference for 'A' or 'C' at the −4, −2 and −1 positions, an 'A', 'C' or 'T' at position +5, and a 'G' or 'C' at position +6. Thus, the preferred consensus sequence of the codon-optimized translation initiation site for optimal expression of genes in *Y. lipolytica* is 'MAMMATGNHS' (SEQ ID NO:130), wherein the nucleic acid degeneracy code used is as follows: M=A/C; S=C/G; H=A/C/T; and N=A/C/G/T.

In Vitro Synthesis of a Codon-Optimized Gene

Figure 9:
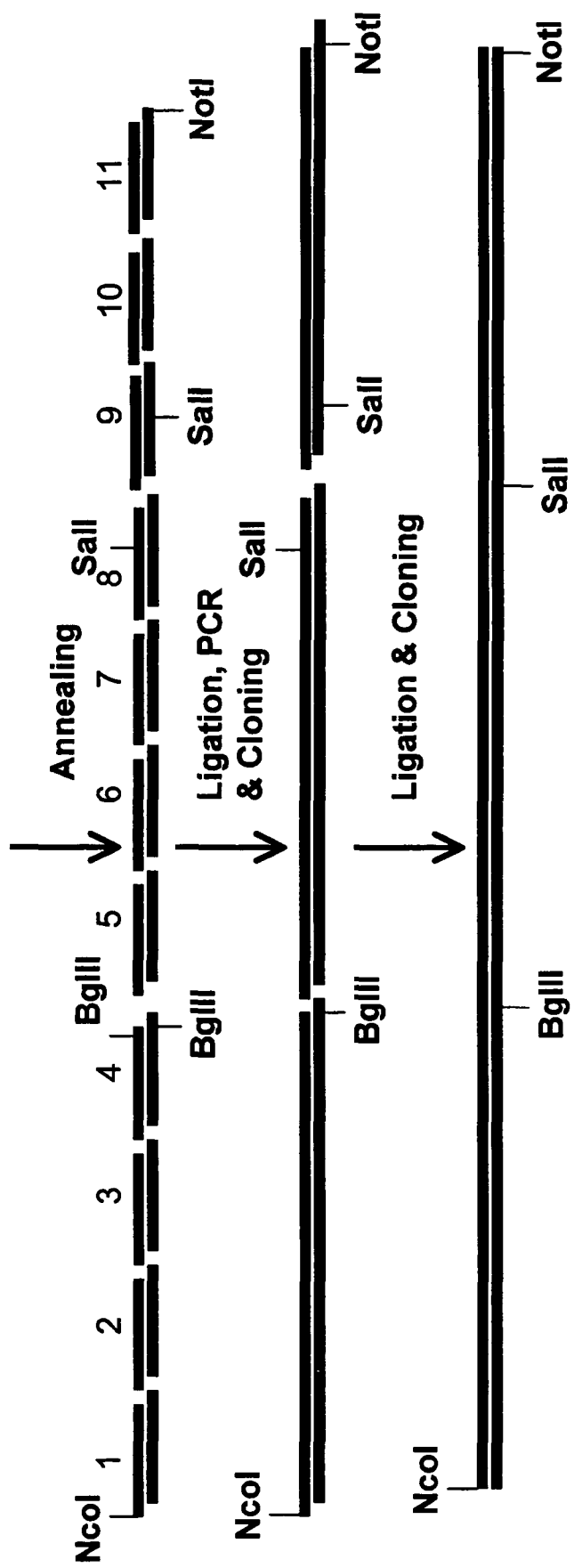
FIG. 9 illustrates the strategy for in vitro synthesis of the codon-optimized Δ17 desaturase gene.

The method used to synthesize the codon-optimized Δ17 desaturase gene is illustrated in FIG. 9. First, eleven pairs of oligonucleotides were designed to extend the entire length of the codon-optimized coding region of the *S. diclina* Δ17 desaturase gene (e.g., D17-1A, D17-1B, D17-2A, D17-2B, D17-3A, D17-3B, D17-4A, D17-4B, D17-5A, D17-5B, D17-6A, D17-6B, D17-7A, D17-7B, D17-8A, D17-8B, D17-9A, D17-9B, D17-10A, D17-10B, D17-11A and D17-11B, corresponding to SEQ ID NOs:48-69). Each pair of sense (A) and anti-sense (B) oligonucleotides were complementary, with the exception of a 4 bp overhang at each 5'-end. Additionally, primers D17-1A, D17-4B, D17-5A, D17-8A and D17-8B also introduced NcoI, BglII and SalI restriction sites for subsequent subcloning, respectively.

100 ng of each oligonucleotide was phosphorylated at 37° C. for 1 hr in a volume of 20 μl containing 50 mM Tris-HCl (pH 7.5), 10 mM MgCl$_2$, 10 mM DTT, 0.5 mM spermidine, 0.5 mM ATP and 10 U of T4 polynucleotide kinase. Each pair of sense and antisense oligonucleotides was mixed and annealed in a thermocycler using the following parameters: 95° C. (2 min), 85° C. (2 min), 65° C. (15 min), 37° C. (15 min), 24° C. (15 min) and 4° C. (15 min). Thus, D17-1A (SEQ ID NO:48) was annealed to D17-1B (SEQ ID NO:49) to produce the double-stranded product "D17-1AB". Similarly, D17-2A (SEQ ID NO:50) was annealed to D17-2B (SEQ ID NO:51) to produce the double-stranded product "D17-2AB", etc.

Three separate pools of annealed, double-stranded oligonucleotides were then ligated together, as shown below:
Pool 1: comprised D17-1AB, D17-2AB, D17-3AB and D17-4AB;
Pool 2: comprised D17-5AB, D17-6AB, D17-7AB and D17-8AB; and
Pool 3: comprised D17-9AB, D17-10AB and D17-11AB.

Each pool of annealed oligonucleotides was mixed in a volume of 20 μl with 10 U of T4 DNA ligase and the ligation reaction was incubated overnight at 16° C.

The product of each ligation reaction was then amplified by PCR. Specifically, using the ligated "Pool 1" mixture (i.e., D17-1AB, D17-2AB, D17-3AB, and D17-4AB) as template, and oligonucleotides D17-1 (SEQ ID NO:70) and D17-4R (SEQ ID NO:71) as primers, the first portion of the codon-optimized Δ17 desaturase gene was amplified by PCR. The PCR amplification was carried out in a 50 μl total volume, comprising PCR buffer containing 10 mM KCl, 10 mM $(NH_4)_2SO_4$, 20 mM Tris-HCl (pH 8.75), 2 mM $MgSO_4$, 0.1% Triton X-100, 100 μg/mL BSA (final concentration), 200 μM each deoxyribonucleotide triphosphate, 10 pmole of each primer and 1 μl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 40 sec. A final extension cycle of 72° C. for 10 min was carried out, followed by reaction termination at 4° C. The 430 bp PCR fragment was subcloned into the pGEM-T easy vector (Promega) to generate pT17(1-4).

Using the ligated "Pool 2" mixture (i.e., D17-5AB, D17-6AB, D17-7AB and D17-8AB) as template, and oligonucleotides D17-5 (SEQ ID NO:72) and D17-8D (SEQ ID NO:73) as primers, the second portion of the codon-optimized Δ17 desaturase gene was amplified similarly by PCR and cloned into pGEM-T-easy vector to generate pT17(5-8). Finally, using the "Pool 3" ligation mixture (i.e., D17-9AB, D17-10AB and D17-11AB) as template, and oligonucleotides D17-8U (SEQ ID NO:74) and D17-11 (SEQ ID NO:75) as primers, the third portion of the codon-optimized Δ17 desaturase gene was amplified similarly by PCR and cloned into pGEM-T-easy vector to generate pT17(9-11).

E. coli was transformed separately with pT17(1-4), pT17(5-8) and pT17(9-11) and the plasmid DNA was isolated from ampicillin-resistant transformants. Plasmid DNA was purified and digested with the appropriate restriction endonucleases to liberate the 420 bp NcoI/BglII fragment of pT17(14), the 400 bp BglII/SalI fragment of pT17(5-8) and the 300 bp SalI/NotI fragment of pT17(9-11). These fragments were then combined, ligated together and used as template for amplification of the entire synthetic codon-optimized Δ17 desaturase gene using D17-1 (SEQ ID NO:70) and D17-11 (SEQ ID NO:75) as primers. The PCR amplification was carried out in a 50 μl total volume, using the conditions described above for each portion of the Δ17 desaturase gene and the thermocycling program as follows: initial denaturation at 95° C. for 3 min, followed by 35 cycles of the following: 95° C. for 1 min, 56° C. for 30 sec, 72° C. for 1.1 min. A final extension cycle of 72° C. for 10 min was carried out, followed by reaction termination at 4° C. This generated a 1.1 kB PCR product.

Construction of Plasmid pYSD17S Containing the Codon-Optimized Δ17 Desaturase

Figures 10A, 10B:
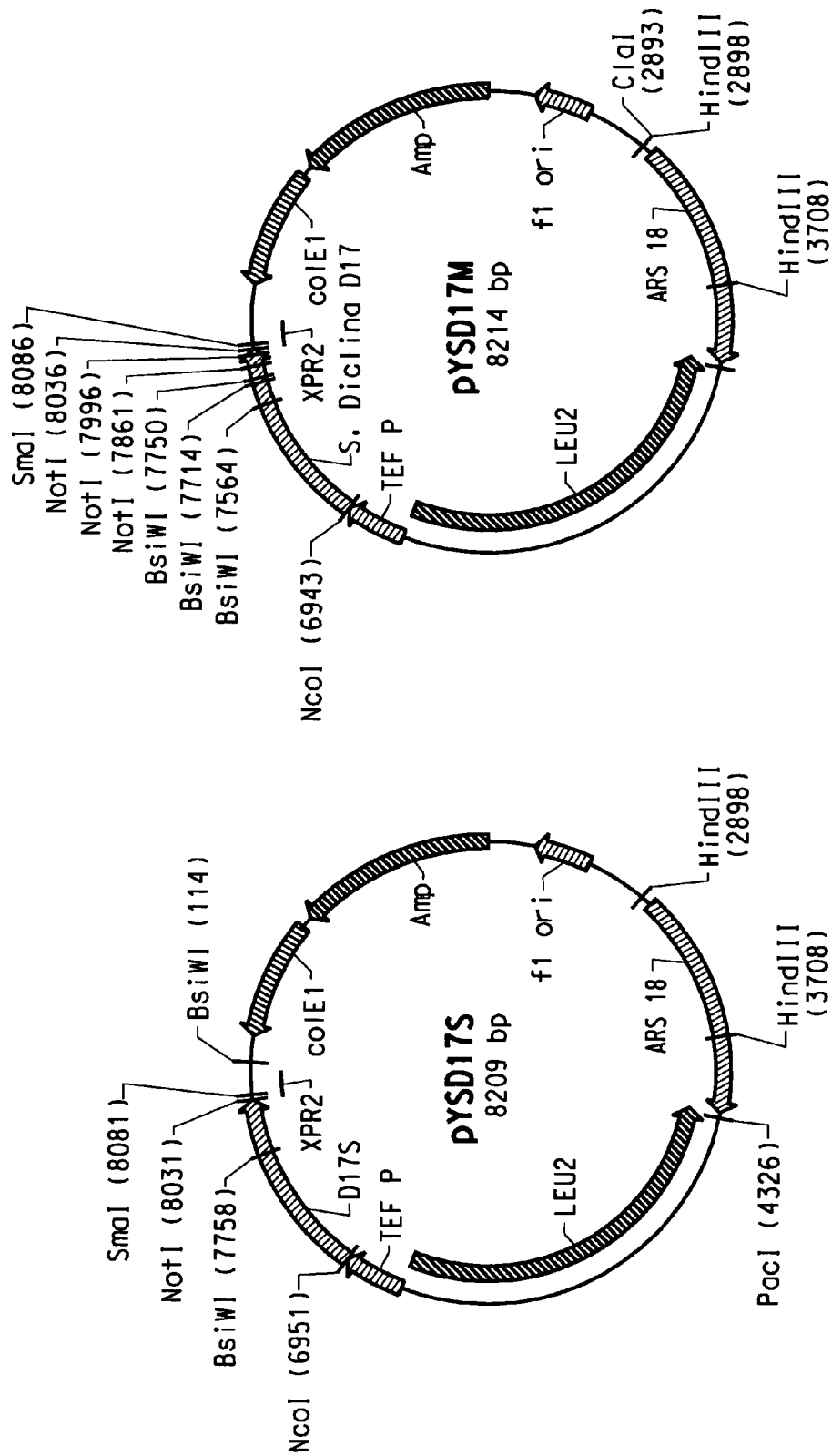
FIG. 10 shows plasmids for expression of the synthetic codon-optimized and wildtype Δ17 desaturase genes in *Y. lipolytica*.

The 1.1 kB PCR product comprising the entire synthetic Δ17-desaturase was digested with NcoI/NotI and subcloned into NcoI/NotI-digested pY5-13 (Example 1) to generate pYSD17S (FIG. 10A).

As an additional "control", to compare the efficiency of the wild type and synthetic genes in Yarrowia, the AT-rich PacI site in pYSD17 (comprising the wild-type gene; described in Example 5) was eliminated by site-directed mutagenesis using YL53 (SEQ ID NO:76) and YL54 (SEQ ID NO:77) as primers to generate pYSD17M (FIG. 10B).

Transformation of Yarrowia lipolytica with the Codon-Optimized Δ17 Desaturase Gene Plasmids containing the wildtype and codon-optimized Δ17 desaturase were transformed separately into Y. lipolytica ATCC #76982 according to the methods described above in Example 5. Using this technique, transformants were obtained that contained the following plasmids:

TABLE 10

Summary Of Plasmids In Transformant Yarrowia

| Plasmid | Description |
|---|---|
| pYSD17 | wildtype Δ17 desaturase |
| pYSD17M | wildtype Δ17 desaturase, minus AT-rich PacI site |
| pYSD17S | codon-optimized Δ17 desaturase |

Percent Substrate Conversion with the Codon-Optimized Δ17 Desaturase Gene

Δ17 desaturase converts ARA to EPA (see FIG. 2). The percent substrate conversion ([product]/[substrate+product] *100) of the wildtype and codon-optimized Δ17 desaturase genes was determined in Yarrowia lipolytica containing each alternate plasmid construct, using the methodology described in Example 5.

Figure 11A:
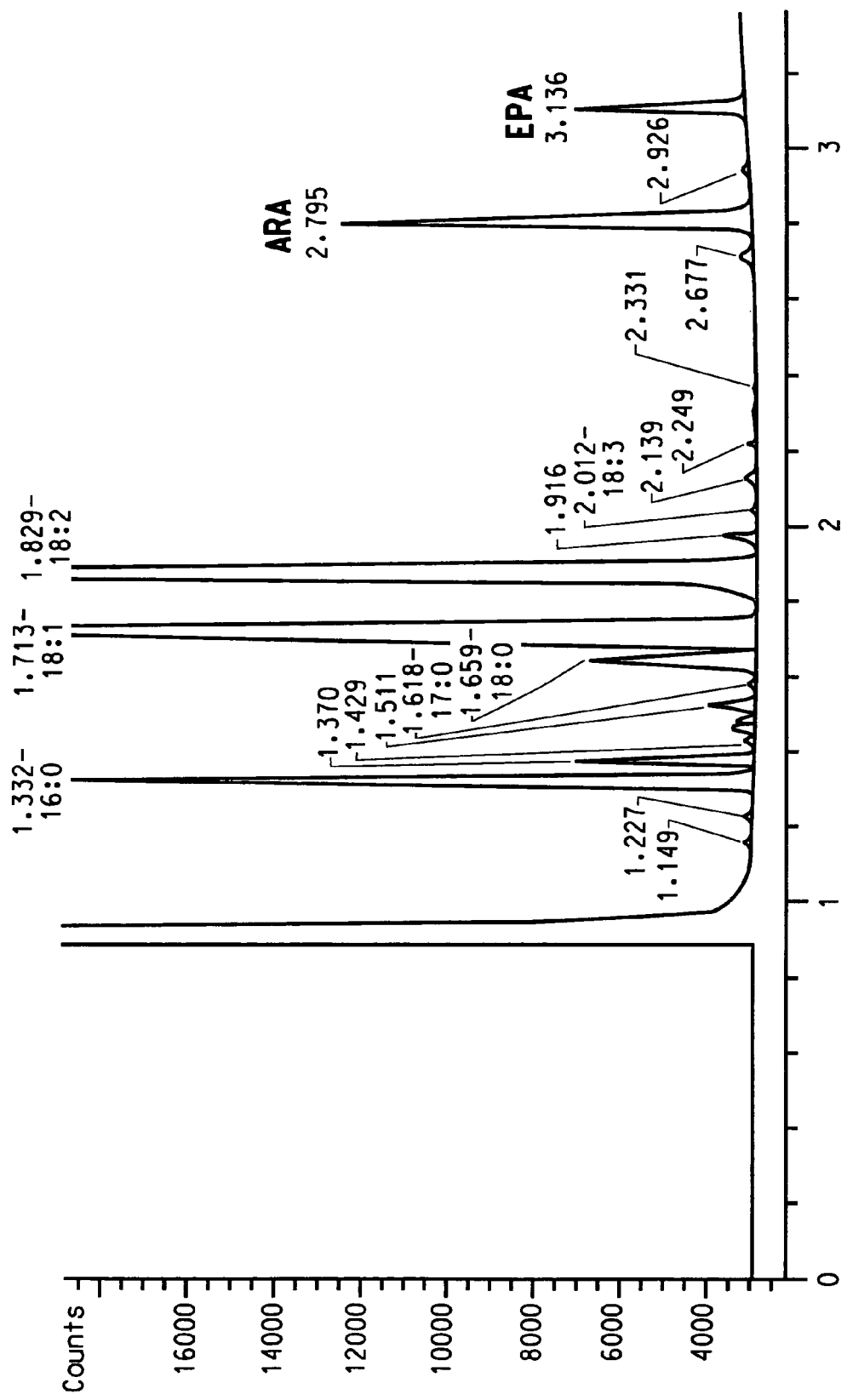
FIGS. 11A and 11B show the results of gas chromatographic analysis of fatty acids produced in *Y. lipolytica* transformed with the wildtype and synthetic codon-optimized Δ17 desaturase genes, respectively.
Figure 11B:
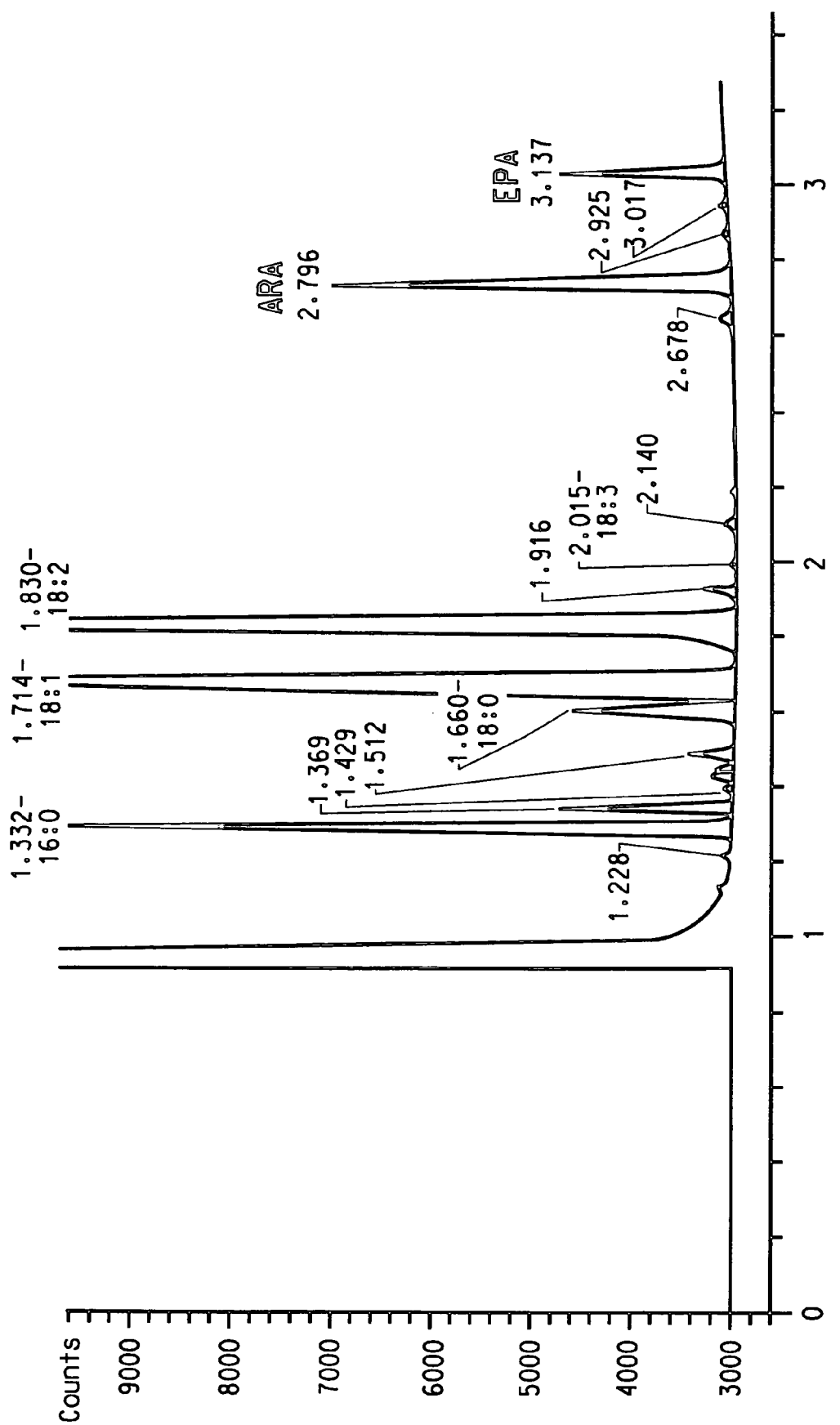

The results of the ARA feeding experiments showed that Yarrowia strains with control plasmids pYSD17 or pYSD17M converted about 23% of intracellular ARA to EPA (FIG. 11A) while those containing the codon-optimized Δ17 desaturase gene within pYSD17S converted about 45% of intracellular ARA to EPA (FIG. 11B). Thus, Yarrowia containing the codon-optimized Δ17 desaturase converted about 2-fold more ARA than the strains containing the wild type S. diclina gene.

Example 7

Construction of Plasmids Suitable for the Coordinate Expression of Multiple Omega Fatty Acid Biosynthesis Genes in Yarrowia lipolytica A variety of expression plasmids were constructed to produce a construct comprising a Δ6 desaturase, elongase, Δ5 desaturase, and Δ17 desaturase that would be suitable to integrate into the Y. lipolytica genome. Expression of this construct was necessary to test the hypothesize that "pure" ω-3 PUFAs, without co-synthesis of any ω-6 PUFAs, could be produced in a Y. lipolytica host containing a disrupted native Δ12 desaturase (infra, Example 8).

Construction of Plasmid pY24

Figure 12:
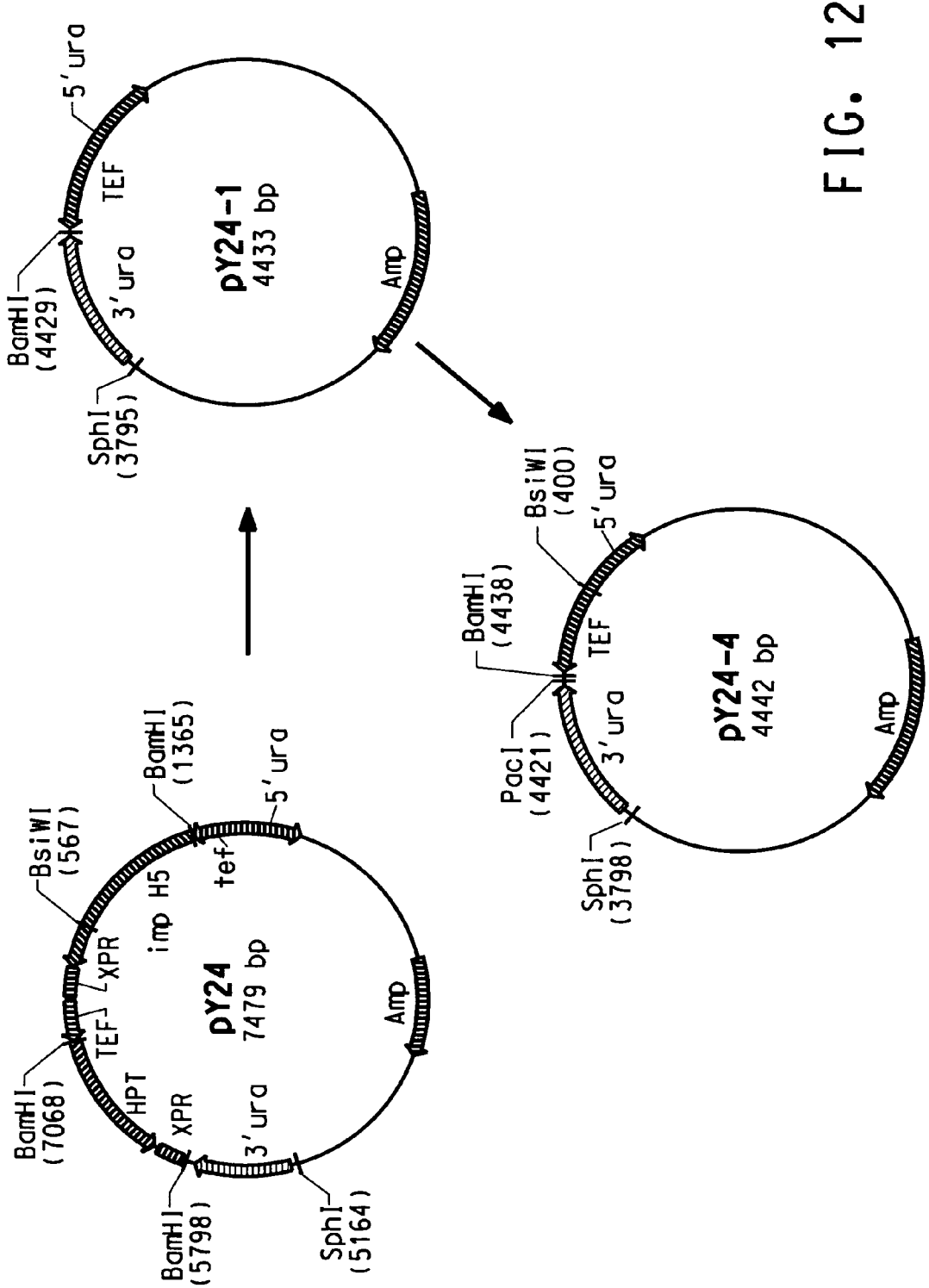
FIG. 12 is a schematic presentation of the construction of intermediate vector pY24-4.

Plasmid pY24 (FIG. 12) was a parent vector for construction of expression cassettes suitable for integration into the genome of Yarrowia lipolytica. pY24 was constructed as follows:

Using oligonucleotides KU5 and KU3 (SEQ ID NOs:78 and 79) as primers and *Yarrowia* genomic DNA as template, a 1.7 kB DNA fragment (SEQ ID NO:80) containing the *Yarrowia* URA3 gene was PCR amplified. The PCR amplification was carried out in a 50 µl total volume containing: 100 ng *Yarrowia* genomic DNA, PCR buffer containing 10 mM KCl, 10 mM $(NH_4)_2SO_4$, 20 mM Tris-HCl (pH 8.75), 2 mM $MgSO_4$, 0.1% Triton X-100, 100 µg/mL BSA (final concentration), 200 µM each deoxyribonucleotide triphosphate, 10 pmole of each primer and 1 µl of PfuTurbo DNA polymerase (Stratagene, San Diego, Calif.). Amplification was carried out as follows: initial denaturation at 95° C. for 3 min, followed by 35 cycles of the following: 95° C. for 1 min, 56° C. for 30 sec, 72° C. for 2 min. A final extension cycle of 72° C. for 10 min was carried out, followed by reaction termination at 4° C. The PCR product was inserted into pGEM-T easy vector (Promega, Madison, Wis.) to generate pGYUM.

Using oligonucleotides KI5 and KI3 (SEQ ID NOs:82 and 83), a 1.1 kB DNA fragment (SEQ ID NO:84) containing the conjugase gene (or "imp H8") of *Impatients balsama* (clone ids.pk0001.h8; E. I. du Pont de Nemours and Company, Inc., Wilmington, Del.) was PCR amplified. The PCR amplification was carried out using the components described above, with the exception that 10 ng plasmid DNA of ids.pk0001.h8 was used as template. Amplification was carried out as follows: initial denaturation at 95° C. for 3 min, followed by 35 cycles of the following: 95° C. for 1.5 min, 56° C. for 30 sec, 72° C. for 1.2 min. A final extension cycle of 72° C. for 10 min was carried out, followed by reaction termination at 4° C. The PCR products were digested with NotI, and then inserted into the NotI site of pY5 (FIG. 3) to generate pY9.

Using oligonucleotides KTI5 and KTI3 (SEQ ID NOs:86 and 87), a 1.7 kB DNA fragment (SEQ ID NO:88) containing the TEF::IMP H8::XPR chimeric gene of pY9 was PCR amplified. The PCR amplification was carried out as described above, with the exception that 10 ng plasmid DNA of pGYUM was used as template. Amplification was carried out as follows: initial denaturation at 95° C. for 3 min, followed by 35 cycles of the following: 95° C. for 1 min, 56° C. for 30 sec, 72° C. for 2 min. A final extension cycle of 72° C. for 10 min was carried out, followed by reaction termination at 4° C. The PCR products were inserted into PCR-Script (Stratagene) to generate pY9R. The 1.7 kB Xho/EcoRV fragment of pY9R was exchanged with the XhoI/EcoRV fragment of pGYUM to generate pY21.

Using oligonucleotides KH5 and KH3 (SEQ ID NOs:90 and 91) as primers and genomic DNA of KS65 as template, a 1 kB DNA fragment (SEQ ID NO:92) containing the *E. coli* hygromycin resistance gene ("HPT"; Kaster, K. R., et al., *Nucleic Acids Res.* 11:6895-6911 (1983)) was PCR amplified. The PCR amplification was carried out in a 50 µl total volume using the components described above, with the exception that 10 ng plasmid DNA of ids.pk0001.h8 was used as template. Amplification was carried out as follows: initial denaturation at 95° C. for 3 min, followed by 35 cycles of the following: 95° C. for 1 min, 56° C. for 30 sec, 72° C. for 1.2 min. A final extension cycle of 72° C. for 10 min was carried out, followed by reaction termination at 4° C. The PCR products were digested with NotI and then inserted into the NotI site of pY5 (FIG. 3) to generate pTHPT-1.

Using oligonucleotides KTH5 and KTH3 (SEQ ID NOs:94 and 95) as primers and pTHPT-1 plasmid DNA as template, a 1.6 kB DNA fragment (SEQ ID NO:96) containing the TEF::HPT::XPR fusion gene was amplified as described above. The PCR products were digested with BglII and then inserted into pY21 to generate pY24.

Construction of pY24-4

Plasmid pY24 (FIG. 12) was used for construction of expression cassettes suitable for integration into the *Y. lipolytica* genome. The 401 bp of 5'-sequence (SEQ ID NO:98) and 568 bp of 3'-sequence (SEQ ID NO:99) from the *Yarrowia lipolytica* URA3 gene in pY24 plasmid were used to direct integration of expression cassettes into the Ura loci of the *Yarrowia* genome. Two chimeric genes (TEF::HPT::XPR and TEF::IMP H8::XPR) were first removed from pY24 by digestion with BamHI and self-ligation to generate pY24-1. PacI and BsiWI sites were introduced into pY24-1 by site-directed mutagenesis using YL63 and YL64 (SEQ ID NOs:100 and 101) and YL65 and YL66 (SEQ ID NOs:102 and 103) primer pairs, respectively, to generate pY24-4.

Construction of an Integration Vector for Expression of Δ5 Desaturase

The 4261 bp PacI/BsiWI fragment of pYMA5pb (comprising the *M. alpina* Δ5 desaturase gene; described in Example 5) was ligated into the PacI/BsiWI sites of pY24-4 (FIG. 12) to generate pYZM5 (FIG. 6). HindIII and ClaI sites were introduced into pYZM5 by site-directed mutagenesis using primer pairs YL81 and YL82 (SEQ ID NOs:104 and 105) and YL83 and YL84 (SEQ ID NOs:106 and 107), respectively, to generate pYZM5CH (FIG. 6). A PmeI site was introduced into pYZM5CH by site-directed mutagenesis using YL105 and YL106 (SEQ ID NOs:108 and 109) as primers to generate pYZM5CHPP. An AscI site was introduced into pYZM5CHPP by site-directed mutagenesis using YL119 and YL120 (SEQ ID NOs:110 and 111) as primers to generate pYZM5CHPPA (FIG. 6).

Figure 13A:
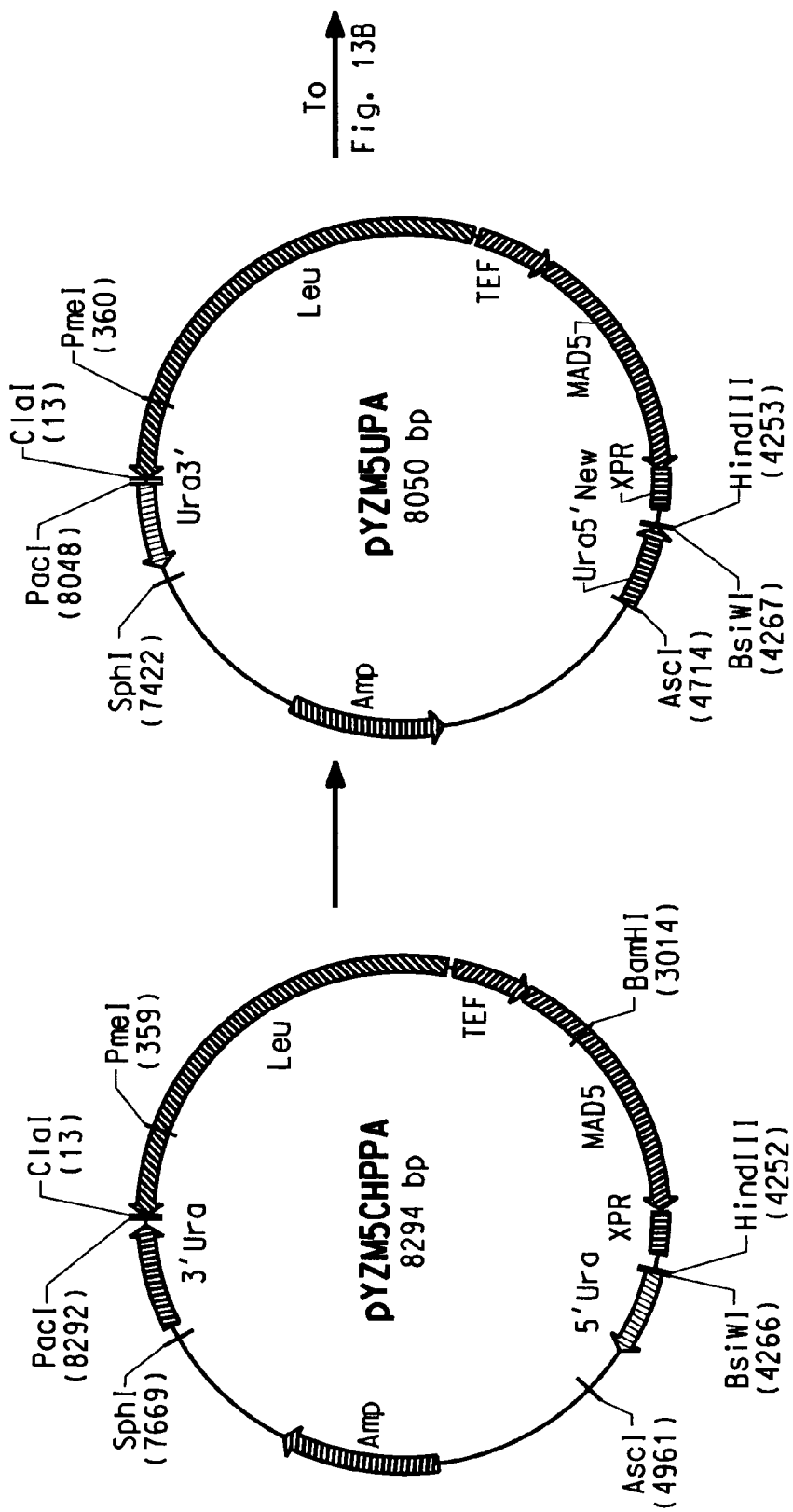
FIG. 13 is a schematic presentation of the construction of intermediate vector pYZV16.
Figure 13B:
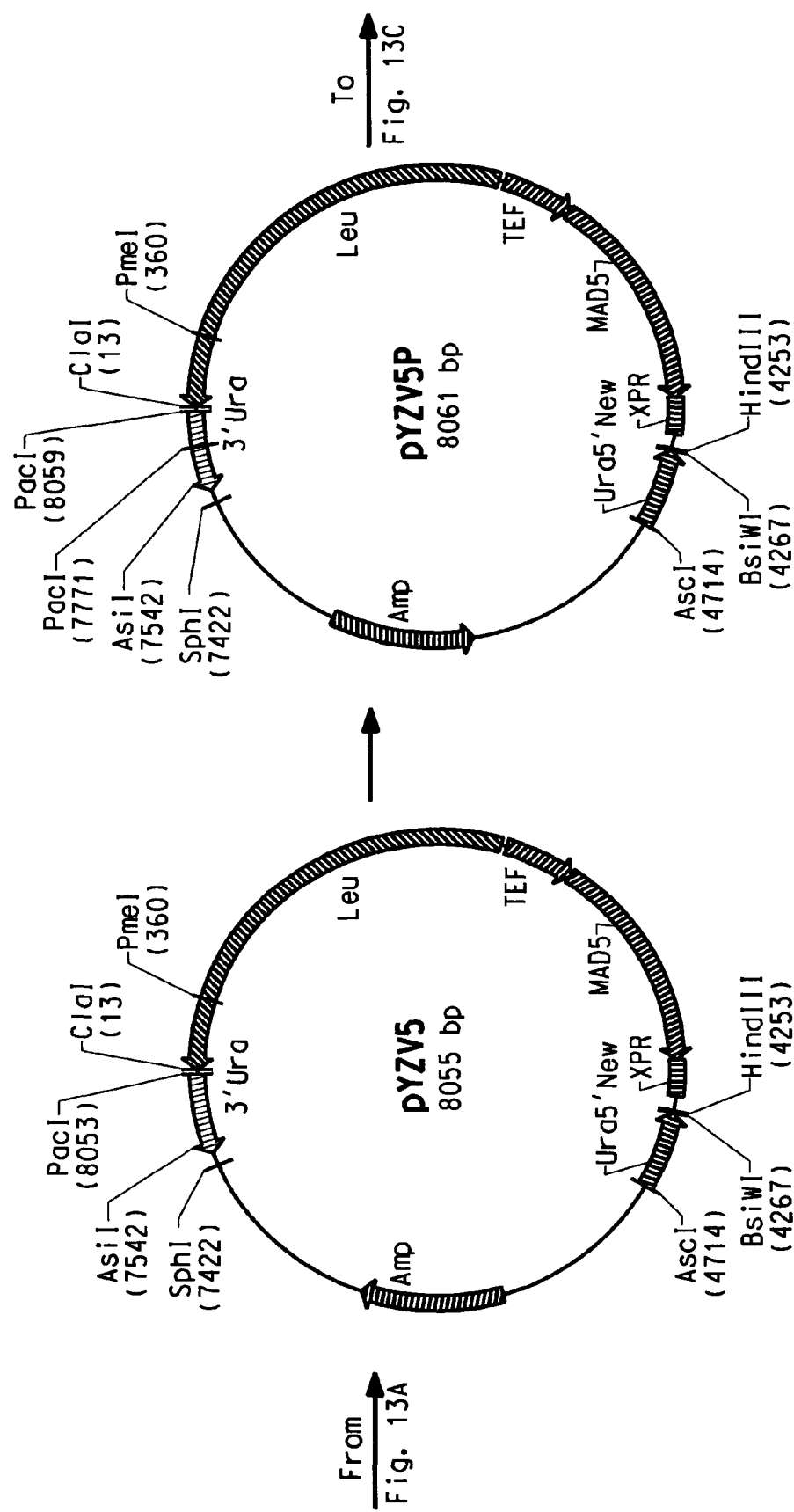
Figure 13C:
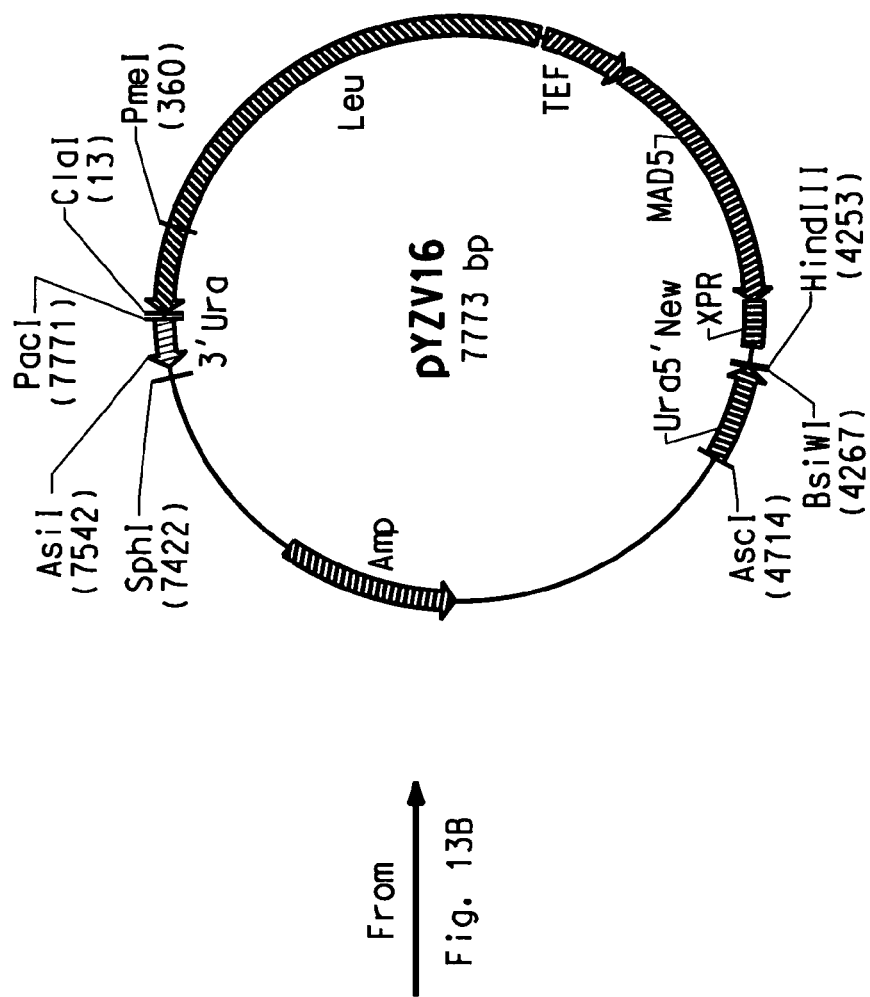

To optimize the integration vector, 440 bp of 5'-non-coding DNA sequence upstream from the *Yarrowia lipolytica* URA3 gene (SEQ ID NO:114) was amplified by PCR using YL121 and YL122 (SEQ ID NOs:112 and 113) as primers. The PCR product was digested with AscI and BsiWI and then exchanged with the AscI/BsiWI fragment of pYZM5CHPPA (FIGS. 6 and 13) to generate pYZM5UPA (FIG. 13). An AscI site was introduced into pYZM5UPA by site-directed mutagenesis using oligonucleotides YL114 and YL115 (SEQ ID NOs:115 and 116) to generate pYZV5. In order to reduce the size of the 3'-non-coding region of the URA3 gene in pYZV5, a second PacI site was introduced into the middle of this region by site-directed mutagenesis using oligonucleotides YL114 and YL115 (described above) to generate pYZV5P. The PacI fragment of pYZV5P was excised by digestion with PacI and religation to generate pYZV16 (FIG. 13). Digestion of pYZV16 with AscI liberates a 5.2 kB DNA fragment (SEQ ID NO:117) suitable for integration and expression of the Δ5 desaturase gene ("MAD5") in the *Y. lipolytica* genome.

Figure 14A:
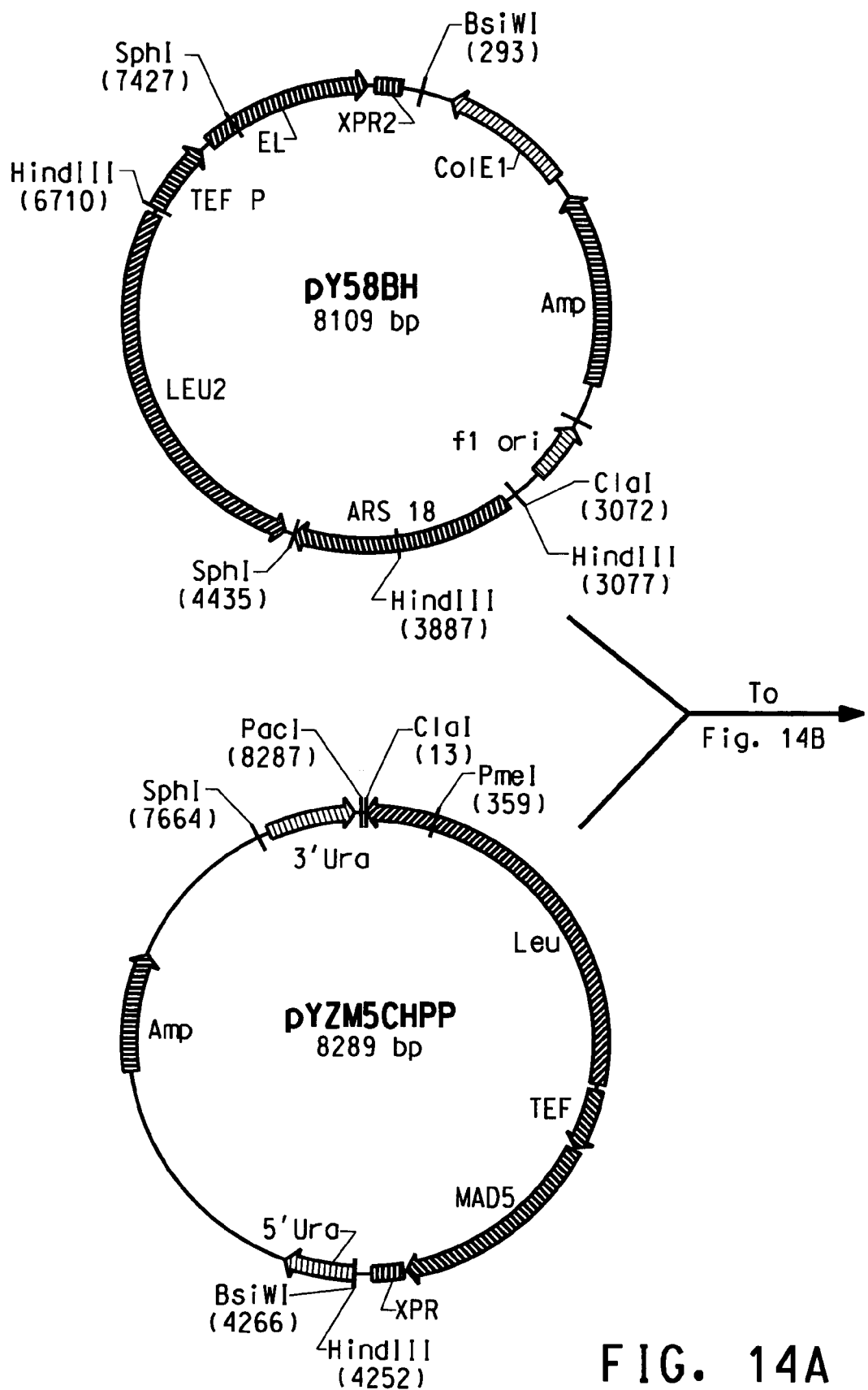
FIG. 14 is a schematic presentation of the construction of integration vector pYZM5EL6.
Figure 14B:
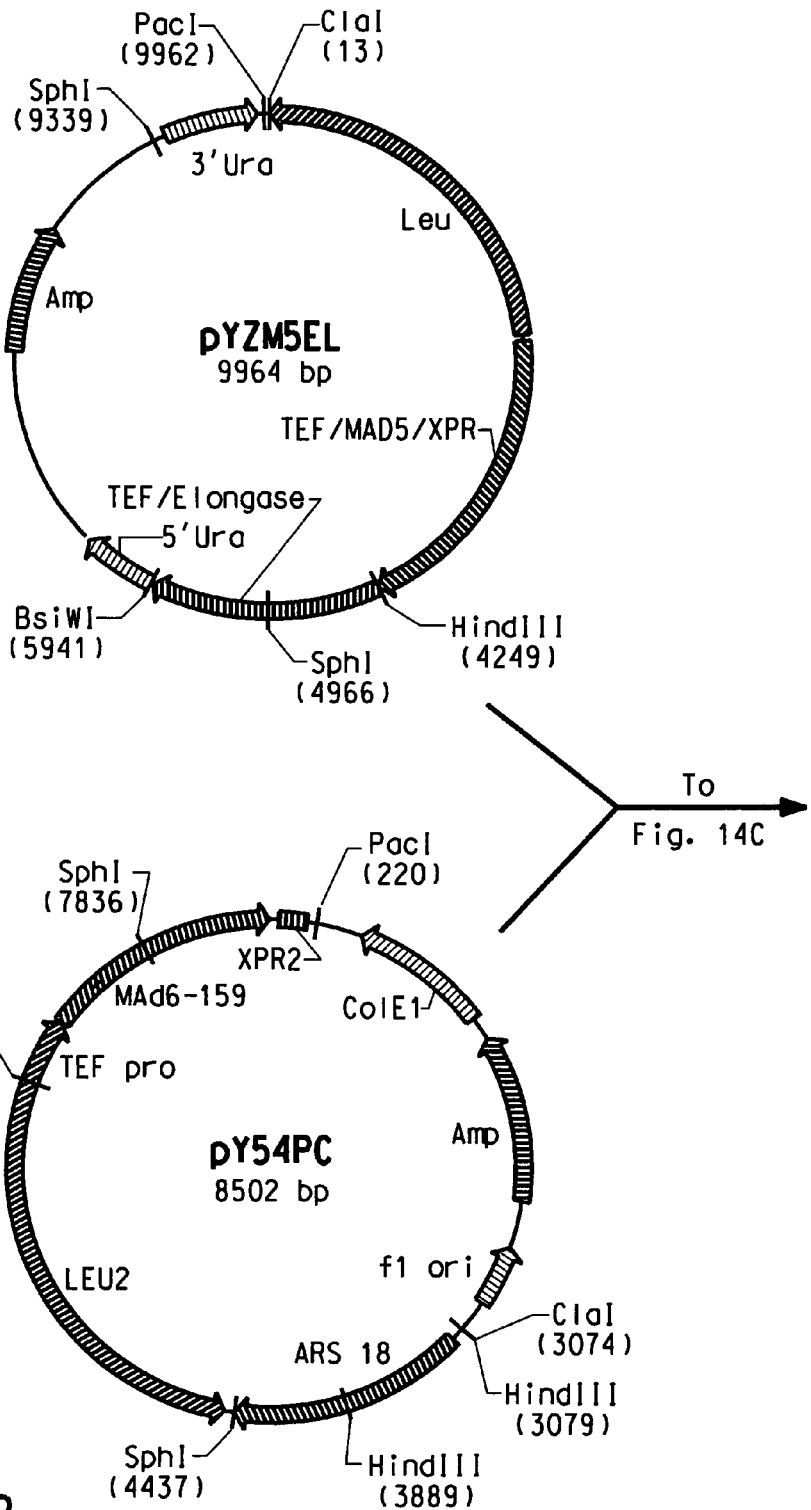
Figure 14C:
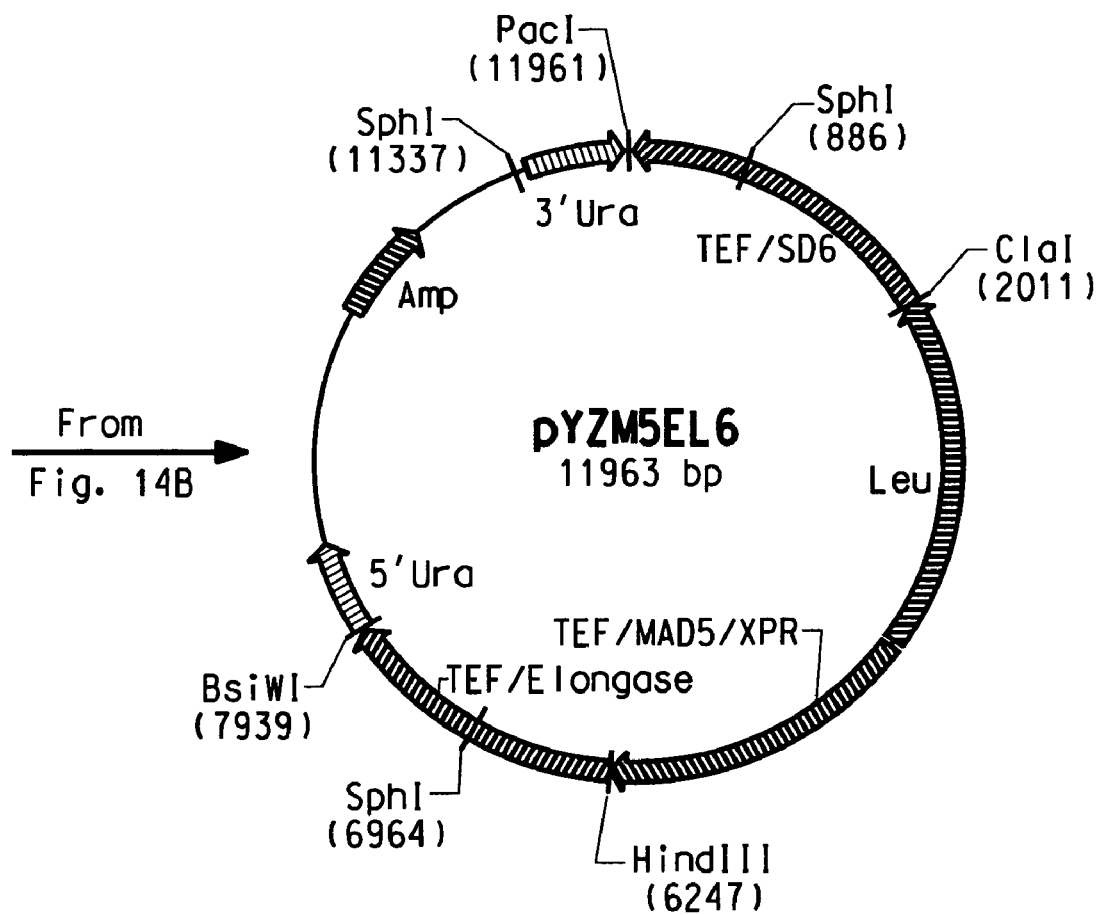

Construction of an Integration Vector for Expression of the High Affinity Elongase and Δ5 Desaturase BsiWI and HindIII sites were introduced into pY58 (containing the coding region of the *M. alpina* high affinity PUFA elongase; described in Example 5) by site-directed mutagenesis using YL61 and YL62 (SEQ ID NOs:17 and 18) and YL69 and YL70 (SEQ ID NOs:118 and 119) primer pairs, respectively, to generate pY58BH (FIG. 14; elongase gene labeled as "EL"). The 1.7 kB BsiWI/HindIII fragment of pY58BH, which contains the TEF::EL::XPR chimeric gene, was ligated into the BsiWI/HindIII site of pYZM5CHPP (construction described in FIG. 6) to generate pYZM5EL (FIG. 14). This plasmid is suitable for integration and coordinate expression of the *M. alpina* Δ5 desaturase and high affinity PUFA elongase genes in *Y. lipolytica*.

Construction of an Integration Vector for Expression of the Δ6 Desaturase, High Affinity Elongase and Δ5 Desaturase PacI and ClaI sites were introduced into pY54 (containing the *M. alpina* Δ6 desaturase; described in Example 5) by site-directed mutagenesis using YL77 and YL78 (SEQ ID NOs:120 and 121) and YL79A and YL80A (SEQ ID NOs:122 and 123) primer pairs, respectively, to generate pY54PC (FIG. 14; Δ6 desaturase gene labeled as "MAD6"). The 2 kB ClaI/PacI DNA fragment of pY54PC, which contains the TEF::MAD6::XPR chimeric gene, was ligated into the ClaI/PacI sites of pYZM5EL to generate pYZM5EL6 (FIG. 14). This plasmid is suitable for integration and coordinate expression of the M. alpina Δ6 desaturase, Δ5 desaturase and high affinity PUFA elongase genes in the Y. lipolytica genome.

Construction of a DNA Fragment Suitable for Integration into the Yarrowia Genome, for Expression of the Δ6 Desaturase, PUFA Elongase and Δ5 Desaturase The plasmid pYZV16 (construction described in FIG. 13) was used for construction of plasmids containing multiple expression cassettes.

Figure 15A:
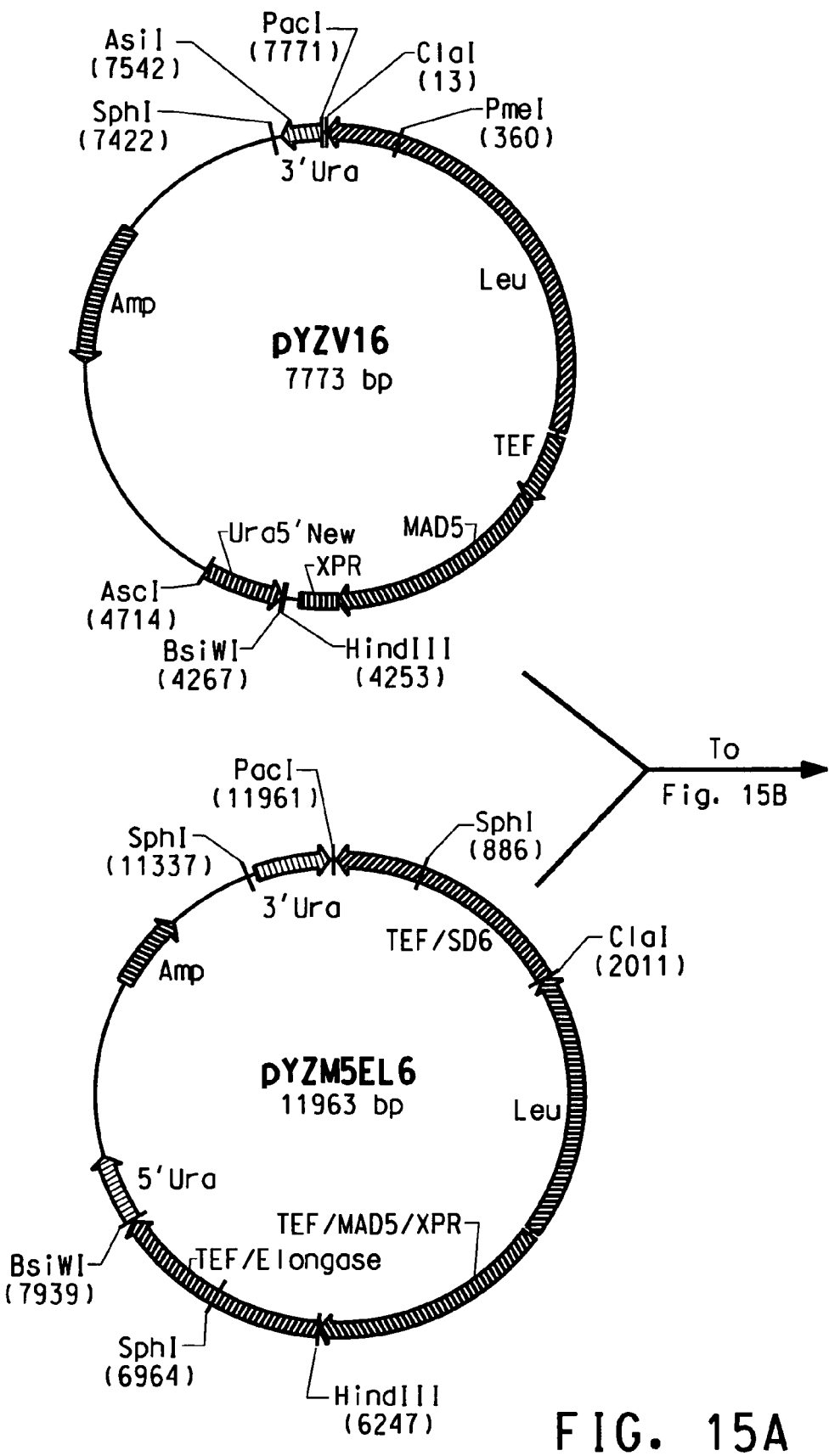
FIG. 15 is a schematic presentation of the construction of integration vectors pYZV5EL6 and pYZV5EL6/17.
Figure 15B:
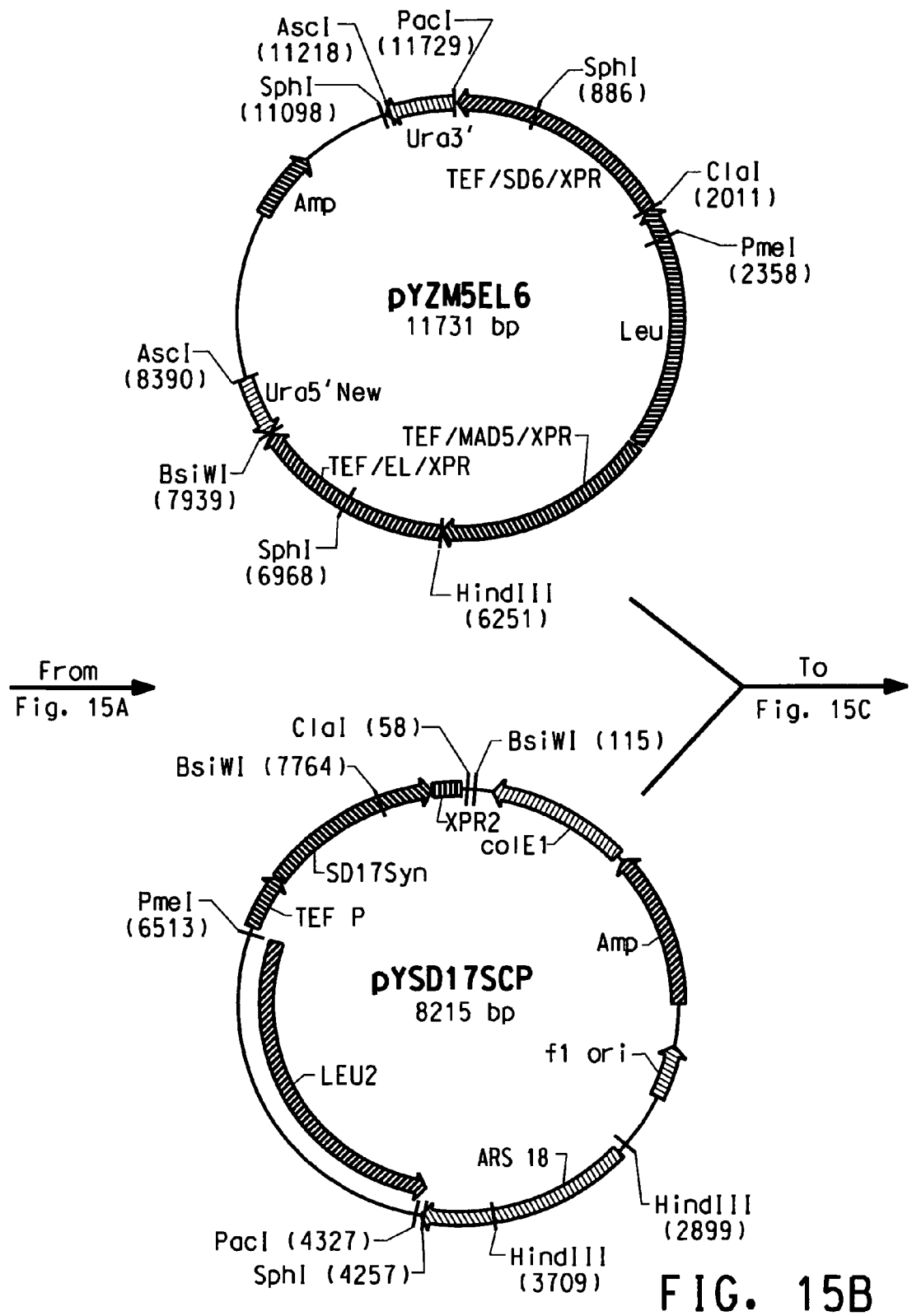
Figure 15C:
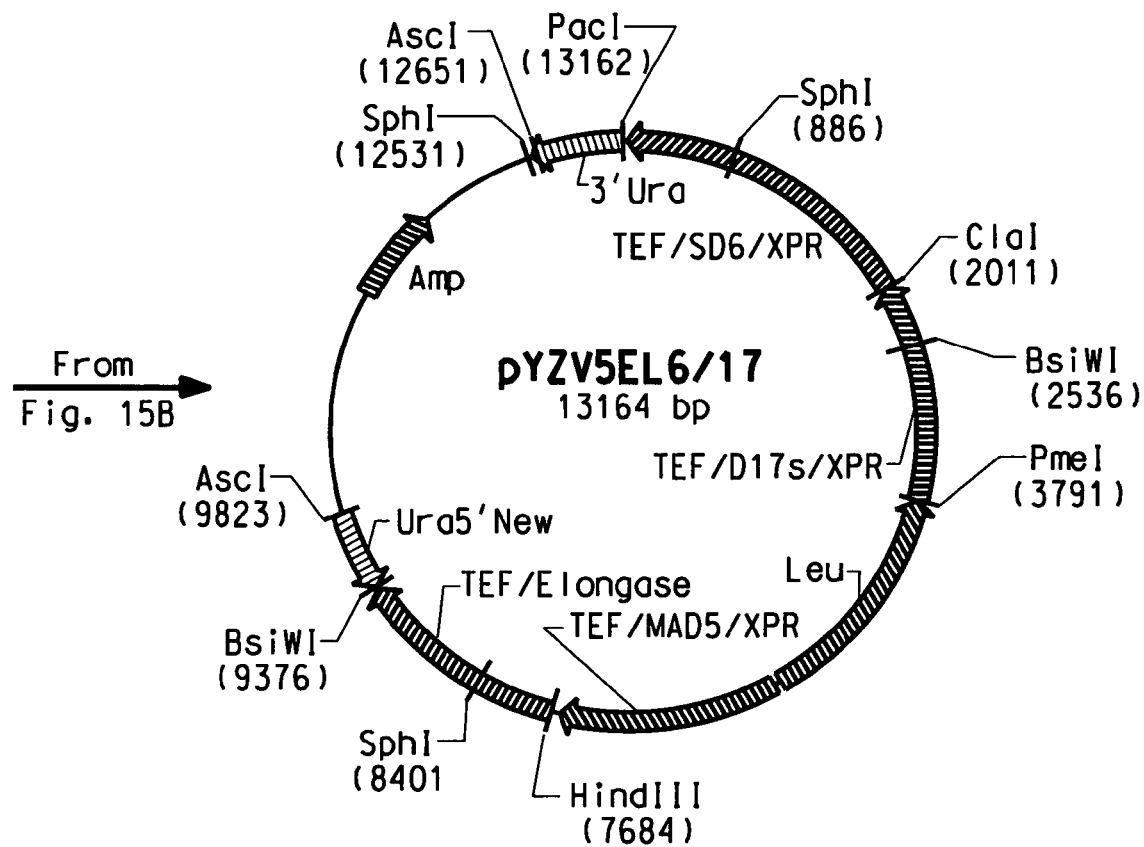

First, the 3.5 kB BsiWI/PacI fragment of pYZV16 was ligated to the 7.9 kB BsiWI/PacI fragment of pYZM5EL6 (construction described in FIG. 14) to generate pYZV5EL6 (FIG. 15). Digestion of pYZV5EL6 with AscI liberates a 8.9 kB DNA fragment (SEQ ID NO:124) suitable for integration and coordinate expression of the Δ6 desaturase, PUFA elongase and Δ5 desaturase genes in the Y. lipolytica genome.

Construction of a DNA Fragment Suitable for Integration into the Yarrowia Genome, for Expression of the Δ6 Desaturase, PUFA Elongase, Δ5 Desaturase and Δ17 Desaturase A synthetic S. diclina Δ17 desaturase gene was inserted into the NcoI/NotI sites of pY5-13 to generate pYSD17S (FIG. 1A). ClaI and PmeI sites were introduced into pYSD17S by site-directed mutagenesis using YL101 and YL102 (SEQ ID NOs:125 and 126) and YL103 and YL104 (SEQ ID NOs:127 and 128) primer pairs, respectively, to generate pYSD17SPC (FIG. 15).

The 347 bp ClaI/PmeI fragment of pYZV5EL6 (FIG. 15) was exchanged with the 1760 bp ClaI/PmeI fragment from pYSD17SPC containing the Δ17 desaturase expression cassette to generate pYZV5E6/17. Digestion of pYZV5E6/17 with AscI liberates a 10.3 kB DNA fragment (SEQ ID NO:129) suitable for integration and coordinate expression of the Δ6 desaturase, PUFA elongase, Δ5 desaturase and Δ17 desaturase genes in the Y. lipolytica genome.

Example 8

Use of Δ12 Desaturase Disrupted Strains for the Production of Pure Omega-3 Fatty Acids by Substrate Feeding The present Example describes the utility of a Δ12 desaturase-disrupted Yarrowia lipolytica host strain containing appropriate heterologous genes (e.g., a Δ6 desaturase, elongase, Δ5 desaturase, Δ17 desaturase, as described in Example 7) for the production of ω-3 PUFAs, without co-synthesis of any ω-6 PUFAs. Feeding studies were performed with ALA as the substrate. The results demonstrate that it is possible to produce ω-3 PUFAs in the absence of ω-6 PUFAs.

Feeding Studies

Wildtype Yarrowia lipolytica ATCC #76982 was transformed with an integrating 10.3 kB DNA fragment (SEQ ID NO:129) containing a Δ6 desaturase, PUFA elongase, Δ5 desaturase and Δ17 desaturase (from Example 7). This resulted in creation of strain "WT+4G". Then, the Δ12 desaturase was disrupted in strain WT+4G, as described in Example 2. This resulted in creation of strain "D12KO+4G".

Cells from each of the four strains listed below in Table 11 (100 μl) were grown in 3 mL minimal media containing no substrate addition, 10 μg of LA, 10 ug ALA, or 5 ug each of LA and ALA for about 24 hr at 30° C.

TABLE 11

Description Of Strains Tested In The Feeding Studies

| Strain Designation | Strain Description | Example |
|---|---|---|
| WT | wild-type Yarrowia lipolytica ATCC #76982 | — |
| WT + 4G | wild-type Yarrowia lipolytica, containing a Δ6 desaturase, PUFA elongase, Δ5 desaturase and Δ17-desaturase | 8 |
| D12KO | Δ12 desaturase-disrupted Yarrowia lipolytica | 2 |
| D12KO + 4G | Δ12 desaturase-disrupted Yarrowia lipolytica, containing a Δ6 desaturase, PUFA elongase, Δ5 desaturase and Δ17 desaturase | 8 |

Fatty acid composition was determined by direct transesterification, as described in the General Methods. The fatty acid profile of each of the strains grown with no substrate addition, 10 μg of LA, 10 ug ALA, or 5 ug each of LA and ALA are shown below in Table 12. Fatty acids are identified as 16:0, 16:1, 18:0, 18:1 (oleic acid), 18:2 (LA), GLA, DGLA, ALA, and STA. The composition of each is presented as a % of the total fatty acids.

TABLE 12

Fatty Acid Composition (% Of Total Fatty Acids)

| Strain | FA feed | 16:0 | 16:1 | 18:0 | 18:1 | 18:2 | GLA | DGLA | ALA | STA |
|---|---|---|---|---|---|---|---|---|---|---|
| WT | None | 10 | 6 | 8 | 50 | 21 | nd | nd | nd | nd |
| WT | LA | 11 | 3 | 6 | 30 | 47 | nd | nd | nd | nd |
| WT | ALA | 9 | 3 | 4 | 29 | 5 | nd | nd | 48 | nd |
| D12KO | None | 10 | 7 | 8 | 68 | nd | nd | nd | nd | nd |
| D12KO | LA | 9 | 4 | 5 | 26 | 53 | nd | nd | nd | nd |
| D12KO | ALA | 10 | 4 | 6 | 41 | nd | nd | nd | 35 | nd |
| WT + 4G | None | 11 | 6 | 7 | 57 | 6 | 5 | 0.9 | nd | nd |
| WT + 4G | LA | 11 | 3 | 6 | 32 | 31 | 9 | 1.0 | nd | nd |
| WT + 4G | ALA | 9 | 3 | 5 | 31 | 2 | 1 | 0.2 | 40 | 4 |
| WT + 4G | LA + A | 6 | 1 | 2 | 10 | 33 | 4 | 0.3 | 39 | 2 |
| D12KO + 4G | None | 9 | 6 | 8 | 69 | nd | nd | nd | nd | nd |

TABLE 12-continued

| | Fatty Acid Composition (% Of Total Fatty Acids) | | | | | | | | |
|---|---|---|---|---|---|---|---|---|---|
| Strain | FA feed | 16:0 | 16:1 | 18:0 | 18:1 | 18:2 | GLA | DGLA | ALA | STA |
| D12KO + 4G | LA | 8 | 2 | 6 | 24 | 45 | 10 | 1.0 | nd | nd |
| D12KO + 4G | ALA | 8 | 5 | 5 | 45 | nd | nd | nd | 27 | 4 |
| D12KO + 4G | LA + A | 7 | 2 | 4 | 14 | 26 | 4 | 0.3 | 37 | 3 |

*nd = not detectable

The results showed that feeding ALA to D12 KO cells resulted in the production of only ω-3 fatty acids (i.e., ALA and STA), without biosynthesis of any ω-6 fatty acids (i.e., GLA or DGLA).

---

SEQUENCE LISTING

<160> NUMBER OF SEQ ID NOS: 130

<210> SEQ ID NO 1
<211> LENGTH: 19
<212> TYPE: DNA
<213> ORGANISM: Artificial Sequence
<220> FEATURE:
<223> OTHER INFORMATION: Primer TEF5'

<400> SEQUENCE: 1
agagaccggg ttggcggcg                                            19

<210> SEQ ID NO 2
<211> LENGTH: 30
<212> TYPE: DNA
<213> ORGANISM: Artificial Sequence
<220> FEATURE:
<223> OTHER INFORMATION: Primer TEF3'

<400> SEQUENCE: 2
ttggatcctt tgaatgattc ttatactcag                                30

<210> SEQ ID NO 3
<211> LENGTH: 29
<212> TYPE: DNA
<213> ORGANISM: Artificial Sequence
<220> FEATURE:
<223> OTHER INFORMATION: Primer XPR5'

<400> SEQUENCE: 3
tttccgcggc ccgagattcc ggcctcttc                                 29

<210> SEQ ID NO 4
<211> LENGTH: 31
<212> TYPE: DNA
<213> ORGANISM: Artificial Sequence
<220> FEATURE:
<223> OTHER INFORMATION: Primer XPR3'

<400> SEQUENCE: 4
tttccgcgga cacaatatct ggtcaaattt c                              31

<210> SEQ ID NO 5
<211> LENGTH: 30
<212> TYPE: DNA
<213> ORGANISM: Artificial Sequence
<220> FEATURE:
<223> OTHER INFORMATION: Primer YL1

<400> SEQUENCE: 5
cagtgccaaa agccaaggca ctgagctcgt                                                   30

<210> SEQ ID NO 6
<211> LENGTH: 31
<212> TYPE: DNA
<213> ORGANISM: Artificial Sequence
<220> FEATURE:
<223> OTHER INFORMATION: Primer YL2

<400> SEQUENCE: 6
gacgagctca gtgccttggc ttttggcact g                                                 31

<210> SEQ ID NO 7
<211> LENGTH: 36
<212> TYPE: DNA
<213> ORGANISM: Artificial Sequence
<220> FEATURE:
<223> OTHER INFORMATION: Primer YL3

<400> SEQUENCE: 7
gtataagaat cattcaccat ggatccacta gttcta                                            36

<210> SEQ ID NO 8
<211> LENGTH: 36
<212> TYPE: DNA
<213> ORGANISM: Artificial Sequence
<220> FEATURE:
<223> OTHER INFORMATION: Primer YL4

<400> SEQUENCE: 8
tagaactagt ggatccatgg tgaatgattc ttatac                                            36

<210> SEQ ID NO 9
<211> LENGTH: 36
<212> TYPE: DNA
<213> ORGANISM: Artificial Sequence
<220> FEATURE:
<223> OTHER INFORMATION: Primer YL23

<400> SEQUENCE: 9
atggatccac tagttaatta actagagcgg ccgcca                                            36

<210> SEQ ID NO 10
<211> LENGTH: 36
<212> TYPE: DNA
<213> ORGANISM: Artificial Sequence
<220> FEATURE:
<223> OTHER INFORMATION: Primer YL24

<400> SEQUENCE: 10
tggcggccgc tctagttaat taactagtgg atccat                                            36

<210> SEQ ID NO 11
<211> LENGTH: 39
<212> TYPE: DNA
<213> ORGANISM: Artificial Sequence
<220> FEATURE:
<223> OTHER INFORMATION: Primer YL5

<400> SEQUENCE: 11
cccccctcga ggtcgatggt gtcgataagc ttgatatcg                                         39

<210> SEQ ID NO 12
<211> LENGTH: 39
<212> TYPE: DNA

```
<213> ORGANISM: Artificial Sequence
<220> FEATURE:
<223> OTHER INFORMATION: Primer YL6

<400> SEQUENCE: 12
cgatatcaag cttatcgaca ccatcgacct cgaggggggg                                    39

<210> SEQ ID NO 13
<211> LENGTH: 35
<212> TYPE: DNA
<213> ORGANISM: Artificial Sequence
<220> FEATURE:
<223> OTHER INFORMATION: Primer YL9

<400> SEQUENCE: 13
tggtaaataa atgatgtcga ctcaggcgac gacgg                                         35

<210> SEQ ID NO 14
<211> LENGTH: 35
<212> TYPE: DNA
<213> ORGANISM: Artificial Sequence
<220> FEATURE:
<223> OTHER INFORMATION: Primer YL10

<400> SEQUENCE: 14
ccgtcgtcgc ctgagtcgac atcatttatt tacca                                         35

<210> SEQ ID NO 15
<211> LENGTH: 37
<212> TYPE: DNA
<213> ORGANISM: Artificial Sequence
<220> FEATURE:
<223> OTHER INFORMATION: Primer YL7

<400> SEQUENCE: 15
caaccgattt cgacagttaa ttaataattt gaatcga                                       37

<210> SEQ ID NO 16
<211> LENGTH: 37
<212> TYPE: DNA
<213> ORGANISM: Artificial Sequence
<220> FEATURE:
<223> OTHER INFORMATION: Primer YL8

<400> SEQUENCE: 16
tcgattcaaa ttattaatta actgtcgaaa tcggttg                                       37

<210> SEQ ID NO 17
<211> LENGTH: 33
<212> TYPE: DNA
<213> ORGANISM: Artificial Sequence
<220> FEATURE:
<223> OTHER INFORMATION: Primer YL61

<400> SEQUENCE: 17
acaattccac acaacgtacg agccggaagc ata                                           33

<210> SEQ ID NO 18
<211> LENGTH: 33
<212> TYPE: DNA
<213> ORGANISM: Artificial Sequence
<220> FEATURE:
<223> OTHER INFORMATION: Primer YL62

<400> SEQUENCE: 18
tatgcttccg gctcgtacgt tgtgtggaat tgt                                           33
```

<210> SEQ ID NO 19
<211> LENGTH: 26
<212> TYPE: DNA
<213> ORGANISM: Artificial Sequence
<220> FEATURE:
<223> OTHER INFORMATION: Degenerate primer P73
<220> FEATURE:
<221> NAME/KEY: misc_feature
<222> LOCATION: (24)..(24)
<223> OTHER INFORMATION: n is a, c, g, or t

<400> SEQUENCE: 19
tgggtcctgg gccaygartg yggnca                                          26

<210> SEQ ID NO 20
<211> LENGTH: 9
<212> TYPE: PRT
<213> ORGANISM: Artificial Sequence
<220> FEATURE:
<223> OTHER INFORMATION: Consensus sequence in delta12 desaturases

<400> SEQUENCE: 20

Trp Val Leu Gly His Glu Cys Gly His
1               5

<210> SEQ ID NO 21
<211> LENGTH: 30
<212> TYPE: DNA
<213> ORGANISM: Artificial Sequence
<220> FEATURE:
<223> OTHER INFORMATION: Degenerate primer P76
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 21
ggtggcctcc tcggcgtgrt araanggnat                                      30

<210> SEQ ID NO 22
<211> LENGTH: 10
<212> TYPE: PRT
<213> ORGANISM: Artificial Sequence
<220> FEATURE:
<223> OTHER INFORMATION: Consensus sequence in delta12 desaturases
<220> FEATURE:
<221> NAME/KEY: MISC_FEATURE
<222> LOCATION: (1)..(1)
<223> OTHER INFORMATION: Xaa = Met or Ile

<400> SEQUENCE: 22

Xaa Pro Phe Tyr His Ala Glu Glu Ala Thr
1               5                   10

<210> SEQ ID NO 23
<211> LENGTH: 1936
<212> TYPE: DNA
<213> ORGANISM: Yarrowia lipolytica
<220> FEATURE:
<221> NAME/KEY: CDS
<222> LOCATION: (283)..(1539)

<400> SEQUENCE: 23
cgtagttata tacaagaggt agatgcgtgc tggtgttaga ggggctctca ggattaggag     60

-continued

```
gaaaatttga cattggccct caacatataa cctcgggtgt gcctctgttt accctcagct       120
tttgcttgtc cccaagtcag tcacgccagg ccaaaaaggt tggtggattg acagggagaa       180
aaaaaaaagc ctagtgggtt taaactcgag gtaagacatt gaaatatata ccggtcggca       240
tcctgagtcc ctttctcgta ttccaacaga ccgaccatag aa atg gat tcg acc          294
                                              Met Asp Ser Thr
                                               1 acg cag acc aac acc ggc acc ggc aag gtg gcc gtg cag ccc ccc acg         342
Thr Gln Thr Asn Thr Gly Thr Gly Lys Val Ala Val Gln Pro Pro Thr
 5              10                  15                  20 gcc ttc att aag ccc att gag aag gtg tcc gag ccc gtc tac gac acc         390
Ala Phe Ile Lys Pro Ile Glu Lys Val Ser Glu Pro Val Tyr Asp Thr
                 25                  30                  35 ttt ggc aac gag ttc act cct cca gac tac tct atc aag gat att ctg         438
Phe Gly Asn Glu Phe Thr Pro Pro Asp Tyr Ser Ile Lys Asp Ile Leu
                 40                  45                  50 gat gcc att ccc cag gag tgc tac aag cgg tcc tac gtt aag tcc tac         486
Asp Ala Ile Pro Gln Glu Cys Tyr Lys Arg Ser Tyr Val Lys Ser Tyr
             55                  60                  65 tcg tac gtg gcc cga gac tgc ttc ttt atc gcc gtt ttt gcc tac atg         534
Ser Tyr Val Ala Arg Asp Cys Phe Phe Ile Ala Val Phe Ala Tyr Met
 70                  75                  80 gcc tac gcg tac ctg cct ctt att ccc tcg gct tcc ggc cga gct gtg         582
Ala Tyr Ala Tyr Leu Pro Leu Ile Pro Ser Ala Ser Gly Arg Ala Val
 85                  90                  95                  100 gcc tgg gcc atg tac tcc att gtc cag ggt ctg ttt ggc acc ggt ctg         630
Ala Trp Ala Met Tyr Ser Ile Val Gln Gly Leu Phe Gly Thr Gly Leu
                 105                 110                 115 tgg gtt ctt gcc cac gag tgt ggc cac tct gct ttc tcc gac tct aac         678
Trp Val Leu Ala His Glu Cys Gly His Ser Ala Phe Ser Asp Ser Asn
                 120                 125                 130 acc gtc aac aac gtc acc gga tgg gtt ctg cac tcc tcc atg ctg gtc         726
Thr Val Asn Asn Val Thr Gly Trp Val Leu His Ser Ser Met Leu Val
                 135                 140                 145 cct tac tac gcc tgg aag ctg acc cac tcc atg cac cac aag tcc act         774
Pro Tyr Tyr Ala Trp Lys Leu Thr His Ser Met His His Lys Ser Thr
 150                 155                 160 ggt cac ctc acc cgt gat atg gtg ttt gtg ccc aag gac cga aag gag         822
Gly His Leu Thr Arg Asp Met Val Phe Val Pro Lys Asp Arg Lys Glu
 165                 170                 175                 180 ttt atg gag aac cga ggc gcc cat gac tgg tct gag ctt gct gag gac         870
Phe Met Glu Asn Arg Gly Ala His Asp Trp Ser Glu Leu Ala Glu Asp
                 185                 190                 195 gct ccc ctc atg acc ctc tac ggc ctc atc acc cag cag gtg ttt gga         918
Ala Pro Leu Met Thr Leu Tyr Gly Leu Ile Thr Gln Gln Val Phe Gly
                 200                 205                 210 tgg cct ctg tat ctg ctg tct tac gtt acc gga cag aag tac ccc aag         966
Trp Pro Leu Tyr Leu Leu Ser Tyr Val Thr Gly Gln Lys Tyr Pro Lys
                 215                 220                 225 ctc aac aaa tgg gct gtc aac cac ttc aac ccc aac gcc ccg ctg ttt         1014
Leu Asn Lys Trp Ala Val Asn His Phe Asn Pro Asn Ala Pro Leu Phe
 230                 235                 240 gag aag aag gac tgg ttc aac atc tgg atc tct aac gtc ggt att ggt         1062
Glu Lys Lys Asp Trp Phe Asn Ile Trp Ile Ser Asn Val Gly Ile Gly
 245                 250                 255                 260 atc acc atg tcc gtc atc gca tac tcc atc aac cga tgg ggc ctg gct         1110
Ile Thr Met Ser Val Ile Ala Tyr Ser Ile Asn Arg Trp Gly Leu Ala
                 265                 270                 275
```

```
tcc gtc acc ctc tac tac ctg atc ccc tac ctg tgg gtc aac cac tgg      1158
Ser Val Thr Leu Tyr Tyr Leu Ile Pro Tyr Leu Trp Val Asn His Trp
            280                 285                 290 ctc gtg gcc atc acc tac ctg cag cac acc gac ccc act ctg ccc cac      1206
Leu Val Ala Ile Thr Tyr Leu Gln His Thr Asp Pro Thr Leu Pro His
    295                 300                 305 tac cac gcc gac cag tgg aac ttc acc cga gga gcc gcc acc atc          1254
Tyr His Ala Asp Gln Trp Asn Phe Thr Arg Gly Ala Ala Ala Thr Ile
310                 315                 320 gac cga gag ttt ggc ttc atc ggc tcc ttc tgc ttc cat gac atc atc      1302
Asp Arg Glu Phe Gly Phe Ile Gly Ser Phe Cys Phe His Asp Ile Ile
325                 330                 335                 340 gag acc cac gtt ctg cac cac tac gtg tct cga att ccc ttc tac aac      1350
Glu Thr His Val Leu His His Tyr Val Ser Arg Ile Pro Phe Tyr Asn
            345                 350                 355 gcc cga atc gcc act gag aag atc aag aag gtc atg ggc aag cac tac      1398
Ala Arg Ile Ala Thr Glu Lys Ile Lys Lys Val Met Gly Lys His Tyr
        360                 365                 370 cga cac gac gac acc aac ttc atc aag tct ctt tac act gtc gcc cga      1446
Arg His Asp Asp Thr Asn Phe Ile Lys Ser Leu Tyr Thr Val Ala Arg
    375                 380                 385 acc tgc cag ttt gtt gaa ggt aag gaa ggc att cag atg ttt aga aac      1494
Thr Cys Gln Phe Val Glu Gly Lys Glu Gly Ile Gln Met Phe Arg Asn
390                 395                 400 gtc aat gga gtc gga gtt gct cct gac ggc ctg cct tct aaa aag          1539
Val Asn Gly Val Gly Val Ala Pro Asp Gly Leu Pro Ser Lys Lys
405                 410                 415 tagagctaga aatgttattt gattgtgttt taactgaaca gcaccgagcc cgaggctaag    1599
ccaagcgaag ccgaggggtt gtgtagtcca tggacgtaac gagtaggcga tcaccgca     1659 ctcggcactg cgtgtctgcg ttcatgggcg aagtcacatt acgctgacaa ccgttgtagt   1719 ttcccttag tatcaatact gttacaagta ccggtctcgt actcgtactg atacgaatct    1779
gtgggaagaa gtcacccta tcagaccttc atactgatgt ttcggatatc aatagaactg   1839
gcatagagcc gttaaagaag tttcacttaa tcactccaac cctcctactt gtagattcaa   1899
gcagatcgat aagatggatt tgatggtcag tgctagc                            1936

<210> SEQ ID NO 24
<211> LENGTH: 419
<212> TYPE: PRT
<213> ORGANISM: Yarrowia lipolytica

<400> SEQUENCE: 24

Met Asp Ser Thr Thr Gln Thr Asn Thr Gly Thr Gly Lys Val Ala Val
1               5                   10                  15

Gln Pro Pro Thr Ala Phe Ile Lys Pro Ile Glu Lys Val Ser Glu Pro
            20                  25                  30

Val Tyr Asp Thr Phe Gly Asn Glu Phe Thr Pro Pro Asp Tyr Ser Ile
        35                  40                  45

Lys Asp Ile Leu Asp Ala Ile Pro Gln Glu Cys Tyr Lys Arg Ser Tyr
    50                  55                  60

Val Lys Ser Tyr Ser Tyr Val Ala Arg Asp Cys Phe Phe Ile Ala Val
65                  70                  75                  80

Phe Ala Tyr Met Ala Tyr Ala Tyr Leu Pro Leu Ile Pro Ser Ala Ser
                85                  90                  95

Gly Arg Ala Val Ala Trp Ala Met Tyr Ser Ile Val Gln Gly Leu Phe
            100                 105                 110
```

-continued

```
Gly Thr Gly Leu Trp Val Leu Ala His Glu Cys Gly His Ser Ala Phe
        115                 120                 125

Ser Asp Ser Asn Thr Val Asn Asn Val Thr Gly Trp Val Leu His Ser
130                 135                 140

Ser Met Leu Val Pro Tyr Tyr Ala Trp Lys Leu Thr His Ser Met His
145                 150                 155                 160

His Lys Ser Thr Gly His Leu Thr Arg Asp Met Val Phe Val Pro Lys
                165                 170                 175

Asp Arg Lys Glu Phe Met Glu Asn Arg Gly Ala His Asp Trp Ser Glu
            180                 185                 190

Leu Ala Glu Asp Ala Pro Leu Met Thr Leu Tyr Gly Leu Ile Thr Gln
        195                 200                 205

Gln Val Phe Gly Trp Pro Leu Tyr Leu Leu Ser Tyr Val Thr Gly Gln
    210                 215                 220

Lys Tyr Pro Lys Leu Asn Lys Trp Ala Val Asn His Phe Asn Pro Asn
225                 230                 235                 240

Ala Pro Leu Phe Glu Lys Lys Asp Trp Phe Asn Ile Trp Ile Ser Asn
                245                 250                 255

Val Gly Ile Gly Ile Thr Met Ser Val Ile Ala Tyr Ser Ile Asn Arg
            260                 265                 270

Trp Gly Leu Ala Ser Val Thr Leu Tyr Tyr Leu Ile Pro Tyr Leu Trp
        275                 280                 285

Val Asn His Trp Leu Val Ala Ile Thr Tyr Leu Gln His Thr Asp Pro
    290                 295                 300

Thr Leu Pro His Tyr His Ala Asp Gln Trp Asn Phe Thr Arg Gly Ala
305                 310                 315                 320

Ala Ala Thr Ile Asp Arg Glu Phe Gly Phe Ile Gly Ser Phe Cys Phe
                325                 330                 335

His Asp Ile Ile Glu Thr His Val Leu His His Tyr Val Ser Arg Ile
            340                 345                 350

Pro Phe Tyr Asn Ala Arg Ile Ala Thr Glu Lys Ile Lys Lys Val Met
        355                 360                 365

Gly Lys His Tyr Arg His Asp Asp Thr Asn Phe Ile Lys Ser Leu Tyr
    370                 375                 380

Thr Val Ala Arg Thr Cys Gln Phe Val Glu Gly Lys Glu Gly Ile Gln
385                 390                 395                 400

Met Phe Arg Asn Val Asn Gly Val Gly Val Ala Pro Asp Gly Leu Pro
                405                 410                 415

Ser Lys Lys

<210> SEQ ID NO 25
<211> LENGTH: 29
<212> TYPE: DNA
<213> ORGANISM: Artificial Sequence
<220> FEATURE:
<223> OTHER INFORMATION: Primer P99

<400> SEQUENCE: 25
ggcaagctta acgccccgct gtttgagaa                                 29

<210> SEQ ID NO 26
<211> LENGTH: 36
<212> TYPE: DNA
<213> ORGANISM: Artificial Sequence
<220> FEATURE:
<223> OTHER INFORMATION: Primer P100
```

```
<400> SEQUENCE: 26
tgacgttgtt agatctacgt gggtctcgat gatgtc                              36

<210> SEQ ID NO 27
<211> LENGTH: 35
<212> TYPE: DNA
<213> ORGANISM: Artificial Sequence
<220> FEATURE:
<223> OTHER INFORMATION: Primer P101

<400> SEQUENCE: 27
gacccacgta gatctaacaa cgtcaccgga tgggt                               35

<210> SEQ ID NO 28
<211> LENGTH: 29
<212> TYPE: DNA
<213> ORGANISM: Artificial Sequence
<220> FEATURE:
<223> OTHER INFORMATION: Primer P102

<400> SEQUENCE: 28
cgggaattcg gggttgaagt ggttgacag                                      29

<210> SEQ ID NO 29
<211> LENGTH: 16
<212> TYPE: DNA
<213> ORGANISM: Artificial Sequence
<220> FEATURE:
<223> OTHER INFORMATION: Primer P119

<400> SEQUENCE: 29
taataacgcc agggtt                                                    16

<210> SEQ ID NO 30
<211> LENGTH: 22
<212> TYPE: DNA
<213> ORGANISM: Artificial Sequence
<220> FEATURE:
<223> OTHER INFORMATION: Primer P120

<400> SEQUENCE: 30
gtagaagggc attcgagaca cg                                             22

<210> SEQ ID NO 31
<211> LENGTH: 22
<212> TYPE: DNA
<213> ORGANISM: Artificial Sequence
<220> FEATURE:
<223> OTHER INFORMATION: Primer P121

<400> SEQUENCE: 31
tgtgcccaag gaccgaaagg ag                                             22

<210> SEQ ID NO 32
<211> LENGTH: 28
<212> TYPE: DNA
<213> ORGANISM: Artificial Sequence
<220> FEATURE:
<223> OTHER INFORMATION: Primer P122

<400> SEQUENCE: 32
tgcaggtagg tgatggccac gagttggg                                       28

<210> SEQ ID NO 33
<211> LENGTH: 25
```

```
<212> TYPE: DNA
<213> ORGANISM: Artificial Sequence
<220> FEATURE:
<223> OTHER INFORMATION: Primer P147

<400> SEQUENCE: 33
tcatgccatg gattcgacca cgcag                                           25

<210> SEQ ID NO 34
<211> LENGTH: 26
<212> TYPE: DNA
<213> ORGANISM: Artificial Sequence
<220> FEATURE:
<223> OTHER INFORMATION: Primer P148

<400> SEQUENCE: 34
acatgcggcc gcctactttt tagaag                                          26

<210> SEQ ID NO 35
<211> LENGTH: 1077
<212> TYPE: DNA
<213> ORGANISM: Saprolegnia diclina

<400> SEQUENCE: 35
atgactgagg ataagacgaa ggtcgagttc ccgacgctca cggagctcaa gcactcgatc     60
ccgaacgcgt gctttgagtc gaacctcggc ctctcgctct actacacggc ccgcgcgatc    120
ttcaacgcgt cggcctcggc ggcgctgctc tacgcggcgc gctcgacgcc gttcattgcc    180
gataacgttc tgctccacgc gctcgtttgc gccacctaca tctacgtgca gggcgtcatc    240
ttctggggct tcttcacggt cggccacgac tgcggccact cggccttctc gcgctaccac    300
agcgtcaact ttatcatcgg ctgcatcatg cactctgcga ttttgacgcc gttcgagagc    360
tggcgcgtga cgcaccgcca ccaccacaag aacacgggca acattgataa ggacgagatc    420
ttttacccgc accggtcggt caaggacctc caggacgtgc gccaatgggt ctacacgctc    480
ggcggtgcgt ggtttgtcta cttgaaggtc gggtatgccc cgcgcacgat gagccacttt    540
gacccgtggg acccgctcct ccttcgccgc gcgtcggccg tcatcgtgtc gctcggcgtc    600
tgggccgcct tcttcgccgc gtacgcgtac ctcacatact cgctcggctt tgccgtcatg    660
ggcctctact actatgcgcc gctctttgtc tttgcttcgt tcctcgtcat tacgaccttc    720
ttgcaccaca acgacgaagc gacgccgtgg tacggcgact cggagtggac gtacgtcaag    780
ggcaacctct cgagcgtcga ccgctcgtac ggcgcgttcg tggacaacct gagccaccac    840
attggcacgc accaggtcca ccacttgttc ccgatcattc cgcactacaa gctcaacgaa    900
gccaccaagc actttgcggc gcgtacccg cacctcgtgc gcaggaacga cgagcccatc    960
atcacggcct tcttcaagac cgcgcacctc tttgtcaact acggcgctgt gcccgagacg   1020
gcgcagatct tcacgctcaa agagtcggcc gcggccgcca aggccaagtc ggactaa      1077

<210> SEQ ID NO 36
<211> LENGTH: 1374
<212> TYPE: DNA
<213> ORGANISM: Mortierella alpina AF465281

<400> SEQUENCE: 36
atggctgctg ctcccagtgt gaggacgttt actcgggccg aggttttgaa tgccgaggct     60
ctgaatgagg gcaagaagga tgccgaggca cccttcttga tgatcatcga caacaaggtg    120
tacgatgtcc gcgagttcgt ccctgatcat cccggtggaa gtgtgattct cacgcacgtt    180
```

```
ggcaaggacg gcactgacgt ctttgacact tttcacccg  aggctgcttg ggagactctt   240
gccaactttt acgttggtga tattgacgag agcgaccgcg atatcaagaa tgatgacttt   300
gcggccgagg tccgcaagct gcgtaccttg ttccagtctc ttggttacta cgattcttcc   360
aaggcatact acgccttcaa ggtctcgttc aacctctgca tctggggttt gtcgacggtc   420
attgtggcca agtggggcca gacctcgacc ctcgccaacg tgctctcggc tgcgcttttg   480
ggtctgttct ggcagcagtg cggatggttg gctcacgact ttttgcatca ccaggtcttc   540
caggaccgtt tctggggtga tcttttcggc gccttcttgg gaggtgtctg ccagggcttc   600
tcgtcctcgt ggtggaagga caagcacaac actcaccacg ccgccccaa  cgtccacggc   660 gaggatcccg acattgacac ccaccctctg ttgacctgga gtgagcatgc gttggagatg   720
ttctcggatg tcccagatga ggagctgacc cgcatgtggt cgcgtttcat ggtcctgaac   780
cagacctggt tttacttccc cattctctcg tttgcccgtc tctcctggtg cctccagtcc   840
attctctttg tgctgcctaa cggtcaggcc cacaagccct cgggcgcgcg tgtgcccatc   900
tcgttggtcg agcagctgtc gcttgcgatg cactggacct ggtacctcgc caccatgttc   960
ctgttcatca aggatcccgt caacatgctg gtgtactttt tggtgtcgca ggcggtgtgc   1020
ggaaacttgt tggcgatcgt gttctcgctc aaccacaacg gtatgcctgt gatctcgaag   1080
gaggaggcgg tcgatatgga tttcttcacg aagcagatca tcacgggtcg tgatgtccac   1140
ccgggtctat ttgccaactg gttcacgggt ggattgaact atcagatcga gcaccacttg   1200
ttcccttcga tgcctcgcca caacttttca agatccagc  ctgctgtcga ccctgtgc    1260 aaaaagtaca atgtccgata ccacaccacc ggtatgatcg agggaactgc agaggtcttt   1320
agccgtctga acgaggtctc caaggctacc tccaagatgg gtaaggcgca gtaa         1374
```

```
<210> SEQ ID NO 37
<211> LENGTH: 457
<212> TYPE: PRT
<213> ORGANISM: Mortierella alpina AF465281

<400> SEQUENCE: 37

Met Ala Ala Pro Ser Val Arg Thr Phe Thr Arg Ala Glu Val Leu
1               5                   10                  15

Asn Ala Glu Ala Leu Asn Glu Gly Lys Lys Asp Ala Glu Ala Pro Phe
            20                  25                  30

Leu Met Ile Ile Asp Asn Lys Val Tyr Asp Val Arg Glu Phe Val Pro
        35                  40                  45

Asp His Pro Gly Gly Ser Val Ile Leu Thr His Val Gly Lys Asp Gly
    50                  55                  60

Thr Asp Val Phe Asp Thr Phe His Pro Glu Ala Ala Trp Glu Thr Leu
65                  70                  75                  80

Ala Asn Phe Tyr Val Gly Asp Ile Asp Glu Ser Asp Arg Asp Ile Lys
                85                  90                  95

Asn Asp Asp Phe Ala Ala Glu Val Arg Lys Leu Arg Thr Leu Phe Gln
            100                 105                 110

Ser Leu Gly Tyr Tyr Asp Ser Ser Lys Ala Tyr Ala Phe Lys Val
        115                 120                 125

Ser Phe Asn Leu Cys Ile Trp Gly Leu Ser Thr Val Ile Val Ala Lys
    130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
```

```
              165                 170                 175
His Gln Val Phe Gln Asp Arg Phe Trp Gly Asp Leu Phe Gly Ala Phe
            180                 185                 190

Leu Gly Gly Val Cys Gln Gly Phe Ser Ser Trp Trp Lys Asp Lys
            195                 200             205

His Asn Thr His His Ala Ala Pro Asn Val His Gly Glu Asp Pro Asp
            210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
        290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Thr Ser Lys Met Gly Lys Ala Gln
    450                 455

<210> SEQ ID NO 38
<211> LENGTH: 1341
<212> TYPE: DNA
<213> ORGANISM: Mortierella alpina AF067654

<400> SEQUENCE: 38
atgggaacgg accaaggaaa aaccttcacc tgggaagagc tggcggccca taacaccaag      60
gacgacctac tcttggccat ccgcggcagg gtgtacgatg tcacaaagtt cttgagccgc     120
catcctggtg gagtggacac tctcctgctc ggagctggcc gagatgttac tccggtcttt     180
gagatgtatc acgcgtttgg ggctgcagat gccattatga agaagtacta tgtcggtaca     240
ctggtctcga atgagctgcc catcttcccg gagccaacgg tgttccacaa aaccatcaag     300
acgagagtcg agggctactt tacggatcgg aacattgatc ccaagaatag accagagatc     360
tggggacgat acgctcttat ctttggatcc ttgatcgctt cctactacgc gcagctcttt     420
gtgcctttcg ttgtcgaacg cacatggctt caggtggtgt ttgcaatcat catgggattt     480
```

```
gcgtgcgcac aagtcggact caaccctctt catgatgcgt ctcactttc agtgacccac      540
aaccccactg tctggaagat tctgggagcc acgcacgact ttttcaacgg agcatcgtac      600
ctggtgtgga tgtaccaaca tatgctcggc catcacccct acaccaacat tgctggagca      660
gatcccgacg tgtcgacgtc tgagcccgat gttcgtcgta tcaagcccaa ccaaaagtgg      720
tttgtcaacc acatcaacca gcacatgttt gttcctttcc tgtacggact gctggcgttc      780
aaggtgcgca ttcaggacat caacattttg tactttgtca agaccaatga cgctattcgt      840
gtcaatccca tctcgacatg gcacactgtg atgttctggg gcggcaaggc tttcttgtc      900
tggtatcgcc tgattgttcc cctgcagtat ctgcccctgg gcaaggtgct gctcttgttc      960
acggtcgcgg acatggtgtc gtcttactgg ctggcgctga ccttccaggc gaaccacgtt     1020
gttgaggaag ttcagtggcc gttgcctgac gagaacggga tcatccaaaa ggactgggca     1080
gctatgcagg tcgagactac gcaggattac gcacacgatt cgcacctctg accagcatc      1140
actggcagct tgaactacca ggctgtgcac catctgttcc ccaacgtgtc gcagcaccat     1200
tatcccgata ttctggccat catcaagaac acctgcagcg agtacaaggt tccataccttt     1260
gtcaaggata cgttttggca agcatttgct tcacatttgg agcacttgcg tgttcttgga     1320
ctccgtccca aggaagagta g                                              1341
```

<210> SEQ ID NO 39
<211> LENGTH: 446
<212> TYPE: PRT
<213> ORGANISM: Mortierella alpina AF067654

<400> SEQUENCE: 39

```
Met Gly Thr Asp Gln Gly Lys Thr Phe Thr Trp Glu Glu Leu Ala Ala
1               5                   10                  15

His Asn Thr Lys Asp Asp Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
            180                 185                 190

Asp Phe Phe Asn Gly Ala Ser Tyr Leu Val Trp Met Tyr Gln His Met
        195                 200                 205

Leu Gly His His Pro Tyr Thr Asn Ile Ala Gly Ala Asp Pro Asp Val
```

```
              210                 215                 220
Ser Thr Ser Glu Pro Asp Val Arg Arg Ile Lys Pro Asn Gln Lys Trp
225                 230                 235                 240

Phe Val Asn His Ile Asn Gln His Met Phe Val Pro Phe Leu Tyr Gly
                245                 250                 255

Leu Leu Ala Phe Lys Val Arg Ile Gln Asp Ile Asn Ile Leu Tyr Phe
                260                 265                 270

Val Lys Thr Asn Asp Ala Ile Arg Val Asn Pro Ile Ser Thr Trp His
            275                 280                 285

Thr Val Met Phe Trp Gly Gly Lys Ala Phe Val Trp Tyr Arg Leu
        290                 295                 300

Ile Val Pro Leu Gln Tyr Leu Pro Leu Gly Lys Val Leu Leu Phe
305                 310                 315                 320

Thr Val Ala Asp Met Val Ser Ser Tyr Trp Leu Ala Leu Thr Phe Gln
                325                 330                 335

Ala Asn His Val Val Glu Glu Val Gln Trp Pro Leu Pro Asp Glu Asn
                340                 345                 350

Gly Ile Ile Gln Lys Asp Trp Ala Ala Met Gln Val Glu Thr Thr Gln
            355                 360                 365

Asp Tyr Ala His Asp Ser His Leu Trp Thr Ser Ile Thr Gly Ser Leu
        370                 375                 380

Asn Tyr Gln Ala Val His His Leu Phe Pro Asn Val Ser Gln His His
385                 390                 395                 400

Tyr Pro Asp Ile Leu Ala Ile Ile Lys Asn Thr Cys Ser Glu Tyr Lys
                405                 410                 415

Val Pro Tyr Leu Val Lys Asp Thr Phe Trp Gln Ala Phe Ala Ser His
                420                 425                 430

Leu Glu His Leu Arg Val Leu Gly Leu Arg Pro Lys Glu Glu
            435                 440                 445

<210> SEQ ID NO 40
<211> LENGTH: 30
<212> TYPE: DNA
<213> ORGANISM: Artificial Sequence
<220> FEATURE:
<223> OTHER INFORMATION: Primer YL11

<400> SEQUENCE: 40
ttttccatgg gaacggacca aggaaaaacc                                    30

<210> SEQ ID NO 41
<211> LENGTH: 30
<212> TYPE: DNA
<213> ORGANISM: Artificial Sequence
<220> FEATURE:
<223> OTHER INFORMATION: Primer YL12

<400> SEQUENCE: 41
tttgcggccg cctactcttc cttgggacgg                                    30

<210> SEQ ID NO 42
<211> LENGTH: 33
<212> TYPE: DNA
<213> ORGANISM: Artificial Sequence
<220> FEATURE:
<223> OTHER INFORMATION: Primer YL21A

<400> SEQUENCE: 42
tttccatggc tgaggataag acgaaggtcg agt                                33
```

<210> SEQ ID NO 43
<211> LENGTH: 36
<212> TYPE: DNA
<213> ORGANISM: Artificial Sequence
<220> FEATURE:
<223> OTHER INFORMATION: Primer YL22

<400> SEQUENCE: 43

```
cccttaatta attagtccga cttggccttg gcggcc                                    36
```

<210> SEQ ID NO 44
<211> LENGTH: 957
<212> TYPE: DNA
<213> ORGANISM: Mortierella alpina AX464731

<400> SEQUENCE: 44

```
atggagtcga ttgcgccatt cctcccatca aagatgccgc aagatctgtt tatggacctt         60
gccaccgcta tcggtgtccg ggccgcgccc tatgtcgatc tctcgaggc cgcgctggtg         120
gcccaggccg agaagtacat ccccacgatt gtccatcaca cgcgtgggtt cctggtcgcg         180
gtggagtcgc ctttggcccg tgagctgccg ttgatgaacc cgttccacgt gctgttgatc         240
gtgctcgctt atttggtcac ggtctttgtg ggcatgcaga tcatgaagaa ctttgagcgg         300
ttcgaggtca agacgttttc gctcctgcac aacttttgtc tggtctcgat cagcgcctac         360
atgtgcggtg ggatcctgta cgaggcttat caggccaact atggactgtt gagaacgct          420
gctgatcata ccttcaaggg tcttcctatg ccaagatga tctggctctt ctacttctcc          480
aagatcatgg agtttgtcga caccatgatc atggtcctca agaagaacaa ccgccagatc         540
tccttcttgc acgtttacca ccacagctcc atcttcacca tctggtggtt ggtcaccttt         600
gttgcaccca acgtgaagc ctacttctct gctgcgttga actcgttcat ccatgtgatc          660
atgtacggct actacttctt gtcggccttg ggcttcaagc aggtgtcgtt catcaagttc         720
tacatcacgc gctcgcagat gacacagttc tgcatgatgt cggtccagtc ttcctgggac         780
atgtacgcca tgaaggtcct tggccgcccc ggatacccct tcttcatcac ggctctgctt         840
tggttctaca tgtggaccat gctcggtctc ttctacaact tttacagaaa gaacgccaag         900
ttggccaagc aggccaaggc cgacgctgcc aaggagaagg caaggaagtt gcagtaa           957
```

<210> SEQ ID NO 45
<211> LENGTH: 318
<212> TYPE: PRT
<213> ORGANISM: Mortierella alpina AX464731

<400> SEQUENCE: 45

```
Met Glu Ser Ile Ala Pro Phe Leu Pro Ser Lys Met Pro Gln Asp Leu
1               5                  10                  15

Phe Met Asp Leu Ala Thr Ala Ile Gly Val Arg Ala Ala Pro Tyr Val
            20                  25                  30

Asp Pro Leu Glu Ala Ala Leu Val Ala Gln Ala Glu Lys Tyr Ile Pro
        35                  40                  45

Thr Ile Val His His Thr Arg Gly Phe Leu Val Ala Val Glu Ser Pro
    50                  55                  60

Leu Ala Arg Glu Leu Pro Leu Met Asn Pro Phe His Val Leu Leu Ile
65                  70                  75                  80

Val Leu Ala Tyr Leu Val Thr Val Phe Val Gly Met Gln Ile Met Lys
                85                  90                  95
```

```
Asn Phe Glu Arg Phe Glu Val Lys Thr Phe Ser Leu Leu His Asn Phe
                100                 105                 110
Cys Leu Val Ser Ile Ser Ala Tyr Met Cys Gly Gly Ile Leu Tyr Glu
            115                 120                 125
Ala Tyr Gln Ala Asn Tyr Gly Leu Phe Glu Asn Ala Ala Asp His Thr
        130                 135                 140
Phe Lys Gly Leu Pro Met Ala Lys Met Ile Trp Leu Phe Tyr Phe Ser
145                 150                 155                 160
Lys Ile Met Glu Phe Val Asp Thr Met Ile Met Val Leu Lys Lys Asn
                165                 170                 175
Asn Arg Gln Ile Ser Phe Leu His Val Tyr His His Ser Ser Ile Phe
            180                 185                 190
Thr Ile Trp Trp Leu Val Thr Phe Val Ala Pro Asn Gly Glu Ala Tyr
        195                 200                 205
Phe Ser Ala Ala Leu Asn Ser Phe Ile His Val Ile Met Tyr Gly Tyr
    210                 215                 220
Tyr Phe Leu Ser Ala Leu Gly Phe Lys Gln Val Ser Phe Ile Lys Phe
225                 230                 235                 240
Tyr Ile Thr Arg Ser Gln Met Thr Gln Phe Cys Met Met Ser Val Gln
                245                 250                 255
Ser Ser Trp Asp Met Tyr Ala Met Lys Val Leu Gly Arg Pro Gly Tyr
            260                 265                 270
Pro Phe Phe Ile Thr Ala Leu Leu Trp Phe Tyr Met Trp Thr Met Leu
        275                 280                 285
Gly Leu Phe Tyr Asn Phe Tyr Arg Lys Asn Ala Lys Leu Ala Lys Gln
    290                 295                 300
Ala Lys Ala Asp Ala Ala Lys Glu Lys Ala Arg Lys Leu Gln
305                 310                 315

<210> SEQ ID NO 46
<211> LENGTH: 1077
<212> TYPE: DNA
<213> ORGANISM: Saprolegnia declina

<400> SEQUENCE: 46
atggctgagg ataagaccaa ggtcgagttc cctaccctga ctgagctgaa gcactctatc      60
cctaacgctt gctttgagtc caacctcgga ctctcgctct actacactgc ccgagcgatc     120
ttcaacgcat ctgcctctgc tgctctgctc tacgctgccc gatctactcc cttcattgcc     180
gataacgttc tgctccacgc tctggttgc gccacctaca tctacgtgca gggtgtcatc      240
ttctggggtt tctttaccgt cggtcacgac tgtggtcact ctgccttctc ccgataccac     300
tccgtcaact tcatcattgg ctgcatcatg cactctgcca ttctgactcc cttcgagtcc     360
tggcgagtga cccaccgaca ccatcacaag aacactggca acattgataa ggacgagatc     420
ttctaccctc atcggtccgt caaggaccct caggacgtgc acaatgggt ctacaccctc      480
ggaggtgctt ggtttgtcta cctgaaggtc ggatatgctc ctcgaaccat gtcccacttt     540
gaccctggg acctctcct gcttcgacga gcctccgctg tcatcgtgtc cctcggagtc       600
tgggctgcct cttcgctgc ctacgcctac ctcacatact cgctcggctt tgccgtcatg      660
ggcctctact actatgctcc tctctttgtc tttgcttcgt tcctcgtcat tactaccttc     720
ttgcatcaca cgacgaagc tactccctgg tacggtgact cggagtggac ctacgtcaag     780
ggcaacctga gctccgtcga ccgatcgtac ggagctttcg tggacaacct gtctcaccac     840
attggcaccc accaggtcca tcacttgttc cctatcattc cccactacaa gctcaacgaa     900
```

```
gccaccaagc actttgctgc cgcttaccct cacctcgtga gacgtaacga cgagcccatc    960
attactgcct tcttcaagac cgctcacctc tttgtcaact acggagctgt gcccgagact   1020
gctcagattt tcaccctcaa agagtctgcc gctgcagcca aggccaagag cgactaa      1077
```

<210> SEQ ID NO 47
<211> LENGTH: 358
<212> TYPE: PRT
<213> ORGANISM: Saprolegnia declina

<400> SEQUENCE: 47

```
Met Ala Glu Asp Lys Thr Lys Val Glu Phe Pro Thr Leu Thr Glu Leu
1               5                   10                  15

Lys His Ser Ile Pro Asn Ala Cys Phe Glu Ser Asn Leu Gly Leu Ser
            20                  25                  30

Leu Tyr Tyr Thr Ala Arg Ala Ile Phe Asn Ala Ser Ala Ser Ala Ala
        35                  40                  45

Leu Leu Tyr Ala Ala Arg Ser Thr Pro Phe Ile Ala Asp Asn Val Leu
    50                  55                  60

Leu His Ala Leu Val Cys Ala Thr Tyr Ile Tyr Val Gln Gly Val Ile
65                  70                  75                  80

Phe Trp Gly Phe Phe Thr Val Gly His Asp Cys Gly His Ser Ala Phe
                85                  90                  95

Ser Arg Tyr His Ser Val Asn Phe Ile Ile Gly Cys Ile Met His Ser
            100                 105                 110

Ala Ile Leu Thr Pro Phe Glu Ser Trp Arg Val Thr His Arg His His
        115                 120                 125

His Lys Asn Thr Gly Asn Ile Asp Lys Asp Glu Ile Phe Tyr Pro His
    130                 135                 140

Arg Ser Val Lys Asp Leu Gln Asp Val Arg Gln Trp Val Tyr Thr Leu
145                 150                 155                 160

Gly Gly Ala Trp Phe Val Tyr Leu Lys Val Gly Tyr Ala Pro Arg Thr
                165                 170                 175

Met Ser His Phe Asp Pro Trp Asp Pro Leu Leu Leu Arg Arg Ala Ser
            180                 185                 190

Ala Val Ile Val Ser Leu Gly Val Trp Ala Ala Phe Phe Ala Ala Tyr
        195                 200                 205

Ala Tyr Leu Thr Tyr Ser Leu Gly Phe Ala Val Met Gly Leu Tyr Tyr
    210                 215                 220

Tyr Ala Pro Leu Phe Val Phe Ala Ser Phe Leu Val Ile Thr Thr Phe
225                 230                 235                 240

Leu His His Asn Asp Glu Ala Thr Pro Trp Tyr Gly Asp Ser Glu Trp
                245                 250                 255

Thr Tyr Val Lys Gly Asn Leu Ser Ser Val Asp Arg Ser Tyr Gly Ala
            260                 265                 270

Phe Val Asp Asn Leu Ser His His Ile Gly Thr His Gln Val His His
        275                 280                 285

Leu Phe Pro Ile Ile Pro His Tyr Lys Leu Asn Glu Ala Thr Lys His
    290                 295                 300

Phe Ala Ala Ala Tyr Pro His Leu Val Arg Arg Asn Asp Glu Pro Ile
305                 310                 315                 320

Ile Thr Ala Phe Phe Lys Thr Ala His Leu Phe Val Asn Tyr Gly Ala
                325                 330                 335

Val Pro Glu Thr Ala Gln Ile Phe Thr Leu Lys Glu Ser Ala Ala Ala
```

Ala Lys Ala Lys Ser Asp
        355

<210> SEQ ID NO 48
<211> LENGTH: 105
<212> TYPE: DNA
<213> ORGANISM: Artificial Sequence
<220> FEATURE:
<223> OTHER INFORMATION: Primer D17-1A

<400> SEQUENCE: 48
catggctgag gataagacca aggtcgagtt ccctaccctg actgagctga agcactctat    60
ccctaacgct tgctttgagt ccaacctcgg actctcgctc tacta                  105

<210> SEQ ID NO 49
<211> LENGTH: 106
<212> TYPE: DNA
<213> ORGANISM: Artificial Sequence
<220> FEATURE:
<223> OTHER INFORMATION: Primer D17-1B

<400> SEQUENCE: 49
cagtgtagta gagcgagagt ccgaggttgg actcaaagca agcgttaggg atagagtgct    60
tcagctcagt cagggtaggg aactcgacct tggtcttatc ctcagc                 106

<210> SEQ ID NO 50
<211> LENGTH: 106
<212> TYPE: DNA
<213> ORGANISM: Artificial Sequence
<220> FEATURE:
<223> OTHER INFORMATION: Primer D17-2A

<400> SEQUENCE: 50
cactgcccga gcgatcttca acgcatctgc ctctgctgct ctgctctacg ctgcccgatc    60
tactcccttc attgccgata acgttctgct ccacgctctg gtttgc                 106

<210> SEQ ID NO 51
<211> LENGTH: 106
<212> TYPE: DNA
<213> ORGANISM: Artificial Sequence
<220> FEATURE:
<223> OTHER INFORMATION: Primer D17-2B

<400> SEQUENCE: 51
gtggcgcaaa ccagagcgtg gagcagaacg ttatcggcaa tgaagggagt agatcgggca    60
gcgtagagca gagcagcaga ggcagatgcg ttgaagatcg ctcggg                 106

<210> SEQ ID NO 52
<211> LENGTH: 105
<212> TYPE: DNA
<213> ORGANISM: Artificial Sequence
<220> FEATURE:
<223> OTHER INFORMATION: Primer D17-3A

<400> SEQUENCE: 52
gccacctaca tctacgtgca gggtgtcatc ttctggggtt tctttaccgt cggtcacgac    60
tgtggtcact ctgcctttctc ccgataccac tccgtcaact tcatc                 105

<210> SEQ ID NO 53
<211> LENGTH: 105
<212> TYPE: DNA

<213> ORGANISM: Artificial Sequence
<220> FEATURE:
<223> OTHER INFORMATION: Primer D17-3B

<400> SEQUENCE: 53
ccaatgatga agttgacgga gtggtatcgg gagaaggcag agtgaccaca gtcgtgaccg    60
acggtaaaga aaccccagaa gatgacaccc tgcacgtaga tgtag                  105

<210> SEQ ID NO 54
<211> LENGTH: 105
<212> TYPE: DNA
<213> ORGANISM: Artificial Sequence
<220> FEATURE:
<223> OTHER INFORMATION: Primer D17-4A

<400> SEQUENCE: 54
attggctgca tcatgcactc tgccattctg actcccttcg agtcctggcg agtgacccac    60
cgacaccatc acaagaacac tggcaacatt gataaggacg agatc                  105

<210> SEQ ID NO 55
<211> LENGTH: 105
<212> TYPE: DNA
<213> ORGANISM: Artificial Sequence
<220> FEATURE:
<223> OTHER INFORMATION: Primer D17-4B

<400> SEQUENCE: 55
tagaagatct cgtccttatc aatgttgcca gtgttcttgt gatggtgtcg gtgggtcact    60
cgccaggact cgaagggagt cagaatggca gagtgcatga tgcag                  105

<210> SEQ ID NO 56
<211> LENGTH: 105
<212> TYPE: DNA
<213> ORGANISM: Artificial Sequence
<220> FEATURE:
<223> OTHER INFORMATION: Primer D17-5A

<400> SEQUENCE: 56
acgagatctt ctaccctcat cggtccgtca aggacctcca ggacgtgcga caatgggtct    60
acaccctcgg aggtgcttgg tttgtctacc tgaaggtcgg atatg                  105

<210> SEQ ID NO 57
<211> LENGTH: 107
<212> TYPE: DNA
<213> ORGANISM: Artificial Sequence
<220> FEATURE:
<223> OTHER INFORMATION: Primer D17-5B

<400> SEQUENCE: 57
aggagcatat ccgaccttca ggtagacaaa ccaagcacct ccgagggtgt agacccattg    60
tcgcacgtcc tggaggtcct tgacggaccg atgagggtag aagatct                107

<210> SEQ ID NO 58
<211> LENGTH: 105
<212> TYPE: DNA
<213> ORGANISM: Artificial Sequence
<220> FEATURE:
<223> OTHER INFORMATION: Primer D17-6A

<400> SEQUENCE: 58
ctcctcgaac catgtcccac tttgacccct gggaccctct cctgcttcga cgagcctccg    60
ctgtcatcgt gtccctcgga gtctgggctg ccttcttcgc tgcct                  105

<210> SEQ ID NO 59
<211> LENGTH: 106
<212> TYPE: DNA
<213> ORGANISM: Artificial Sequence
<220> FEATURE:
<223> OTHER INFORMATION: Primer D17-6B

<400> SEQUENCE: 59
aggcgtaggc agcgaagaag gcagcccaga ctccgaggga cacgatgaca gcggaggctc    60
gtcgaagcag gagagggtcc caggggtcaa agtgggacat ggttcg                  106

<210> SEQ ID NO 60
<211> LENGTH: 104
<212> TYPE: DNA
<213> ORGANISM: Artificial Sequence
<220> FEATURE:
<223> OTHER INFORMATION: Primer D17-7A

<400> SEQUENCE: 60
acgcctacct cacatactcg ctcggctttg ccgtcatggg cctctactac tatgctcctc    60
tctttgtctt tgcttcgttc ctcgtcatta ctaccttctt gcat                    104

<210> SEQ ID NO 61
<211> LENGTH: 103
<212> TYPE: DNA
<213> ORGANISM: Artificial Sequence
<220> FEATURE:
<223> OTHER INFORMATION: Primer D17-7B

<400> SEQUENCE: 61
ttgtgatgca agaaggtagt aatgacgagg aacgaagcaa agacaaagag aggagcatag    60
tagtagaggc ccatgacggc aaagccgagc gagtatgtga ggt                     103

<210> SEQ ID NO 62
<211> LENGTH: 106
<212> TYPE: DNA
<213> ORGANISM: Artificial Sequence
<220> FEATURE:
<223> OTHER INFORMATION: Primer D17-8A

<400> SEQUENCE: 62
cacaacgacg aagctactcc ctggtacggt gactcggagt ggacctacgt caagggcaac    60
ctgagctccg tcgaccgatc gtacggagct ttcgtggaca acctgt                  106

<210> SEQ ID NO 63
<211> LENGTH: 106
<212> TYPE: DNA
<213> ORGANISM: Artificial Sequence
<220> FEATURE:
<223> OTHER INFORMATION: Primer D17-8B

<400> SEQUENCE: 63
gtgagacagg ttgtccacga aagctccgta cgatcggtcg acggagctca ggttgccctt    60
gacgtaggtc cactccgagt caccgtacca gggagtagct tcgtcg                  106

<210> SEQ ID NO 64
<211> LENGTH: 102
<212> TYPE: DNA
<213> ORGANISM: Artificial Sequence
<220> FEATURE:
<223> OTHER INFORMATION: Primer D17-9A

<400> SEQUENCE: 64
ctcaccacat tggcacccac caggtccatc acttgttccc tatcattccc cactacaagc    60
tcaacgaagc caccaagcac tttgctgccg cttaccctca cc    102

<210> SEQ ID NO 65
<211> LENGTH: 102
<212> TYPE: DNA
<213> ORGANISM: Artificial Sequence
<220> FEATURE:
<223> OTHER INFORMATION: Primer D17-9B

<400> SEQUENCE: 65
cacgaggtga gggtaagcgg cagcaaagtg cttggtggct tcgttgagct tgtagtgggg    60
aatgataggg aacaagtgat ggacctggtg ggtgccaatg tg    102

<210> SEQ ID NO 66
<211> LENGTH: 76
<212> TYPE: DNA
<213> ORGANISM: Artificial Sequence
<220> FEATURE:
<223> OTHER INFORMATION: Primer D17-10A

<400> SEQUENCE: 66
tcgtgagacg taacgacgag cccatcatta ctgccttctt caagaccgct cacctctttg    60
tcaactacgg agctgt    76

<210> SEQ ID NO 67
<211> LENGTH: 76
<212> TYPE: DNA
<213> ORGANISM: Artificial Sequence
<220> FEATURE:
<223> OTHER INFORMATION: Primer D17-10B

<400> SEQUENCE: 67
cgggcacagc tccgtagttg acaaagaggt gagcggtctt gaagaaggca gtaatgatgg    60
gctcgtcgtt acgtct    76

<210> SEQ ID NO 68
<211> LENGTH: 67
<212> TYPE: DNA
<213> ORGANISM: Artificial Sequence
<220> FEATURE:
<223> OTHER INFORMATION: Primer D17-11A

<400> SEQUENCE: 68
gcccgagact gctcagattt tcaccctcaa agagtctgcc gctgcagcca aggccaagag    60
cgactaa    67

<210> SEQ ID NO 69
<211> LENGTH: 62
<212> TYPE: DNA
<213> ORGANISM: Artificial Sequence
<220> FEATURE:
<223> OTHER INFORMATION: Primer D17-11B

<400> SEQUENCE: 69
ttagtcgctc ttggccttgg ctgcagcggc agactctttg agggtgaaaa tctgagcagt    60
ct    62

<210> SEQ ID NO 70
<211> LENGTH: 32

```
<212> TYPE: DNA
<213> ORGANISM: Artificial Sequence
<220> FEATURE:
<223> OTHER INFORMATION: Primer D17-1

<400> SEQUENCE: 70
tttccatggc tgaggataag accaaggtcg ag                                    32

<210> SEQ ID NO 71
<211> LENGTH: 34
<212> TYPE: DNA
<213> ORGANISM: Artificial Sequence
<220> FEATURE:
<223> OTHER INFORMATION: Primer D17-4R

<400> SEQUENCE: 71
ccctagaaga tctcgtcctt atcaatgttg ccag                                  34

<210> SEQ ID NO 72
<211> LENGTH: 27
<212> TYPE: DNA
<213> ORGANISM: Artificial Sequence
<220> FEATURE:
<223> OTHER INFORMATION: Primer D17-5

<400> SEQUENCE: 72
cccacgagat cttctaccct catcggt                                          27

<210> SEQ ID NO 73
<211> LENGTH: 24
<212> TYPE: DNA
<213> ORGANISM: Artificial Sequence
<220> FEATURE:
<223> OTHER INFORMATION: Primer D17-8D

<400> SEQUENCE: 73
gaaagctccg tacgatcggt cgac                                             24

<210> SEQ ID NO 74
<211> LENGTH: 24
<212> TYPE: DNA
<213> ORGANISM: Artificial Sequence
<220> FEATURE:
<223> OTHER INFORMATION: Primer D17-8U

<400> SEQUENCE: 74
gtcgaccgat cgtacggagc tttc                                             24

<210> SEQ ID NO 75
<211> LENGTH: 34
<212> TYPE: DNA
<213> ORGANISM: Artificial Sequence
<220> FEATURE:
<223> OTHER INFORMATION: Primer D17-11

<400> SEQUENCE: 75
aaagcggccg cttagtcgct cttggccttg gctg                                  34

<210> SEQ ID NO 76
<211> LENGTH: 36
<212> TYPE: DNA
<213> ORGANISM: Artificial Sequence
<220> FEATURE:
<223> OTHER INFORMATION: Primer YL53

<400> SEQUENCE: 76
```

```
gccaagtcgg actaagctgc taactagagc ggccgc                                  36

<210> SEQ ID NO 77
<211> LENGTH: 36
<212> TYPE: DNA
<213> ORGANISM: Artificial Sequence
<220> FEATURE:
<223> OTHER INFORMATION: Primer YL54

<400> SEQUENCE: 77
gcggccgctc tagttagcag cttagtccga cttggc                                  36

<210> SEQ ID NO 78
<211> LENGTH: 35
<212> TYPE: DNA
<213> ORGANISM: Artificial Sequence
<220> FEATURE:
<223> OTHER INFORMATION: Primer KU5

<400> SEQUENCE: 78
tttgcccggg cgagtatctg tctgactcgt cattg                                   35

<210> SEQ ID NO 79
<211> LENGTH: 33
<212> TYPE: DNA
<213> ORGANISM: Artificial Sequence
<220> FEATURE:
<223> OTHER INFORMATION: Primer KU3

<400> SEQUENCE: 79
aaagcccggg caaaggcctg tttctcggtg tac                                     33

<210> SEQ ID NO 80
<211> LENGTH: 1710
<212> TYPE: DNA
<213> ORGANISM: Yarrowia lipolytica

<400> SEQUENCE: 80
gtcgacgagt atctgtctga ctcgtcattg ccgcctttgg agtacgactc caactatgag        60
tgtgcttgga tcactttgac gatacattct tcgttggagg ctgtgggtct gacagctgcg       120
ttttcggcgc ggttggccga caacaatatc agctgcaacg tcattgctgg ctttcatcat       180
gatcacattt ttgtcggcaa aggcgacgcc cagagagcca ttgacgttct ttctaatttg       240
gaccgatagc cgtatagtcc agtctatcta aagttcaac taactcgtaa ctattaccat        300
aacatatact tcactgcccc agataaggtt ccgataaaaa gttctgcaga ctaaatttat       360
ttcagtctcc tcttcaccac caaaatgccc tcctacgaag ctcgagctaa cgtccacaag       420
tccgcctttg ccgctcgagt gctcaagctc gtggcagcca agaaaaccaa cctgtgtgct       480
tctctggatg ttaccaccac caaggagctc attgagcttg ccgataaggt cggaccttat       540
gtgtgcatga tcaagaccca tatcgacatc attgacgact tcacctacgc cggcactgtg       600
ctcccccctca aggaacttgc tcttaagcac ggtttcttcc tgttcgagga cagaaagttc       660
gcagatattg caacactgt caagcaccag tacaagaacg tgtctaccg aatcgccgag         720
tggtccgata tcaccaacgc ccacggtgta cccggaaccg gaatcattgc tggcctgcga       780
gctggtgccg aggaaactgt ctctgaacag aagaaggagg acgtctctga ctacgagaac       840
tcccagtaca aggagttcct ggtcccctct cccaacgaga gctggccag aggtctgctc        900
atgctggccg agctgtcttg caagggctct ctggccactg gcgagtactc caagcagacc       960
attgagcttg cccgatccga ccccgagttt gtggttggct tcattgccca gaaccgacct      1020
```

```
aagggcgact ctgaggactg gcttattctg accccegggg tgggtcttga cgacaaggga   1080
gacgctctcg gacagcagta ccgaactgtt gaggatgtca tgtctaccgg aacggatatc   1140
ataattgtcg gccgaggtct gtacggccag aaccgagatc ctattgagga ggccaagcga   1200
taccagaagg ctggctggga ggcttaccag aagattaact gttagaggtt agactatgga   1260
tatgtcattt aactgtgtat atagagagcg tgcaagtatg gagcgcttgt tcagcttgta   1320
tgatggtcag acgacctgtc tgatcgagta tgtatgatac tgcacaacct gtgtatccgc   1380
atgatctgtc caatgggca tgttgttgtg tttctcgata cggagatgct gggtacaagt   1440
agctaatacg attgaactac ttatacttat atgaggcttg aagaaagctg acttgtgtat   1500
gacttattct caactacatc cccagtcaca ataccaccac tgcactacca ctacaccaaa   1560
accatgatca aaccacccat ggacttcctg gaggcagaag aacttgttat ggaaaagctc   1620
aagagagaga agccaagata ctatcaagac atgtgtcgca acttcaagga ggaccaagct   1680
ctgtacaccg agaaacaggc ctttgtcgac                                    1710
```

<210> SEQ ID NO 81
<211> LENGTH: 286
<212> TYPE: PRT
<213> ORGANISM: Yarrowia lipolytica

<400> SEQUENCE: 81

```
Met Pro Ser Tyr Glu Ala Arg Ala Asn Val His Lys Ser Ala Phe Ala
1               5                   10                  15

Ala Arg Val Leu Lys Leu Val Ala Ala Lys Lys Thr Asn Leu Cys Ala
            20                  25                  30

Ser Leu Asp Val Thr Thr Thr Lys Glu Leu Ile Glu Leu Ala Asp Lys
        35                  40                  45

Val Gly Pro Tyr Val Cys Met Ile Lys Thr His Ile Asp Ile Ile Asp
    50                  55                  60

Asp Phe Thr Tyr Ala Gly Thr Val Leu Pro Leu Lys Glu Leu Ala Leu
65                  70                  75                  80

Lys His Gly Phe Phe Leu Phe Glu Asp Arg Lys Phe Ala Asp Ile Gly
                85                  90                  95

Asn Thr Val Lys His Gln Tyr Lys Asn Gly Val Tyr Arg Ile Ala Glu
            100                 105                 110

Trp Ser Asp Ile Thr Asn Ala His Gly Val Pro Gly Thr Gly Ile Ile
        115                 120                 125

Ala Gly Leu Arg Ala Gly Ala Glu Glu Thr Val Ser Glu Gln Lys Lys
    130                 135                 140

Glu Asp Val Ser Asp Tyr Glu Asn Ser Gln Tyr Lys Glu Phe Leu Val
145                 150                 155                 160

Pro Ser Pro Asn Glu Lys Leu Ala Arg Gly Leu Leu Met Leu Ala Glu
                165                 170                 175

Leu Ser Cys Lys Gly Ser Leu Ala Thr Gly Glu Tyr Ser Lys Gln Thr
            180                 185                 190

Ile Glu Leu Ala Arg Ser Asp Pro Glu Phe Val Gly Phe Ile Ala
        195                 200                 205

Gln Asn Arg Pro Lys Gly Asp Ser Glu Asp Trp Leu Ile Leu Thr Pro
    210                 215                 220

Gly Val Gly Leu Asp Asp Lys Gly Asp Ala Leu Gly Gln Gln Tyr Arg
225                 230                 235                 240

Thr Val Glu Asp Val Met Ser Thr Gly Thr Asp Ile Ile Ile Val Gly
```

```
                  245                 250                 255
Arg Gly Leu Tyr Gly Gln Asn Arg Asp Pro Ile Glu Glu Ala Lys Arg
            260                 265                 270
Tyr Gln Lys Ala Gly Trp Glu Ala Tyr Gln Lys Ile Asn Cys
        275                 280                 285

<210> SEQ ID NO 82
<211> LENGTH: 35
<212> TYPE: DNA
<213> ORGANISM: Artificial Sequence
<220> FEATURE:
<223> OTHER INFORMATION: Primer KI5

<400> SEQUENCE: 82
agagcggccg catgggagaa gtgggaccca caaac                              35

<210> SEQ ID NO 83
<211> LENGTH: 38
<212> TYPE: DNA
<213> ORGANISM: Artificial Sequence
<220> FEATURE:
<223> OTHER INFORMATION: Primer KI3

<400> SEQUENCE: 83
gtggcggccg ctcaaatgtc gttattgtac caataaac                           38

<210> SEQ ID NO 84
<211> LENGTH: 1152
<212> TYPE: DNA
<213> ORGANISM: Impatients balsama

<400> SEQUENCE: 84
atgggagaag tgggacccac aaaccgaacc aaaaccaagt tggacaagca acaagaatcc   60
gaaaacaggg ttcctcacga gccacctcca ttcacactaa gtgacttaa gaaagccatc   120 ccacccatt gcttcgagcg ctccctcgtg aaatcattct accacgtgat tcacgacatt   180
atcatcctgt cctttttcta ctatgtcgcc gccaattaca tccccatgct acccaaaac   240 ctccgttacg ttgcatggcc aatttattgg gccatccaag gctgtgtcca acttggtata   300
ttggtcttag ccatgaatg cggccaccac gccttcagcg actaccaatg ggtagacgac   360
atggtcgggt tcgtcctcca ctcgtcccaa ttgattccct acttctcatg gaaacatagc   420
caccgtcgcc accactccaa cacggcctcc atcgagcgcg acgaggtcta cccgcccgcg   480
tacaaaaacg acctgccgtg gttcgccaaa tacctacgca accccgtcgg tcgtttcctc   540
atgattttcg gggcgctact gttcggctgg ccgtcgtacc ttctgttcaa cgcgaacggc   600
cgtctctacg accgcttcgc ttcccactac gacccgcaat cccgatcttt caacaaccgc   660
gagaggctgc aagtgatcgc gtccgacgtc gggctcgtct tcgcgtactt tgtcctgtac   720
aagatcgcgc tggccaaggg atttgtgtgg ttaatttgtg tgtatggcgt cccgtacgtg   780
atcctcaacg ggcttatcgt cttgatcacg ttcctacagc acacgcaccc gaatctgccc   840
cgttacgacc tttccgagtg ggactggctt agggagccc tgtcgactgt ggaccgcgat   900
tacgggatgt tgaataaggt gttccataac gtgacggaca cgcacttggt gcatcatttg   960
ttcacgacca tgccacatta tcgcgccaag gaggcgaccg aggtgattaa accgatattg   1020
ggagactact ataagtttga cgacactccg tttctcaaag cgttgtggaa ggacatggga   1080
aagtgtattt atgtggagtc ggacgtgcct ggcaagaaca agggagttta ttggtacaat   1140
aacgacattt ga                                                      1152
```

<210> SEQ ID NO 85
<211> LENGTH: 383
<212> TYPE: PRT
<213> ORGANISM: Impatients balsama

<400> SEQUENCE: 85

```
Met Gly Glu Val Gly Pro Thr Asn Arg Thr Lys Thr Lys Leu Asp Lys
1               5                   10                  15

Gln Gln Glu Ser Glu Asn Arg Val Pro His Glu Pro Pro Phe Thr
            20                  25                  30

Leu Ser Asp Leu Lys Lys Ala Ile Pro Pro His Cys Phe Glu Arg Ser
            35                  40                  45

Leu Val Lys Ser Phe Tyr His Val Ile His Asp Ile Ile Leu Ser
    50                  55                  60

Phe Phe Tyr Tyr Val Ala Ala Asn Tyr Ile Pro Met Leu Pro Gln Asn
65                  70                  75                  80

Leu Arg Tyr Val Ala Trp Pro Ile Tyr Trp Ala Ile Gln Gly Cys Val
                85                  90                  95

Gln Leu Gly Ile Leu Val Leu Gly His Glu Cys Gly His His Ala Phe
            100                 105                 110

Ser Asp Tyr Gln Trp Val Asp Asp Met Val Gly Phe Val Leu His Ser
            115                 120                 125

Ser Gln Leu Ile Pro Tyr Phe Ser Trp Lys His Ser His Arg Arg His
    130                 135                 140

His Ser Asn Thr Ala Ser Ile Glu Arg Asp Glu Val Tyr Pro Pro Ala
145                 150                 155                 160

Tyr Lys Asn Asp Leu Pro Trp Phe Ala Lys Tyr Leu Arg Asn Pro Val
                165                 170                 175

Gly Arg Phe Leu Met Ile Phe Gly Ala Leu Leu Phe Gly Trp Pro Ser
            180                 185                 190

Tyr Leu Leu Phe Asn Ala Asn Gly Arg Leu Tyr Asp Arg Phe Ala Ser
    195                 200                 205

His Tyr Asp Pro Gln Ser Pro Ile Phe Asn Asn Arg Glu Arg Leu Gln
    210                 215                 220

Val Ile Ala Ser Asp Val Gly Leu Val Phe Ala Tyr Phe Val Leu Tyr
225                 230                 235                 240

Lys Ile Ala Leu Ala Lys Gly Phe Val Trp Leu Ile Cys Val Tyr Gly
                245                 250                 255

Val Pro Tyr Val Ile Leu Asn Gly Leu Ile Val Leu Ile Thr Phe Leu
            260                 265                 270

Gln His Thr His Pro Asn Leu Pro Arg Tyr Asp Leu Ser Glu Trp Asp
    275                 280                 285

Trp Leu Arg Gly Ala Leu Ser Thr Val Asp Arg Asp Tyr Gly Met Leu
    290                 295                 300

Asn Lys Val Phe His Asn Val Thr Asp Thr His Val His His Leu
305                 310                 315                 320

Phe Thr Thr Met Pro His Tyr Arg Ala Lys Glu Ala Thr Glu Val Ile
                325                 330                 335

Lys Pro Ile Leu Gly Asp Tyr Tyr Lys Phe Asp Asp Thr Pro Phe Leu
            340                 345                 350

Lys Ala Leu Trp Lys Asp Met Gly Lys Cys Ile Tyr Val Glu Ser Asp
    355                 360                 365

Val Pro Gly Lys Asn Lys Gly Val Tyr Trp Tyr Asn Asn Asp Ile
```

<210> SEQ ID NO 86
<211> LENGTH: 34
<212> TYPE: DNA
<213> ORGANISM: Artificial Sequence
<220> FEATURE:
<223> OTHER INFORMATION: Primer KTI5

<400> SEQUENCE: 86
aagctcgaga ccgggttggc ggcgtatttg tgtc                         34

<210> SEQ ID NO 87
<211> LENGTH: 38
<212> TYPE: DNA
<213> ORGANISM: Artificial Sequence
<220> FEATURE:
<223> OTHER INFORMATION: Primer KTI3

<400> SEQUENCE: 87
ggtctcgaga tctccaccgc ggacacaata tctggtca                     38

<210> SEQ ID NO 88
<211> LENGTH: 1756
<212> TYPE: DNA
<213> ORGANISM: Artificial Sequence
<220> FEATURE:
<223> OTHER INFORMATION: TEF/conjugase/XPR chimeric gene

<400> SEQUENCE: 88

| | |
|---|---|
| gaccgggttg gcggcgtatt tgtgtcccaa aaaacagccc caattgcccc aattgacccc | 60 |
| aaattgaccc agtagcgggc ccaaccccgg cgagagcccc cttcacccca catatcaaac | 120 |
| ctcccccggt tcccacactt gccgttaagg gcgtagggta ctgcagtctg gaatctacgc | 180 |
| ttgttcagac tttgtactag tttctttgtc tggccatccg ggtaacccat gccggacgca | 240 |
| aaatagacta ctgaaaattt ttttgctttg tggttgggac tttagccaag ggtataaaag | 300 |
| accaccgtcc ccgaattacc tttcctcttc ttttctctct ctccttgtca actcacaccc | 360 |
| gaaatcgtta agcatttcct tctgagtata agaatcattc aaaggatcca ctagttctag | 420 |
| agcggccgca tggagaagt gggacccaca aaccgaacca aaaccaagtt ggacaagcaa | 480 |
| caagaatccg aaaacagggt tcctcacgag ccacctccat tcacactaag tgaccttaag | 540 |
| aaagccatcc cacccattg cttcgagcgc tccctcgtga atcattcta ccacgtgatt | 600 |
| cacgacatta tcatcctgtc cttttcctac tatgtcgccg ccaattacat ccccatgcta | 660 |
| ccccaaaacc tccgttacgt tgcatggcca atttattggg ccatccaagg ctgtgtccaa | 720 |
| cttggtatat tggtcttagg ccatgaatgc ggccaccacg ccttcagcga ctaccaatgg | 780 |
| gtagacgaca tggtcgggtt cgtcctccac tcgtcccaat tgattcccta cttctcatgg | 840 |
| aaacatagcc accgtcgcca ccactccaac acggcctcca tcgagcgcga cgaggtctac | 900 |
| ccgcccgcgt acaaaaacga cctgccgtgg ttcgccaaat acctacgcaa ccccgtcggt | 960 |
| cgtttcctca tgattttcgg ggcgctactg ttcggctggc cgtcgtacct tctgttcaac | 1020 |
| gcgaacggcc gtctctacga ccgcttcgct tcccactacg acccgcaatc cccgatcttc | 1080 |
| aacaaccgcg agaggctgca agtgatcgcg tccgacgtcg ggctcgtctt cgcgtacttt | 1140 |
| gtcctgtaca agatcgcgct ggccaaggga tttgtgtggt taatttgtgt gtatgcgtc | 1200 |
| ccgtacgtga tcctcaacgg gcttatcgtc ttgatcacgt tcctacagca cacgcacccg | 1260 |
| aatctgcccc gttacgacct ttccgagtgg gactggctta ggggagccct gtcgactgtg | 1320 |

```
gaccgcgatt acgggatgtt gaataaggtg ttccataacg tgacggacac gcacttggtg    1380
catcatttgt tcacgaccat gccacattat cgcgccaagg aggcgaccga ggtgattaaa    1440
ccgatattgg gagactacta taagtttgac gacactccgt ttctcaaagc gttgtggaag    1500
gacatgggaa agtgtattta tgtggagtcg gacgtgcctg gcaagaacaa gggagtttat    1560
tggtacaata acgacatttg agcggccgcc accgcggccc gagattccgg cctcttcggc    1620
cgccaagcga cccgggtgga cgtctagagg tacctagcaa ttaacagata gtttgccggt    1680
gataattctc ttaacctccc acactccttt gacataacga tttatgtaac gaaactgaaa    1740
tttgaccaga tattgt                                                    1756
```

<210> SEQ ID NO 89
<211> LENGTH: 383
<212> TYPE: PRT
<213> ORGANISM: Artificial Sequence
<220> FEATURE:
<223> OTHER INFORMATION: TEF/conjugase/XPR chimeric protein

<400> SEQUENCE: 89

```
Met Gly Glu Val Gly Pro Thr Asn Arg Thr Lys Thr Lys Leu Asp Lys
1               5                   10                  15

Gln Gln Glu Ser Glu Asn Arg Val Pro His Glu Pro Pro Phe Thr
            20                  25                  30

Leu Ser Asp Leu Lys Lys Ala Ile Pro Pro His Cys Phe Glu Arg Ser
        35                  40                  45

Leu Val Lys Ser Phe Tyr His Val Ile His Asp Ile Ile Leu Ser
    50                  55                  60

Phe Phe Tyr Tyr Val Ala Ala Asn Tyr Ile Pro Met Leu Pro Gln Asn
65                  70                  75                  80

Leu Arg Tyr Val Ala Trp Pro Ile Tyr Trp Ala Ile Gln Gly Cys Val
                85                  90                  95

Gln Leu Gly Ile Leu Val Leu Gly His Glu Cys Gly His His Ala Phe
            100                 105                 110

Ser Asp Tyr Gln Trp Val Asp Asp Met Val Gly Phe Val Leu His Ser
        115                 120                 125

Ser Gln Leu Ile Pro Tyr Phe Ser Trp Lys His Ser His Arg Arg His
    130                 135                 140

His Ser Asn Thr Ala Ser Ile Glu Arg Asp Glu Val Tyr Pro Pro Ala
145                 150                 155                 160

Tyr Lys Asn Asp Leu Pro Trp Phe Ala Lys Tyr Leu Arg Asn Pro Val
                165                 170                 175

Gly Arg Phe Leu Met Ile Phe Gly Ala Leu Leu Phe Gly Trp Pro Ser
            180                 185                 190

Tyr Leu Leu Phe Asn Ala Asn Gly Arg Leu Tyr Asp Arg Phe Ala Ser
        195                 200                 205

His Tyr Asp Pro Gln Ser Pro Ile Phe Asn Asn Arg Glu Arg Leu Gln
    210                 215                 220

Val Ile Ala Ser Asp Val Gly Leu Val Phe Ala Tyr Phe Val Leu Tyr
225                 230                 235                 240

Lys Ile Ala Leu Ala Lys Gly Phe Val Trp Leu Ile Cys Val Tyr Gly
                245                 250                 255

Val Pro Tyr Val Ile Leu Asn Gly Leu Ile Val Leu Ile Thr Phe Leu
            260                 265                 270

Gln His Thr His Pro Asn Leu Pro Arg Tyr Asp Leu Ser Glu Trp Asp
```

```
                275                 280                 285
Trp Leu Arg Gly Ala Leu Ser Thr Val Asp Arg Asp Tyr Gly Met Leu
    290                 295                 300

Asn Lys Val Phe His Asn Val Thr Asp Thr His Leu Val His His Leu
305                 310                 315                 320

Phe Thr Thr Met Pro His Tyr Arg Ala Lys Glu Ala Thr Glu Val Ile
                325                 330                 335

Lys Pro Ile Leu Gly Asp Tyr Tyr Lys Phe Asp Thr Pro Phe Leu
                340                 345                 350

Lys Ala Leu Trp Lys Asp Met Gly Lys Cys Ile Tyr Val Glu Ser Asp
                355                 360                 365

Val Pro Gly Lys Asn Lys Gly Val Tyr Trp Tyr Asn Asn Asp Ile
    370                 375                 380

<210> SEQ ID NO 90
<211> LENGTH: 32
<212> TYPE: DNA
<213> ORGANISM: Artificial Sequence
<220> FEATURE:
<223> OTHER INFORMATION: Primer KH5

<400> SEQUENCE: 90
tagagcggcc gcttaaacca tgaaaaagcc tg                              32

<210> SEQ ID NO 91
<211> LENGTH: 33
<212> TYPE: DNA
<213> ORGANISM: Artificial Sequence
<220> FEATURE:
<223> OTHER INFORMATION: Primer KH3

<400> SEQUENCE: 91
gtggcggccg ctttaggtac ctcactattc ctt                             33

<210> SEQ ID NO 92
<211> LENGTH: 1026
<212> TYPE: DNA
<213> ORGANISM: Escherichia coli

<400> SEQUENCE: 92
atgaaaaagc tgaactcac cgcgacgtct gtcgagaagt ttctgatcga aaagttcgac   60
agcgtctccg acctgatgca gctctcggag ggcgaagaat ctcgtgcttt cagcttcgat  120
gtaggagggc gtggatatgt cctgcgggta aatagctgcg ccgatggttt ctacaaagat  180
cgttatgttt atcggcactt tgcatcggcc gcgctcccga ttccggaagt gcttgacatt  240
ggggaattca gcgagagcct gacctattgc atctcccgcc gtgcacaggg tgtcacgttg  300
caagacctgc tgaaaccgga actgcccgct gttctgcagc cggtcgcgga ggccatggat  360
gcgatcgctg cggccgatct tagccagacg agcgggttcg gcccattcgg accgcaagga  420
atcggtcaat acactacatg gcgtgatttc atatgcgcga ttgctgatcc ccatgtgtat  480
cactggcaaa ctgtgatgga cgacaccgtc agtgcgtccg tcgcgcaggc tctcgatgag  540
ctgatgcttt gggccgagga ctgccccgaa gtccggcacc tcgtgcacgc ggatttcggc  600
tccaacaatg tcctgacgga caatggccgc ataacagcgg tcattgactg agcgaggcg  660 atgttcgggg attcccaata cgaggtcgcc aacatcttct tctggaggcc gtggttggct  720
tgtatggagc agcagacgcg ctacttcgag cggaggcatc cggagcttgc aggatcgccg  780
cggctccggg cgtatatgct ccgcattggt cttgaccaac tctatcagag cttggttgac  840
```

```
ggcaatttcg atgatgcagc ttgggcgcag ggtcgatgcg acgcaatcgt ccgatccgga    900
gccgggactg tcgggcgtac acaaatcgcc cgcagaagcg cggccgtctg gaccgatggc    960
tgtgtagaag tactcgccga tagtggaaac cgacgcccca gcactcgtcc gagggcaaag   1020
gaatag                                                              1026
```

<210> SEQ ID NO 93
<211> LENGTH: 341
<212> TYPE: PRT
<213> ORGANISM: Escherichia coli

<400> SEQUENCE: 93

```
Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335
```

Pro Arg Ala Lys Glu
        340

<210> SEQ ID NO 94
<211> LENGTH: 34
<212> TYPE: DNA
<213> ORGANISM: Artificial Sequence
<220> FEATURE:
<223> OTHER INFORMATION: Primer KTH5

<400> SEQUENCE: 94
tttagatctc gagaccgggt tggcggcgta tttg                                  34

<210> SEQ ID NO 95
<211> LENGTH: 31
<212> TYPE: DNA
<213> ORGANISM: Artificial Sequence
<220> FEATURE:
<223> OTHER INFORMATION: Primer KTH3

<400> SEQUENCE: 95
tttagatctc caccgcggac acaatatctg g                                     31

<210> SEQ ID NO 96
<211> LENGTH: 1650
<212> TYPE: DNA
<213> ORGANISM: Artificial Sequence
<220> FEATURE:
<223> OTHER INFORMATION: TEF::HPT::XPR fusion

<400> SEQUENCE: 96
gaccgggttg gcggcgtatt tgtgtcccaa aaaacagccc caattgcccc aattgacccc      60
aaattgaccc agtagcgggc ccaaccccgg cgagagcccc cttcacccca catatcaaac     120
ctcccccggt tcccacactt gccgttaagg gcgtagggta ctgcagtctg gaatctacgc     180
ttgttcagac tttgtactag tttctttgtc tggccatccg ggtaacccat gccggacgca     240
aaatagacta ctgaaaattt ttttgctttg tggttgggac tttagccaag ggtataaaag     300
accaccgtcc ccgaattacc tttcctcttc ttttctctct ctccttgtca actcacaccc     360
gaaatcgtta agcatttcct tctgagtata agaatcattc aaaggatcca ctagttctag     420
agcggccgct taaaccatga aaaagcctga actcaccgcg acgtctgtcg agaagtttct     480
gatcgaaaag ttcgacagcg tctccgacct gatgcagctc tcggagggcg aagaatctcg     540
tgctttcagc ttcgatgtag gagggcgtgg atatgtcctg cgggtaaata gctgcgccga     600
tggtttctac aaagatcgtt atgtttatcg gcactttgca tcggccgcgc tcccgattcc     660
ggaagtgctt gacattgggg aattcagcga gagcctgacc tattgcatct cccgccgtgc     720
acagggtgtc acgttgcaag acctgcctga aaccgaactg cccgctgttc tgcagccggt     780
cgcggaggcc atggatgcga tcgctgcggc cgatcttagc cagacgagcg ggttcggccc     840
attcggaccg caaggaatcg gtcaatacac tacatggcgt gatttcatat gcgcgattgc     900
tgatccccat gtgtatcact ggcaaactgt gatggacgac accgtcagtg cgtccgtcgc     960
gcaggctctc gatgagctga tgctttgggc cgaggactgc cccgaagtcc ggcacctcgt    1020
gcacgcggat ttcggctcca acaatgtcct gacggacaat ggccgcataa cagcggtcat    1080
tgactggagc gaggcgatgt tcggggattc ccaatacgag gtcgccaaca tcttcttctg    1140
gaggccgtgg ttggcttgta tggagcagca gacgcgctac ttcgagcgga ggcatccgga    1200
gcttgcagga tcgccgcggc tccgggcgta tatgctccgc attggtcttg accaactcta    1260

```
tcagagcttg gttgacggca atttcgatga tgcagcttgg gcgcagggtc gatgcgacgc    1320
aatcgtccga tccggagccg ggactgtcgg gcgtacacaa atcgcccgca gaagcgcggc    1380
cgtctggacc gatggctgtg tagaagtact cgccgatagt ggaaaccgac gccccagcac    1440
tcgtccgagg gcaaaggaat agtgaggtac ctaaagcggc cgccaccgcg gcccgagatt    1500
ccggcctctt cggccgccaa gcacccgggt tggacgtcta gaggtaccta gcaattaaca    1560
gatagtttgc cggtgataat tctcttaacc tcccacactc ctttgacata acgatttatg    1620
taacgaaact gaaatttgac cagatattgt                                     1650
```

```
<210> SEQ ID NO 97
<211> LENGTH: 341
<212> TYPE: PRT
<213> ORGANISM: Artificial Sequence
<220> FEATURE:
<223> OTHER INFORMATION: TEF::HPT::XPR fusion

<400> SEQUENCE: 97

Met Lys Lys Pro Glu Leu Thr Ala Thr Ser Val Glu Lys Phe Leu Ile
1               5                   10                  15

Glu Lys Phe Asp Ser Val Ser Asp Leu Met Gln Leu Ser Glu Gly Glu
            20                  25                  30

Glu Ser Arg Ala Phe Ser Phe Asp Val Gly Gly Arg Gly Tyr Val Leu
        35                  40                  45

Arg Val Asn Ser Cys Ala Asp Gly Phe Tyr Lys Asp Arg Tyr Val Tyr
    50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255

Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285
```

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Pro Ser Thr Arg
                325                 330                 335

Pro Arg Ala Lys Glu
            340

<210> SEQ ID NO 98
<211> LENGTH: 401
<212> TYPE: DNA
<213> ORGANISM: Yarrowia lipolytica

<400> SEQUENCE: 98
cgagtatctg tctgactcgt cattgccgcc tttggagtac gactccaact atgagtgtgc      60
ttggatcact ttgacgatac attcttcgtt ggaggctgtg ggtctgacag ctgcgttttc     120
ggcgcggttg ccgacaaca atatcagctg caacgtcatt gctggctttc atcatgatca     180
cattttgtc ggcaaaggcg acgcccagag agccattgac gttctttcta atttggaccg     240
atagccgtat agtccagtct atctataagt tcaactaact cgtaactatt accataacat     300
atacttcact gccccagata aggttccgat aaaaagttct gcagactaaa tttatttcag     360
tctcctcttc accaccaaaa tgccctccta cgaagctcga g                        401

<210> SEQ ID NO 99
<211> LENGTH: 568
<212> TYPE: DNA
<213> ORGANISM: Yarrowia lipolytica

<400> SEQUENCE: 99
atcataattg tcggccgagg tctgtacggc cagaaccgag atcctattga ggaggccaag      60
cgataccaga aggctggctg ggaggcttac cagaagatta actgttagag gttagactat     120
ggatatgtca tttaactgtg tatatagaga gcgtgcaagt atggagcgct tgttcagctt     180
gtatgatggt cagacgacct gtctgatcga gtatgtatga tactgcacaa cctgtgtatc     240
cgcatgatct gtccaatggg gcatgttgtt gtgtttctcg atacggagat gctgggtaca     300
agtagctaat acgattgaac tacttatact tatatgaggc ttgaagaaag ctgacttgtg     360
tatgacttat tctcaactac atccccagtc acaataccac cactgcacta ccactacacc     420
aaaaccatga tcaaaccacc catggacttc ctggaggcag aagaacttgt tatggaaaag     480
ctcaagagag agaagccaag atactatcaa gacatgtgtc gcaacttcaa ggaggaccaa     540
gctctgtaca ccgagaaaca ggcctttg                                       568

<210> SEQ ID NO 100
<211> LENGTH: 36
<212> TYPE: DNA
<213> ORGANISM: Artificial Sequence
<220> FEATURE:
<223> OTHER INFORMATION: Primer YL63

<400> SEQUENCE: 100
ttatgatatc gaattaatta acctgcagcc cggggg                               36

<210> SEQ ID NO 101
<211> LENGTH: 36
<212> TYPE: DNA
<213> ORGANISM: Artificial Sequence
<220> FEATURE:
<223> OTHER INFORMATION: Primer YL64

<400> SEQUENCE: 101
cccccgggct gcaggttaat taattcgata tcataa        36

<210> SEQ ID NO 102
<211> LENGTH: 33
<212> TYPE: DNA
<213> ORGANISM: Artificial Sequence
<220> FEATURE:
<223> OTHER INFORMATION: Primer YL65

<400> SEQUENCE: 102
tacgccgcca acccgtacgt ctcgagcttc gta        33

<210> SEQ ID NO 103
<211> LENGTH: 33
<212> TYPE: DNA
<213> ORGANISM: Artificial Sequence
<220> FEATURE:
<223> OTHER INFORMATION: Primer YL66

<400> SEQUENCE: 103
tacgaagctc gagacgtacg ggttggcggc gta        33

<210> SEQ ID NO 104
<211> LENGTH: 33
<212> TYPE: DNA
<213> ORGANISM: Artificial Sequence
<220> FEATURE:
<223> OTHER INFORMATION: Primer YL81

<400> SEQUENCE: 104
gttatccgct cacaagcttc cacacaacgt acg        33

<210> SEQ ID NO 105
<211> LENGTH: 33
<212> TYPE: DNA
<213> ORGANISM: Artificial Sequence
<220> FEATURE:
<223> OTHER INFORMATION: Primer YL82

<400> SEQUENCE: 105
cgtacgttgt gtggaagctt gtgagcggat aac        33

<210> SEQ ID NO 106
<211> LENGTH: 33
<212> TYPE: DNA
<213> ORGANISM: Artificial Sequence
<220> FEATURE:
<223> OTHER INFORMATION: Primer YL83

<400> SEQUENCE: 106
atttgaatcg aatcgatgag cctaaaatga acc        33

<210> SEQ ID NO 107
<211> LENGTH: 33
<212> TYPE: DNA
<213> ORGANISM: Artificial Sequence
<220> FEATURE:
<223> OTHER INFORMATION: Primer YL84

<400> SEQUENCE: 107
ggttcatttt aggctcatcg attcgattca aat        33

```
<210> SEQ ID NO 108
<211> LENGTH: 38
<212> TYPE: DNA
<213> ORGANISM: Artificial Sequence
<220> FEATURE:
<223> OTHER INFORMATION: Primer YL105

<400> SEQUENCE: 108
ccaagcacta acctaccgtt taaacaccac taaaaccc                              38

<210> SEQ ID NO 109
<211> LENGTH: 38
<212> TYPE: DNA
<213> ORGANISM: Artificial Sequence
<220> FEATURE:
<223> OTHER INFORMATION: Primer YL106

<400> SEQUENCE: 109
gggttttagt ggtgtttaaa cggtaggtta gtgcttgg                              38

<210> SEQ ID NO 110
<211> LENGTH: 36
<212> TYPE: DNA
<213> ORGANISM: Artificial Sequence
<220> FEATURE:
<223> OTHER INFORMATION: Primer YL119

<400> SEQUENCE: 110
cgggaaacct gtcgtggcgc gccagctgca ttaatg                                36

<210> SEQ ID NO 111
<211> LENGTH: 36
<212> TYPE: DNA
<213> ORGANISM: Artificial Sequence
<220> FEATURE:
<223> OTHER INFORMATION: Primer YL120

<400> SEQUENCE: 111
cattaatgca gctggcgcgc cacgacaggt ttcccg                                36

<210> SEQ ID NO 112
<211> LENGTH: 34
<212> TYPE: DNA
<213> ORGANISM: Artificial Sequence
<220> FEATURE:
<223> OTHER INFORMATION: Primer YL121

<400> SEQUENCE: 112
tttggcgcgc ctatcacatc acgctctcat caag                                 34

<210> SEQ ID NO 113
<211> LENGTH: 34
<212> TYPE: DNA
<213> ORGANISM: Artificial Sequence
<220> FEATURE:
<223> OTHER INFORMATION: Primer YL122

<400> SEQUENCE: 113
tttcgtacga accaccaccg tcagcccttc tgac                                 34

<210> SEQ ID NO 114
<211> LENGTH: 440
<212> TYPE: DNA
<213> ORGANISM: Yarrowia lipolytica

<400> SEQUENCE: 114
```

```
aaccaccacc gtcagccctt ctgactcacg tattgtagcc accgacacag gcaacagtcc    60
gtggatagca gaatatgtct tgtcggtcca tttctcacca actttaggcg tcaagtgaat   120
gttgcagaag aagtatgtgc cttcattgag aatcggtgtt gctgatttca ataaagtctt   180
gagatcagtt tggccagtca tgttgtgggg ggtaattgga ttgagttatc gcctacagtc   240
tgtacaggta tactcgctgc ccactttata ctttttgatt ccgctgcact tgaagcaatg   300
tcgtttacca aaagtgagaa tgctccacag aacacacccc agggtatggt tgagcaaaaa   360
ataaacactc cgatacgggg aatcgaaccc cggtctccac ggttctcaag aagtattctt   420
gatgagagcg tgatgtgata                                               440
```

<210> SEQ ID NO 115
<211> LENGTH: 35
<212> TYPE: DNA
<213> ORGANISM: Artificial Sequence
<220> FEATURE:
<223> OTHER INFORMATION: Primer YL114

<400> SEQUENCE: 115

```
tgatagtatc ttggcgcgcc ttctctctct tgagc                               35
```

<210> SEQ ID NO 116
<211> LENGTH: 35
<212> TYPE: DNA
<213> ORGANISM: Artificial Sequence
<220> FEATURE:
<223> OTHER INFORMATION: Primer YL115

<400> SEQUENCE: 116

```
gctcaagaga gagaaggcgc gccaagatac tatca                               35
```

<210> SEQ ID NO 117
<211> LENGTH: 5218
<212> TYPE: DNA
<213> ORGANISM: Artificial Sequence
<220> FEATURE:
<223> OTHER INFORMATION: 5218 bp fragment for integration and
      expression of the delta-5 desaturase gene

<400> SEQUENCE: 117

```
tatcacatca cgctctcatc aagaatactt cttgagaacc gtggagaccg gggttcgatt    60
ccccgtatcg gagtgtttat tttttgctca accataccct ggggtgtgtt ctgtggagca   120
ttctcacttt tggtaaacga cattgcttca agtgcagcgg aatcaaaaag tataaagtgg   180
gcagcgagta tacctgtaca gactgtaggc gataactcaa tccaattacc ccccacaaca   240
tgactggcca aactgatctc aagactttat tgaaatcagc aacaccgatt ctcaatgaag   300
gcacatactt cttctgcaac attcacttga cgcctaaagt tggtgagaaa tggaccgaca   360
agacatattc tgctatccac ggactgttgc ctgtgtcggt ggctacaata cgtgagtcag   420
aagggctgac ggtggtggtt cgtacgttgt gtggaagctt gtgagcggat aacaatttca   480
cacaggaaac agctatgacc atgattacgc caagctcgaa attaaccctc actaaaggga   540
acaaaagctg gagctccacc gcggacacaa tatctggtca aatttcagtt cgttacata   600 aatcgttatg tcaaaggagt gtgggaggtt aagagaatta tcaccggcaa actatctgtt   660
aattgctagg tacctctaga cgtccacccg ggtcgcttgg cggccgaaga ggccggaatc   720
tcgggccgcg gtgcggccg cctactcttc cttgggacgg agtccaagaa cacgcaagtg   780
ctccaaatgt gaagcaaatg cttgccaaaa cgtatccttg acaaggtatg gaaccttgta   840
```

```
ctcgctgcag gtgttcttga tgatggccag aatatcggga taatggtgct gcgacacgtt      900
ggggaacaga tggtgcacag ccggtagttc aagctgccag tgatgctggt ccagaggtgc      960
gaatcgtgtg cgtaatcctg cgtagtctcg acctgcatag ctgcccagtc cttttggatg     1020
atcccgttct cgtcaggcaa cggccactga acttcctcaa caacgtggtt cgcctggaag     1080
gtcagcgcca gccagtaaga cgacaccatg tccgcgaccg tgaacaagag cagcaccttg     1140
cccaggggca gatactgcag gggaacaatc aggcgatacc agacaaagaa agccttgccg     1200
ccccagaaca tcacagtgtg ccatgtcgag atgggattga cacgaatagc gtcattggtc     1260
ttgacaaagt acaaaatgtt gatgtcctga atgcgcacct gaacgccag cagtccgtac      1320
aggaaaggaa caaacatgtg ctggttgatg tggttgacaa accacttttg gttgggcttg     1380
atacgacgaa catcgggctc agacgtcgac acgtcgggat ctgctccagc aatgttggtg     1440
tagggtgat ggccgagcat atgttggtac atccacacca ggtacgatgc tccgttgaaa      1500
aagtcgtgcg tggctcccag aatcttccag acagtggggt tgtgggtcac tgaaaagtga     1560
gacgcatcat gaagagggtt gagtccgact tgtgcgcacg caaatcccat gatgattgca     1620
aacaccacct gaagccatgt gcgttcgaca acgaaaggca caaagagctg cgcgtagtag     1680
gaagcgatca aggatccaaa gataagagcg tatcgtcccc agatctctgg tctattcttg     1740
ggatcaatgt tccgatccgt aaagtagccc tcgactctcg tcttgatggt tttgtggaac     1800
accgttggct ccgggaagat gggcagctca ttcgagacca gtgtaccgac atagtacttc     1860
ttcataatgg catctgcagc cccaaacgcg tgatacatct caaagaccgg agtaacatct     1920
cggccagctc cgagcaggag agtgtccact ccaccaggat ggcggctcaa gaactttgtg     1980
acatcgtaca ccctgccgcg gatggccaag agtaggtcgt ccttggtgtt atgggccgcc     2040
agctcttccc aggtgaaggt ttttccttgg tccgttccca tggtgaatga ttcttatact     2100
cagaaggaaa tgcttaacga tttcgggtgt gagttgacaa ggagagagag aaaagaagag     2160
gaaaggtaat tcggggacgg tggtctttta tacccttggc taaagtccca accacaaagc     2220
aaaaaaattt tcagtagtct attttgcgtc cggcatgggt tacccggatg ccagacaaa     2280
gaaactagta caaagtctga acaagcgtag attccagact gcagtaccct acgcccttaa     2340
cggcaagtgt gggaaccggg ggaggtttga tatgtgggt gaaggggct ctcgccgggg       2400
ttgggcccgc tactgggtca atttggggtc aattggggca attggggctg ttttttggga     2460
cacaaatacg ccgccaaccc ggtctctcct gaattctgca gatgggctgc aggaattccg     2520
tcgtcgcctg agtcgacatc atttatttac cagttggcca caaacccttg acgatctcgt     2580
atgtcccctc cgacatactc ccggccggct ggggtacgtt cgatagcgct atcggcatcg     2640
acaaggtttg ggtccctagc cgataccgca ctacctgagt cacaatcttc ggaggtttag     2700
tcttccacat agcacgggca aaagtgcgta tatatacaag agcgtttgcc agccacagat     2760
tttcactcca cacaccacat cacacataca accacacaca tccacaatgg aacccgaaac     2820
taagaagacc aagactgact ccaagaagat tgttcttctc ggcggcgact tctgtggccc     2880
cgaggtgatt gccgaggccg tcaaggtgct caagtctgtt gctgaggcct ccggcaccga     2940
gtttgtgttt gaggaccgac tcattggagg agctgccatt gagaaggagg gcgagcccat     3000
caccgacgct actctcgaca tctgccgaaa ggctgactct attatgctcg gtgctgtcgg     3060
aggcgctgcc aacaccgtat ggaccactcc cgacggacga accgacgtgc gacccgagca     3120
gggtctcctc aagctgcgaa aggacctgaa cctgtacgcc aacctgcgac cctgccagct     3180
```

-continued

```
gctgtcgccc aagctcgccg atctctcccc catccgaaac gttgagggca ccgacttcat    3240
cattgtccga gagctcgtcg gaggtatcta ctttggagag cgaaaggagg atgacggatc    3300
tggcgtcgct tccgacaccg agacctactc cgttcctgag gttgagcgaa ttgcccgaat    3360
ggccgccttc ctggcccttc agcacaaccc ccctcttccc gtgtggtctc ttgacaaggc    3420
caacgtgctg gcctcctctc gactttggcg aaagactgtc actcgagtcc tcaaggacga    3480
attccccag ctcgagctca accaccagct gatcgactcg gccgccatga tcctcatcaa    3540
gcagccctcc aagatgaatg gtatcatcat caccaccaac atgtttggcg atatcatctc    3600
cgacgaggcc tccgtcatcc ccggttctct gggtctgctg ccctccgcct ctctggcttc    3660
tctgcccgac accaacgagg cgttcggtct gtacgagccc tgtcacggat ctgcccccga    3720
tctcggcaag cagaaggtca accccattgc caccattctg tctgccgcca tgatgctcaa    3780
gttctctctt aacatgaagc ccgccggtga cgctgttgag gctgccgtca aggagtccgt    3840
cgaggctggt atcactaccg ccgatatcgg aggctcttcc tccacctccg aggtcggaga    3900
cttgttgcca acaaggtcaa ggagctgctc aagaaggagt aagtcgtttc tacgacgcat    3960
tgatggaagg agcaaactga cgcgcctgcg ggttggtcta ccggcagggt ccgctagtgt    4020
ataagactct ataaaaggg ccctgccctg ctaatgaaat gatgatttat aatttaccgg    4080
tgtagcaacc ttgactagaa gaagcagatt gggtgtgttt gtagtggagg acagtggtac    4140
gttttggaaa cagtcttctt gaaagtgtct tgtctacagt atattcactc ataacctcaa    4200
tagccaaggg tgtagtcggt ttattaaagg aagggagttg tggctgatgt ggatagatat    4260
ctttaagctg gcgactgcac ccaacgagtg tggtggtagc ttgttactgt atattcggta    4320
agatatattt tgtggggttt tagtggtgtt taaacggtag gttagtgctt ggtatatgag    4380
ttgtaggcat gacaatttgg aaaggggtgg actttgggaa tattgtggga tttcaatacc    4440
ttagtttgta cagggtaatt gttacaaatg atacaaagaa ctgtatttct tttcatttgt    4500
tttaattggt tgtatatcaa gtccgttaga cgagctcagt gccttggctt ttggcactgt    4560
atttcatttt tagaggtaca ctacattcag tgaggtatgg taaggttgag ggcataatga    4620
aggcaccttg tactgacagt cacagacctc tcaccgagaa ttttatgaga tatactcggg    4680
ttcattttag gctcatcgat tcgattcaaa ttaattaatt cgatatcata attgtcggcc    4740
gaggtctgta cggccagaac cgagatccta ttgaggaggc caagcgatac cagaaggctg    4800
gctgggaggc ttaccagaag attaactgtt agaggttaga ctatggatat gtcatttaac    4860
tgtgtatata gagagcgtgc aagtatggag cgcttgttca gcttgtatga tggtcagacg    4920
acctgtctga tcgagtatgt atgatactgc acaacctgtg tatccgcatg atctgtccaa    4980
tggggcatgt tgttgtgttt ctcgatacgg agatgctggg tacaagtagc taatacgatt    5040
gaactactta tacttatatg aggcttgaag aaagctgact tgtgtatgac ttattctcaa    5100
ctacatcccc agtcacaata ccaccactgc actaccacta caccaaaacc atgatcaaac    5160
cacccatgga cttcctggag gcagaagaac ttgttatgga aaagctcaag agagagaa     5218
```

<210> SEQ ID NO 118
<211> LENGTH: 33
<212> TYPE: DNA
<213> ORGANISM: Artificial Sequence
<220> FEATURE:
<223> OTHER INFORMATION: Primer YL69

<400> SEQUENCE: 118
agcccatctg cagaagcttc aggagagacc ggg                                   33

<210> SEQ ID NO 119
<211> LENGTH: 33
<212> TYPE: DNA
<213> ORGANISM: Artificial Sequence
<220> FEATURE:
<223> OTHER INFORMATION: Primer YL70

<400> SEQUENCE: 119
cccggtctct cctgaagctt ctgcagatgg gct                33

<210> SEQ ID NO 120
<211> LENGTH: 33
<212> TYPE: DNA
<213> ORGANISM: Artificial Sequence
<220> FEATURE:
<223> OTHER INFORMATION: Primer YL77

<400> SEQUENCE: 120
tagtgagggt taattaatcg agcttggcgt aat                33

<210> SEQ ID NO 121
<211> LENGTH: 33
<212> TYPE: DNA
<213> ORGANISM: Artificial Sequence
<220> FEATURE:
<223> OTHER INFORMATION: Primer YL78

<400> SEQUENCE: 121
attacgccaa gctcgattaa ttaaccctca cta                33

<210> SEQ ID NO 122
<211> LENGTH: 34
<212> TYPE: DNA
<213> ORGANISM: Artificial Sequence
<220> FEATURE:
<223> OTHER INFORMATION: Primer YL79A

<400> SEQUENCE: 122
attcctgcag cccatcgatg cagaattcag gaga                34

<210> SEQ ID NO 123
<211> LENGTH: 34
<212> TYPE: DNA
<213> ORGANISM: Artificial Sequence
<220> FEATURE:
<223> OTHER INFORMATION: Primer YL80A

<400> SEQUENCE: 123
tctcctgaat tctgcatcga tgggctgcag gaat                34

<210> SEQ ID NO 124
<211> LENGTH: 8894
<212> TYPE: DNA
<213> ORGANISM: Artificial Sequence
<220> FEATURE:
<223> OTHER INFORMATION: 8894 bp fragment for integration and
      expression of the delta-6 and delta-5 desaturase genes and the
      elongase gene

<400> SEQUENCE: 124
tatcacatca cgctctcatc aagaatactt cttgagaacc gtggagaccg gggttcgatt      60
ccccgtatcg gagtgtttat ttttgctca accataccct ggggtgtgtt ctgtggagca     120
ttctcacttt tggtaaacga cattgcttca agtgcagcgg aatcaaaaag tataaagtgg    180

```
gcagcgagta tacctgtaca gactgtaggc gataactcaa tccaattacc ccccacaaca    240
tgactggcca aactgatctc aagactttat tgaaatcagc aacaccgatt ctcaatgaag    300
gcacatactt cttctgcaac attcacttga cgcctaaagt tggtgagaaa tggaccgaca    360
agacatattc tgctatccac ggactgttgc ctgtgtcggt ggctacaata cgtgagtcag    420
aagggctgac ggtggtggtt cgtacgttgt gtggaattgt gagcggataa caatttcaca    480
caggaaacag ctatgaccat gattacgcca agctcgaaat taaccctcac taaagggaac    540
aaaagctgga gctccaccgc ggacacaata tctggtcaaa tttcagtttc gttacataaa    600
tcgttatgtc aaaggagtgt gggaggttaa gagaattatc accggcaaac tatctgttaa    660
ttgctaggta cctctagacg tccacccggg tcgcttggcg gccgaagagg ccggaatctc    720
gggccgcggt ggcggccgct tactgcaact tccttgcctt ctccttggca gcgtcggcct    780
tggcctgctt ggccaacttg gcgttctttc tgtaaaagtt gtagaagaga ccgagcatgg    840
tccacatgta gaaccaaagc agagccgtga tgaagaaggg gtatccgggg cggccaagga    900
ccttcatggc gtacatgtcc caggaagact ggaccgacat catgcagaac tgtgtcatct    960
gcgagcgcgt gatgtagaac ttgatgaacg acacctgctt gaagcccaag gccgacaaga    1020
agtagtagcc gtacatgatc acatggatga acgagttcaa cgcagcagag aagtaggctt    1080
caccgttggg tgcaacaaag gtgaccaacc accagatggt gaagatggag ctgtggtggt    1140
aaacgtgcaa gaaggagatc tggcggttgt tcttcttgag gaccatgatc atggtgtcga    1200
caaactccat gatcttggag aagtagaaga gccagatcat cttggccata ggaagaccct    1260
tgaaggtatg atcagcagcg ttctcaaaca gtccatagtt ggcctgataa gcctcgtaca    1320
ggatcccacc gcacatgtag gcgctgatcg agaccagaca aaagttgtgc aggagcgaaa    1380
acgtcttgac ctcgaaccgc tcaaagttct tcatgatctg catgcccaca agaccgtga    1440 ccaaataagc gagcacgatc aacagcacgt ggaacgggtt catcaacggc agctcacggg    1500
ccaaaggcga ctccaccgcg accaggaacc cacgcgtgtg atggacaatc gtgggatgt    1560 acttctcggc ctgggccacc agcgcggcct cgagaggatc gacataggc gcggcccgga    1620 caccgatagc ggtggcaagg tccataaaca gatcttgcgg catctttgat gggaggaatg    1680
gcgcaatcga ctccatgcgg ccgctctaga actagtggat cctttgaatg attcttatac    1740
tcagaaggaa atgcttaacg atttcgggtg tgagttgaca aggagagaga gaaaagaaga    1800
ggaaaggtaa ttcggggacg gtggtctttt atacccttgg ctaaagtccc aaccacaaag    1860
caaaaaaatt ttcagtagtc tattttgcgt ccggcatggg ttacccggat ggccagacaa    1920
agaaactagt acaaagtctg aacaagcgta gattccagac tgcagtaccc tacgcccttta   1980 acggcaagtg tgggaaccgg gggaggtttg atatgtgggg tgaaggggc ctcgccggg    2040 gttgggcccg ctactgggtc aatttggggt caattggggc aattgggct gttttttggg    2100 acacaaatac gccgccaacc cggtctctcc tgaagcttgt gagcggataa caatttcaca    2160
caggaaacag ctatgaccat gattacgcca agctcgaaat taaccctcac taaagggaac    2220
aaaagctgga gctccaccgc ggacacaata tctggtcaaa tttcagtttc gttacataaa    2280
tcgttatgtc aaaggagtgt gggaggttaa gagaattatc accggcaaac tatctgttaa    2340
ttgctaggta cctctagacg tccacccggg tcgcttggcg gccgaagagg ccggaatctc    2400
gggccgcggt ggcggccgcc tactcttcct tgggacggag tccaagaaca cgcaagtgct    2460
ccaaatgtga agcaaatgct tgccaaaacg tatccttgac aaggtatgga accttgtact    2520
cgctgcaggt gttcttgatg atggccagaa tatcgggata atggtgctgc gacacgttgg    2580
```

```
ggaacagatg gtgcacagcc tggtagttca agctgccagt gatgctggtc cagaggtgcg   2640
aatcgtgtgc gtaatcctgc gtagtctcga cctgcatagc tgcccagtcc ttttggatga   2700
tcccgttctc gtcaggcaac ggccactgaa cttcctcaac aacgtggttc gcctggaagg   2760
tcagcgccag ccagtaagac gacaccatgt ccgcgaccgt gaacaagagc agcaccttgc   2820
ccaggggcag atactgcagg ggaacaatca ggcgatacca gacaaagaaa gccttgccgc   2880
cccagaacat cacagtgtgc catgtcgaga tgggattgac acgaatagcg tcattggtct   2940
tgacaaagta caaaatgttg atgtcctgaa tgcgcacctt gaacgccagc agtccgtaca   3000
ggaaaggaac aaacatgtgc tggttgatgt ggttgacaaa ccacttttgg ttgggcttga   3060
tacgacgaac atcgggctca gacgtcgaca cgtcgggatc tgctccagca atgttggtgt   3120
aggggtgatg gccgagcata tgttggtaca tccacaccag gtacgatgct ccgttgaaaa   3180
agtcgtgcgt ggctcccaga atcttccaga cagtggggtt gtgggtcact gaaaagtgag   3240
acgcatcatg aagagggttg agtccgactt gtgcgcacgc aaatcccatg atgattgcaa   3300
acaccacctg aagccatgtg cgttcgacaa cgaaaggcac aaagagctgc gcgtagtagg   3360
aagcgatcaa ggatccaaag ataagagcgt atcgtcccca gatctctggt ctattcttgg   3420
gatcaatgtt ccgatccgta aagtagccct cgactctcgt cttgatggtt ttgtggaaca   3480
ccgttggctc cgggaagatg ggcagctcat tcgagaccag tgtaccgaca tagtacttct   3540
tcataatggc atctgcagcc ccaaacgcgt gatacatctc aaagaccgga gtaacatctc   3600
ggccagctcc gagcaggaga gtgtccactc caccaggatg gcggctcaag aactttgtga   3660
catcgtacac cctgccgcgg atggccaaga gtaggtcgtc cttggtgtta tgggccgcca   3720
gctcttccca ggtgaaggtt tttccttggt ccgttcccat ggtgaatgat tcttatactc   3780
agaaggaaat gcttaacgat ttcgggtgtg agttgacaag gagagagaga aaagaagagg   3840
aaaggtaatt cggggacggt ggtctttat  acccttggct aaagtcccaa ccacaaagca   3900
aaaaaatttt cagtagtcta ttttgcgtcc ggcatgggtt acccggatgg ccagacaaag   3960
aaactagtac aaagtctgaa caagcgtaga ttccagactg cagtacccta cgcccttaac   4020
ggcaagtgtg ggaaccgggg gaggtttgat atgtggggtg aaggggggctc tcgccggggt   4080 tgggcccgct actgggtcaa tttggggtca attggggcaa ttggggctgt tttttgggac   4140
acaaatacgc cgccaacccg gtctctcctg aattctgcag atgggctgca ggaattccgt   4200
cgtcgcctga gtcgacatca tttatttacc agttggccac aaacccttga cgatctcgta   4260 tgtccctcc  gacatactcc cggccggctg gggtacgttc gatagcgcta tcggcatcga   4320
caaggtttgg gtccctagcc gataccgcac tacctgagtc acaatcttcg gaggtttagt   4380
cttccacata gcacgggcaa aagtgcgtat atatacaaga gcgtttgcca gccacagatt   4440
ttcactccac acaccacatc acacatacaa ccacacacat ccacaatgga acccgaaact   4500
aagaagacca agactgactc caagaagatt gttcttctcg gcggcgactt ctgtggcccc   4560
gaggtgattg ccgaggccgt caaggtgctc aagtctgttg ctgaggcctc cggcaccgag   4620
tttgtgtttg aggaccgact cattggagga gctgccattg agaaggaggg cgagcccatc   4680
accgacgcta ctctcgacat ctgccgaaag gctgactcta ttatgctcgg tgctgtcgga   4740
ggcgctgcca acaccgtatg gaccactccc gacggacgaa ccgacgtgcg acccgagcag   4800
ggtctcctca agctgcgaaa ggacctgaac ctgtacgcca acctgcgacc ctgccagctg   4860
ctgtcgccca agctcgccga tctctccccc atccgaaacg ttgagggcac cgacttcatc   4920
```

```
attgtccgag agctcgtcgg aggtatctac tttggagagc gaaaggagga tgacggatct    4980
ggcgtcgctt ccgacaccga gacctactcc gttcctgagg ttgagcgaat tgcccgaatg    5040
gccgccttcc tggcccttca gcacaacccc cctcttcccg tgtggtctct tgacaaggcc    5100
aacgtgctgg cctcctctcg actttggcga aagactgtca ctcgagtcct caaggacgaa    5160
ttcccccagc tcgagctcaa ccaccagctg atcgactcgg ccgccatgat cctcatcaag    5220
cagccctcca agatgaatgg tatcatcatc accaccaaca tgtttggcga tatcatctcc    5280
gacgaggcct ccgtcatccc cggttctctg gtctgctgc cctccgcctc tctggcttct    5340
ctgcccgaca ccaacgaggc gttcggtctg tacgagccct gtcacggatc tgcccccgat    5400
ctcggcaagc agaaggtcaa ccccattgcc accattctgt ctgccgccat gatgctcaag    5460
ttctctctta acatgaagcc cgccggtgac gctgttgagg ctgccgtcaa ggagtccgtc    5520
gaggctggta tcactaccgc cgatatcgga ggctcttcct ccacctccga ggtcggagac    5580
ttgttgccaa caaggtcaag gagctgctca agaaggagta agtcgtttct acgacgcatt    5640
gatggaagga gcaaactgac gcgcctgcgg gttggtctac cggcagggtc cgctagtgta    5700
taagactcta taaaagggc cctgccctgc taatgaaatg atgatttata atttaccggt    5760
gtagcaacct tgactagaag aagcagattg ggtgtgtttg tagtggagga cagtggtacg    5820
ttttggaaac agtcttcttg aaagtgtctt gtctacagta tattcactca taacctcaat    5880
agccaagggt gtagtcggtt tattaaagga agggagttgt ggctgatgtg gatagatatc    5940
tttaagctgg cgactgcacc caacgagtgt ggtggtagct tgttactgta tattcggtaa    6000
gatatatttt gtggggtttt agtggtgttt aaacggtagg ttagtgcttg gtatatgagt    6060
tgtaggcatg acaatttgga aaggggtgga ctttgggaat attgtgggat ttcaatacct    6120
tagtttgtac agggtaattg ttacaaatga tacaaagaac tgtatttctt ttcatttgtt    6180
ttaattggtt gtatatcaag tccgttagac gagctcagtg ccttggcttt tggcactgta    6240
tttcattttt agaggtacac tacattcagt gaggtatggt aaggttgagg cataatgaa    6300
ggcaccttgt actgacagtc acagacctct caccgagaat tttatgagat atactcgggt    6360
tcatttagg ctcatcgatg cagaattcag gagagaccgg gttgcggcg tatttgtgtc    6420
ccaaaaaaca gccccaattg ccccaattga ccccaaattg acccagtagc gggcccaacc    6480
ccggcgagag ccccttcac cccacatatc aaacctcccc cggttcccac acttgccgtt    6540
aagggcgtag ggtactgcag tctgaatct acgcttgttc agactttgta ctagtttctt    6600
tgtctggcca tccgggtaac ccatgccgga cgcaaaatag actactgaaa atttttttgc    6660
tttgtggttg ggactttagc caagggtata aagaccacc gtccccgaat tacctttcct    6720
cttcttttct ctctctcctt gtcaactcac acccgaaatc gttaagcatt ccttctgag    6780
tataagaatc attcaccatg gctgctgctc ccagtgtgag gacgtttact cgggccgagg    6840
ttttgaatgc cgaggctctg aatgagggca agaaggatgc cgaggcaccc ttcttgatga    6900
tcatcgacaa caaggtgtac gatgtccgcg agttcgtccc tgatcatccc ggtggaagtg    6960
tgattctcac gcacgttggc aaggacggca ctgacgtctt tgacactttt caccccgagg    7020
ctgcttggga gactcttgcc aacttttacg ttggtgatat tgacgagagc gaccgcgata    7080
tcaagaatga tgactttgcg gccgaggtcc gcaagctgcg taccttgttc cagtctcttg    7140
gttactacga ttcttccaag gcatactacg ccttcaaggt ctcgttcaac ctctgcatct    7200
ggggtttgtc gacggtcatt gtggccaagt ggggccagac ctcgaccctc gccaacgtgc    7260
tctcggctgc gcttttgggt ctgttctggc agcagtgcgg atggttggct cacgactttt    7320
```

-continued

```
tgcatcacca ggtcttccag gaccgtttct ggggtgatct tttcggcgcc ttcttgggag    7380
gtgtctgcca gggcttctcg tcctcgtggt ggaaggacaa gcacaacact caccacgccg    7440
cccccaacgt ccacggcgag gatcccgaca ttgacaccca ccctctgttg acctggagtg    7500
agcatgcgtt ggagatgttc tcggatgtcc cagatgagga gctgacccgc atgtggtcgc    7560
gtttcatggt cctgaaccag acctggtttt acttccccat tctctcgttt gcccgtctct    7620
cctggtgcct ccagtccatt ctctttgtgc tgcctaacgg tcaggcccac aagccctcgg    7680
gcgcgcgtgt gcccatctcg ttggtcgagc agctgtcgct tgcgatgcac tggacctggt    7740
acctcgccac catgttcctg ttcatcaagg atcccgtcaa catgctggtg tacttttt gg    7800 tgtcgcaggc ggtgtgcgga aacttgttgg ccatcgtgtt ctcgctcaac cacaacggta    7860
tgcctgtgat ctcgaggagg aggcggtcga tatggatttc ttcacgaagc agatcatcac    7920
gggtcgtgat gtccacccgg gtctatttgc caactggttc acgggtggat tgaactatca    7980
gatcgagcac cacttgttcc cttcgatgcc tcgccacaac ttttcaaaga tccagcctgc    8040
tgtcgagacc ctgtgcaaaa agtacaatgt ccgataccac accaccgta tgatcgaggg    8100 aactgcagag gtctttagcc gtctgaacga ggtctccaag gctacctcca agatgggtaa    8160
ggcgcagtaa gcggccgcca ccgcggcccg agattccggc ctcttcggcc gccaagcgac    8220
ccgggtggac gtctagaggt acctagcaat taacagatag tttgccggtg ataattctct    8280
taacctccca cactcctttg acataacgat ttatgtaacg aaactgaaat ttgaccagat    8340
attgtgtccg cggtggagct ccagcttttg ttccctttag tgagggttaa ttaattcgat    8400
atcataattg tcggccgagg tctgtacggc cagaaccgag atcctattga ggaggccaag    8460
cgataccaga aggctggctg ggaggcttac cagaagatta actgttagag gttagactat    8520
ggatatgtca tttaactgtg tatatagaga gcgtgcaagt atggagcgct tgttcagctt    8580
gtatgatggt cagacgacct gtctgatcga gtatgtgatga tactgcacaa cctgtgtatc    8640
cgcatgatct gtccaatggg gcatgttgtt gtgtttctcg atacggagat gctgggtaca    8700
agtagctaat acgattgaac tacttatact tatatgaggc ttgaagaaag ctgacttgtg    8760
tatgacttat tctcaactac atccccagtc acaataccac cactgcacta ccactacacc    8820
aaaaccatga tcaaaccacc catggacttc ctggaggcag aagaacttgt tatggaaaag    8880
ctcaagagag agaa                                                     8894
```

<210> SEQ ID NO 125
<211> LENGTH: 31
<212> TYPE: DNA
<213> ORGANISM: Artificial Sequence
<220> FEATURE:
<223> OTHER INFORMATION: Primer YL101

<400> SEQUENCE: 125
gagcttggcg taatcgatgg tcatagctgt t                              31

<210> SEQ ID NO 126
<211> LENGTH: 31
<212> TYPE: DNA
<213> ORGANISM: Artificial Sequence
<220> FEATURE:
<223> OTHER INFORMATION: Primer YL102

<400> SEQUENCE: 126
aacagctatg accatcgatt acgccaagct c                              31

```
<210> SEQ ID NO 127
<211> LENGTH: 36
<212> TYPE: DNA
<213> ORGANISM: Artificial Sequence
<220> FEATURE:
<223> OTHER INFORMATION: Primer YL103

<400> SEQUENCE: 127
atgatgactc aggcgtttaa acgacggaat tcctgc                                 36

<210> SEQ ID NO 128
<211> LENGTH: 36
<212> TYPE: DNA
<213> ORGANISM: Artificial Sequence
<220> FEATURE:
<223> OTHER INFORMATION: Primer YL104

<400> SEQUENCE: 128
gcaggaattc cgtcgtttaa acgcctgagt catcat                                 36

<210> SEQ ID NO 129
<211> LENGTH: 10328
<212> TYPE: DNA
<213> ORGANISM: Artificial Sequence
<220> FEATURE:
<223> OTHER INFORMATION: 10328 bp fragment for integration and
      expression of the delta-6, delta-5, and delta-17 desaturase
      genes and the elongase gene

<400> SEQUENCE: 129
tatcacatca cgctctcatc aagaatactt cttgagaacc gtggagaccg gggttcgatt        60
ccccgtatcg gagtgtttat tttttgctca accataccct ggggtgtgtt ctgtggagca       120
ttctcacttt tggtaaacga cattgcttca agtgcagcgg aatcaaaaag tataaagtgg       180
gcagcgagta tacctgtaca gactgtaggc gataactcaa tccaattacc ccccacaaca       240
tgactggcca aactgatctc aagactttat tgaaatcagc aacaccgatt ctcaatgaag       300
gcacatactt cttctgcaac attcacttga cgcctaaagt tggtgagaaa tggaccgaca       360
agacatattc tgctatccac ggactgttgc ctgtgtcggt ggctacaata cgtgagtcag       420
aagggctgac ggtggtggtt cgtacgttgt gtggaattgt gagcggataa caatttcaca       480
caggaaacag ctatgaccat gattacgcca agctcgaaat taaccctcac taagggaac       540 aaaagctgga gctccaccgc ggacacaata tctggtcaaa tttcagtttc gttacataaa       600
tcgttatgtc aaaggagtgt gggaggttaa gagaattatc accggcaaac tatctgttaa       660
ttgctaggta cctctagacg tccacccggg tcgcttggcg gccgaagagg ccggaatctc       720
gggccgcggt ggcggccgct tactgcaact tccttgcctt ctccttggca gcgtcggcct       780
tggcctgctt ggccaacttg gcgttctttc tgtaaaagtt gtagaagaga ccgagcatgg       840
tccacatgta gaaccaaagc agagccgtga tgaagaaggg gtatccgggg cggccaagga       900
ccttcatggc gtacatgtcc caggaagact ggaccgacat catgcagaac tgtgtcatct       960
gcgagcgcgt gatgtagaac ttgatgaacg acacctgctt gaagcccaag gccgacaaga      1020
agtagtagcc gtacatgatc acatggatga acgagttcaa cgcagcagag aagtaggctt      1080
caccgttggg tgcaacaaag gtgaccaacc accagatggt gaagatggag ctgtggtggt      1140
```

```
aaacgtgcaa gaaggagatc tggcggttgt tcttcttgag gaccatgatc atggtgtcga    1200
caaactccat gatcttggag aagtagaaga gccagatcat cttggccata ggaagaccct    1260
tgaaggtatg atcagcagcg ttctcaaaca gtccatagtt ggcctgataa gcctcgtaca    1320
ggatcccacc gcacatgtag gcgctgatcg agaccagaca aaagttgtgc aggagcgaaa    1380
acgtcttgac ctcgaaccgc tcaaagttct tcatgatctg catgcccaca agaccgtga     1440 ccaaataagc gagcacgatc aacagcacgt ggaacgggtt catcaacggc agctcacggg    1500
ccaaaggcga ctccaccgcg accaggaacc cacgcgtgtg atggacaatc gtgggatgt     1560 acttctcggc ctgggccacc agcgcggcct cgagaggatc gacataggc gcggcccgga    1620 caccgatagc ggtggcaagg tccataaaca gatcttgcgg catctttgat gggaggaatg    1680
gcgcaatcga ctccatgcgg ccgctctaga actagtggat cctttgaatg attcttatac    1740
tcagaaggaa atgcttaacg atttcgggtg tgagttgaca aggagagaga gaaaagaaga    1800
ggaaaggtaa ttcggggacg gtggtctttt ataccctcgg ctaaagtccc aaccacaaag    1860
caaaaaaatt ttcagtagtc tattttgcgt ccggcatggg ttacccggat ggccagacaa    1920
agaaactagt acaaagtctg aacaagcgta gattccagac tgcagtaccc tacgcccctta   1980 acggcaagtg tgggaaccgg gggaggtttg atatgtgggg tgaagggggc tctcgccggg    2040
gttgggcccg ctactgggtc aatttggggt caattgggc aattgggct gtttttggg       2100 acacaaatac gccgccaacc cggtctctcc tgaagcttgt gagcggataa caatttcaca    2160
caggaaacag ctatgaccat gattacgcca agctcgaaat taaccctcac taaagggaac    2220
aaaagctgga gctccaccgc ggacacaata tctggtcaaa tttcagtttc gttacataaa    2280
tcgttatgtc aaaggagtgt gggaggttaa gagaattatc accggcaaac tatctgttaa    2340
ttgctaggta cctctagacg tccacccggg tcgcttggcg gccgaagagg ccggaatctc    2400
gggccgcggt ggcggccgcc tactcttcct tgggacggag tccaagaaca cgcaagtgct    2460
ccaaatgtga agcaaatgct tgccaaaacg tatccttgac aaggtatgga accttgtact    2520
cgctgcaggt gttcttgatg atggccagaa tatcgggata atggtgctgc gacacgttgg    2580
ggaacagatg gtgcacagcc tggtagttca agctgccagt gatgctggtc cagaggtgcg    2640
aatcgtgtgc gtaatcctgc gtagtctcga cctgcatagc tgcccagtcc ttttggatga    2700
tcccgttctc gtcaggcaac ggccactgaa cttcctcaac aacgtggttc gcctggaagg    2760
tcagcgccag ccagtaagac gacaccatgt ccgcgaccgt gaacaagagc agcaccttgc    2820
ccaggggcag atactgcagg ggaacaatca ggcgatacca gacaaagaaa gccttgccgc    2880
cccagaacat cacagtgtgc catgtcgaga tgggattgac acgaatagcg tcattggtct    2940
tgacaaagta caaaatgttg atgtcctgaa tgcgcacctt gaacgccagc agtccgtaca    3000
ggaaaggaac aaacatgtgc tggttgatgt ggttgacaaa ccacttttgg ttgggcttga    3060
tacgacgaac atcgggctca gacgtcgaca cgtcggatc tgctccagca atgttggtgt     3120
aggggtgatg gccgagcata tgttggtaca tccacaccag gtacgatgct ccgttgaaaa    3180
agtcgtgcgt ggctcccaga atcttccaga cagtgggggtt gtgggtcact gaaaagtgag   3240
acgcatcatg aagagggttg agtccgactt gtgcgcacgc aaatcccatg atgattgcaa    3300
acaccacctg aagccatgtg cgttcgacaa cgaaaggcac aaagagctgc gcgtagtagg    3360
aagcgatcaa ggatccaaag ataagagcgt atcgtcccca gatctctggt ctattcttgg    3420
gatcaatgtt ccgatccgta aagtagccct cgactctcgt cttgatggtt ttgtggaaca    3480
ccgttggctc cgggaagatg ggcagctcat tcgagaccag tgtaccgaca tagtacttct    3540
```

```
tcataatggc atctgcagcc ccaaacgcgt gatacatctc aaagaccgga gtaacatctc    3600
ggccagctcc gagcaggaga gtgtccactc caccaggatg gcggctcaag aactttgtga    3660
catcgtacac cctgccgcgg atggccaaga gtaggtcgtc cttggtgtta tgggccgcca    3720
gctcttccca ggtgaaggtt tttccttggt ccgttcccat ggtgaatgat tcttatactc    3780
agaaggaaat gcttaacgat ttcgggtgtg agttgacaag gagagagaga aaagaagagg    3840
aaaggtaatt cggggacggt ggtctttat accttggct aaagtcccaa ccacaaagca      3900
aaaaatttt cagtagtcta ttttgcgtcc ggcatgggtt acccggatgg ccagacaaag     3960
aaactagtac aaagtctgaa caagcgtaga ttccagactg cagtacccta cgcccttaac    4020
ggcaagtgtg ggaaccgggg gaggtttgat atgtggggtg aagggggctc tcgccgggt     4080
tgggcccgct actgggtcaa tttggggtca attggggcaa ttgggctgt ttttgggac      4140
acaaatacgc cgccaacccg gtctctcctg aattctgcag atgggctgca ggaattccgt    4200
cgtcgcctga gtcgacatca tttatttacc agttggccac aaaccctga cgatctcgta     4260
tgtcccctcc gacatactcc cggccggctg gggtacgttc gatagcgcta tcggcatcga    4320
caaggtttgg gtccctagcc gataccgcac tacctgagtc acaatcttcg gaggtttagt    4380
cttccacata gcacgggcaa aagtgcgtat atatacaaga gcgtttgcca gccacagatt    4440
ttcactccac acaccacatc acacatacaa ccacacacat ccacaatgga acccgaaact    4500
aagaagacca agactgactc caagaagatt gttcttctcg gcggcgactt ctgtggcccc    4560
gaggtgattg ccgaggccgt caaggtgctc aagtctgttg ctgaggcctc cggcaccgag    4620
tttgtgtttg aggaccgact cattggagga gctgccattg agaaggaggg cgagcccatc    4680
accgacgcta ctctcgacat ctgccgaaag gctgactcta ttatgctcgg tgctgtcgga    4740
ggcgctgcca acaccgtatg gaccactccc gacggacgaa ccgacgtgcg acccgagcag    4800
ggtctcctca gctgcgaaa ggacctgaac ctgtacgcca acctgcgacc ctgccagctg     4860
ctgtcgccca agctcgccga tctctccccc atccgaaacg ttgagggcac cgacttcatc    4920
attgtccgag agctcgtcgg aggtatctac tttggagagc gaaaggagga tgacggatct    4980
ggcgtcgctt ccgacaccga gacctactcc gttcctgagg ttgagcgaat gcccgaatg     5040
gccgccttcc tggcccttca gcacaacccc cctcttcccg tgtggtctct tgacaaggcc    5100
aacgtgctgg cctcctctcg actttggcga aagactgtca ctcgagtcct caaggacgaa    5160
ttcccccagc tcgagctcaa ccaccagctg atcgactcgg ccgccatgat cctcatcaag    5220
cagccctcca agatgaatgg tatcatcatc accaccaaca tgtttggcga tatcatctcc    5280
gacgaggcct ccgtcatccc cggttctctg ggtctgctgc cctccgcctc tctggcttct    5340
ctgcccgaca ccaacgaggc gttcggtctg tacgagccct gtcacggatc tgcccccgat    5400
ctcggcaagc agaaggtcaa ccccattgcc accattctgt ctgccgccat gatgctcaag    5460
ttctctctta acatgaagcc cgccggtgac gctgttgagg ctgccgtcaa ggagtccgtc    5520
gaggctggta tcactaccgc cgatatcgga ggctcttcct ccacctccga ggtcggagac    5580
ttgttgccaa caaggtcaag gagctgctca agaaggagta agtcgtttct acgacgcatt    5640
gatggaagga gcaaactgac gcgcctgcgg gttggtctac cggcagggtc cgctagtgta    5700
taagactcta taaaagggc cctgccctgc taatgaaatg atgatttata atttaccggt     5760
gtagcaacct tgactagaag aagcagattg ggtgtgtttg tagtggagga cagtggtacg    5820
ttttggaaac agtcttcttg aaagtgtctt gtctacagta tattcactca taacctcaat    5880
```

```
agccaagggt gtagtcggtt tattaaagga agggagttgt ggctgatgtg gatagatatc    5940
tttaagctgg cgactgcacc caacgagtgt ggtggtagct tgttactgta tattcggtaa    6000
gatatatttt gtggggtttt agtggtgttt aaacgacgga attcctgcag cccatctgca    6060
gaattcagga gagaccgggt tggcggcgta tttgtgtccc aaaaaacagc cccaattgcc    6120
ccaattgacc ccaaattgac ccagtagcgg gcccaacccc ggcgagagcc cccttcaccc    6180
cacatatcaa acctcccccg gttcccacac ttgccgttaa gggcgtaggg tactgcagtc    6240
tggaatctac gcttgttcag actttgtact agtttctttg tctggccatc cgggtaaccc    6300
atgccggacg caaaatagac tactgaaaat ttttttgctt tgtggttggg actttagcca    6360
agggtataaa agaccaccgt ccccgaatta ccttttcctct tcttttctct ctctccttgt    6420
caactcacac ccgaaatcgt taagcatttc cttctgagta taagaatcat tcaccatggc    6480
tgaggataag accaaggtcg agttccctac cctgactgag ctgaagcact ctatccctaa    6540
cgcttgcttt gagtccaacc tcggactctc gctctactac actgcccgag cgatcttcaa    6600
cgcatctgcc tctgctgctc tgctctacgc tgcccgatct actcccttca ttgccgataa    6660
cgttctgctc cacgctctgg tttgcgccac ctacatctac gtgcagggtg tcatcttctg    6720
gggtttcttt accgtcggtc acgactgtgg tcactctgcc ttctcccgat accactccgt    6780
caacttcatc attggctgca tcatgcactc tgccattctg actcccttcg agtcctggcg    6840
agtgacccac cgacaccatc acaagaacac tggcaacatt gataaggacg agatcttcta    6900
ccctcatcgg tccgtcaagg acctccagga cgtgcgacaa tgggtctaca ccctcggagg    6960
tgcttggttt gtctacctga aggtcggata tgctcctcga accatgtccc actttgaccc    7020
ctgggaccct ctcctgcttc gacgagcctc cgctgtcatc gtgtccctcg gagtctgggc    7080
tgccttcttc gctgcctacg cctacctcac atactcgctc ggctttgccg tcatgggcct    7140
ctactactat gctcctctct ttgtctttgc ttcgttcctc gtcattacta ccttcttgca    7200
tcacaacgac gaagctactc cctggtacgg tgactcggag tggacctacg tcaagggcaa    7260
cctgagctcc gtcgaccgat cgtacggagc tttcgtggac aacctgtctc accacattgg    7320
cacccaccag gtccatcact tgttccctat cattccccac tacaagctca cgaagccac     7380 caagcacttt gctgccgctt accctcacct cgtgagacgt aacgacgagc ccatcattac    7440
tgccttcttc aagaccgctc acctctttgt caactacgga gctgtgcccg agactgctca    7500
gattttcacc ctcaaagagt ctgccgctgc agccaaggcc aagagcgacc accaccatca    7560
ccaccattaa gcggccgcca ccgcggcccg agattccggc ctcttcggcc gccaagcgac    7620
ccgggtggac gtctagaggt acctagcaat taacagatag tttgccggtg ataattctct    7680
taacctccca cactcctttg acataacgat ttatgtaacg aaactgaaat ttgaccagat    7740
attgtgtccg cggtggagct ccagcttttg ttccctttag tgagggttaa tttcgagctt    7800
ggcgtaatcg atgcagaatt caggagagac cgggttggcg gcgtatttgt gtcccaaaaa    7860
acagccccaa ttgccccaat tgaccccaaa ttgacccagt agcgggccca accccggcga    7920
gagccccctt caccccacat atcaaacctc ccccggttcc cacacttgcc gttaagggcg    7980
tagggtactg cagtctggaa tctacgcttg ttcagacttt gtactagttt ctttgtctgg    8040
ccatccgggt aacccatgcc ggacgcaaaa tagactactg aaaattttttt tgctttgtgg    8100 ttgggacttt agccaagggt ataaaagacc accgtccccg aattacctttt cctcttcttt    8160 tctctctctc cttgtcaact cacacccgaa atcgttaagc atttccttct gagtataaga    8220
atcattcacc atggctgctg ctcccagtgt gaggacgttt actcgggccg aggttttgaa    8280
```

```
tgccgaggct ctgaatgagg gcaagaagga tgccgaggca cccttcttga tgatcatcga    8340
caacaaggtg tacgatgtcc gcgagttcgt ccctgatcat cccggtggaa gtgtgattct    8400
cacgcacgtt ggcaaggacg gcactgacgt ctttgacact tttcaccccg aggctgcttg    8460
ggagactctt gccaactttt acgttggtga tattgacgag agcgaccgcg atatcaagaa    8520
tgatgacttt gcggccgagg tccgcaagct gcgtaccttg ttccagtctc ttggttacta    8580
cgattcttcc aaggcatact acgccttcaa ggtctcgttc aacctctgca tctggggttt    8640
gtcgacggtc attgtggcca agtggggcca gacctcgacc ctcgccaacg tgctctcggc    8700
tgcgcttttg ggtctgttct ggcagcagtg cggatggttg gctcacgact ttttgcatca    8760
ccaggtcttc caggaccgtt tctggggtga tcttttcggc gccttcttgg gaggtgtctg    8820
ccagggcttc tcgtcctcgt ggtggaagga caagcacaac actcaccacg ccgcccccaa    8880
cgtccacggc gaggatcccg acattgacac ccaccctctg ttgacctgga gtgagcatgc    8940
gttggagatg ttctcggatg tcccagatga ggagctgacc cgcatgtggt cgcgtttcat    9000
ggtcctgaac cagacctggt tttacttccc cattctctcg tttgcccgtc tctcctggtg    9060
cctccagtcc attctctttg tgctgcctaa cggtcaggcc cacaagccct cgggcgcgcg    9120
tgtgcccatc tcgttggtcg agcagctgtc gcttgcgatg cactggacct ggtacctcgc    9180
caccatgttc ctgttcatca aggatcccgt caacatgctg gtgtactttt tggtgtcgca    9240
ggcggtgtgc ggaaacttgt tggccatcgt gttctcgctc aaccacaacg gtatgcctgt    9300
gatctcgaag gaggaggcgg tcgatatgga tttcttcacg aagcagatca tcacgggtcg    9360
tgatgtccac ccgggtctat ttgccaactg gttcacgggt ggattgaact atcagatcga    9420
gcaccacttg ttcccttcga tgcctcgcca caacttttca aagatccagc ctgctgtcga    9480
gaccctgtgc aaaaagtaca atgtccgata ccacaccacc ggtatgatcg agggaactgc    9540
agaggtcttt agccgtctga cgaggtctc caaggctacc tccaagatgg gtaaggcgca    9600
gtaagcggcc gccaccgcgg cccgagattc cggcctcttc ggccgccaag cgacccgggt    9660
ggacgtctag aggtacctag caattaacag atagtttgcc ggtgataatt ctcttaacct    9720
cccacactcc tttgacataa cgatttatgt aacgaaactg aaatttgacc agatattgtg    9780
tccgcggtgg agctccagct tttgttccct ttagtgaggg ttaattaatt cgatatcata    9840
attgtcggcc gaggtctgta cggccagaac cgagatccta ttgaggaggc caagcgatac    9900
cagaaggctg gctgggaggc ttaccagaag attaactgtt agaggttaga ctatggatat    9960
gtcatttaac tgtgtatata gagagcgtgc aagtatggag cgcttgttca gcttgtatga   10020
tggtcagacg acctgtctga tcgagtatgt atgatactgc acaacctgtg tatccgcatg   10080
atctgtccaa tggggcatgt tgttgtgttt ctcgatacgg agatgctggg tacaagtagc   10140
taatacgatt gaactactta tacttatatg aggcttgaag aaagctgact tgtgtatgac   10200
ttattctcaa ctacatcccc agtcacaata ccaccactgc actaccacta caccaaaacc   10260
atgatcaaac cacccatgga cttcctggag gcagaagaac ttgttatgga aaagctcaag   10320
agagagaa                                                           10328
```

<210> SEQ ID NO 130
<211> LENGTH: 10
<212> TYPE: DNA
<213> ORGANISM: Yarrowia lipolytica
<220> FEATURE:
<221> NAME/KEY: misc_feature
<222> LOCATION: (8)..(8)

```
<223> OTHER INFORMATION: n is a, c, g, or t

<400> SEQUENCE: 130 mammatgnhs                                                          10
```

What is claimed is:

1. A method for the production of linoleic acid comprising:
   a) providing a microbial host cell, wherein the microbial host cell is *Yarrowia*, comprising:
      (i) a chimeric gene encoding a Δ12 desaturase polypeptide selected from the group consisting of:
         (a) an isolated nucleic acid molecule encoding a polypeptide having Δ12 desaturase activity wherein the polypeptide has at least 90% sequence identity when compared to an amino acid sequence as set forth in SEQ ID NO:24, and
         (b) an isolated nucleic acid molecule encoding a polypeptide having Δ12 desaturase activity, wherein the nucleic acid molecule hybridizes with a nucleotide sequence as set forth in SEQ ID NO:23 under the following hybridization conditions: 0.1× SSC, 0.1% SDS, 65° C. and washed with 2×SSC, 0.1% SDS followed by 0.1×SSC, 0.1% SDS; and
      (ii) a source of desaturase substrate consisting of oleic acid;
   b) growing the microbial host cell of step (a) under conditions wherein the gene encoding a Δ12 desaturase polypeptide is expressed and the oleic acid is converted to linoleic acid; and
   c) optionally recovering the linoleic acid of step (b).

2. A method for modulating the biosynthesis of ω-3 fatty acids in an oleaginous yeast cell comprising:
   a) providing an oleaginous yeast cell, comprising a functional ω-3 fatty acid biosynthetic pathway;
   b) over-expressing a Δ12 desaturase gene in the oleaginous yeast of (a), wherein said Δ12 desaturase gene is selected from the group consisting of:
      (i) an isolated nucleic acid molecule encoding a polypeptide having Δ12 desaturase activity wherein the polypeptide has at least 90% sequence identity when compared to an amino acid sequence as set forth in SEQ ID NO:24, and
      (ii) an isolated nucleic acid molecule encoding a polypeptide having Δ12 desaturase activity, wherein the nucleic acid molecule hybridizes with a nucleotide sequence as set forth in SEQ ID NO:23 under the following hybridization conditions: 0.1× SSC, 0.1% SDS, 65° C. and washed with 2×SSC, 0.1% SDS followed by 0.1×SSC, 0.1% SDS;
   whereby the biosynthesis of ω-3 fatty acids is modulated.

3. The method according to claim 2 wherein the Δ12 desaturase gene is over-expressed on a multicopy plasmid.

4. The method according to claim 2 wherein the Δ12 desaturase gene is operably linked to an inducible or regulated promoter.

* * * * *